(12) United States Patent
Chemtob et al.

(10) Patent No.: US 7,432,341 B2
(45) Date of Patent: Oct. 7, 2008

(54) CYTOKINE RECEPTOR MODULATORS AND METHOD OF MODULATING CYTOKINE RECEPTOR ACTIVITY

(75) Inventors: Sylvain Chemtob, Côte St-Luc (CA); Christiane Quiniou, Montreal (CA); Martin Beauchamp, Laval (CA)

(73) Assignee: Valo HSJ, Limited Partnership, Montreal (CA)

( * ) Notice: Subject to any disclaimer, the term of this patent is extended or adjusted under 35 U.S.C. 154(b) by 497 days.

(21) Appl. No.: 10/693,657

(22) Filed: Oct. 24, 2003

(65) Prior Publication Data
US 2007/0037210 A1 Feb. 15, 2007

Related U.S. Application Data

(60) Provisional application No. 60/423,530, filed on Nov. 5, 2002, provisional application No. 60/420,679, filed on Oct. 24, 2002.

(51) Int. Cl.
*A61K 38/00* (2006.01)
*A61K 38/04* (2006.01)
*C07K 7/00* (2006.01)

(52) U.S. Cl. ............................. 530/300; 530/328; 514/2
(58) Field of Classification Search ....................... None
See application file for complete search history.

(56) References Cited

U.S. PATENT DOCUMENTS

| 5,223,409 | A |  | 6/1993 | Ladner et al. ............... 435/69.7 |
| 5,712,380 | A | * | 1/1998 | Kendall et al. .............. 536/23.5 |
| 5,952,199 | A | * | 9/1999 | Davis-Smyth et al. ...... 435/69.7 |

FOREIGN PATENT DOCUMENTS

WO    WO 93/14781    8/1993

OTHER PUBLICATIONS

Mickle J.E. et al. Genotype-phenotype relationships in cystic fibrosis. Med. Clin. North Am. 2000. vol. 84, p. 597-607.*
Binetruy-Tournaire, R. et al. Identification of a peptide blocking vascular endothelial growth factor (VEGF)-mediated angiogenesis. EMBO J. 2000. vol. 19, p. 1525-1533.*
Mohamed-Habib B.A. et al. rIL-2-induced proliferation of human circulating NK cells and T lymphocytes: Synergistic effects of IL-1 and IL-2. J. Immunology. 1987. vol. 139, No. 2., pp. 443-451.*
Baker et al., "Cell proliferation kinetics of normal and tumour tissue in vitro: quiescent reproductive cells and the cycling reproductive fraction," *Cell Prolif.*, 28(1):1-15, 1995.
Brady and Dodson, "Reflections on a peptide," *Nature*, 368:692-693, 1994.
Carell et al., "A novel procedure for the synthesis of libraries containing small organic molecules," *Angew Chem Int Ed Engl*, 33(20):2059-2061, 1994.
Cheviron et al., "The antiproliferative activity of the tetra peptide acetyl-N-SerAspLysPro, an inhibitor of hematopoietic stem cell proliferation, is not mediated by a thymosin β4-like effect on actin assembly," *Cell Prolif.*, 29(8):437-446, 1996.
Cho et al., "An unnatural biopolymer," *Science*, 261:1303-1305, 1993.
Coller et al., "Substituting isoserine for serine in the thrombin receptor activation peptide SFLLRN confers resistance to aminopeptidase M-induced cleavage and inactivation," *J. Biol. Chem.*, 268:20741-20743, 1993.
Cull et al., "Screening for receptor ligands using large libraries of peptides linked to the C terminus of the lac repressor," *Proc. Natl. Acad. Sci.*, USA, 89:1865-1869, 1992.
DeWitt et al., "'Diversomers': an approach to nonpeptide, nonoligomeric chemical diversity," *Proc. Natl. Acad. Sci.*, USA, 90:6909-6913, 1993.
Elliot et al., "Bin1 functionally interacts with myc and inhibits cell proliferation via multiple mechanisms," *Oncogene*, 18(24):3564-3573, 1999.
Erb et al., "Recursive deconvolution of combinatorial chemical libraries," *Proc. Natl. Acad. Sci.*, USA, 91:11422-11426, 1994.
Fodor et al., "Multiplexed biochemical assays with biological chips," *Nature*, 364:555-556, 1993.
Gallop et al., "Applications of combinatorial technologies to drug discovery. 1. Background and peptide combinatorial libraries," *Journal of Medicinal Chemistry*, 37(9):1233-1251, 1994.
Houghten et al., "The use of synthetic peptide combinatorial libraries for the identification of bioactive peptides," *BioTechniques*, 13(3):412-421, 1992.
Hu et al., "$\alpha_1$-adrenergic receptor stimulation of mitogenesis in human vascular smooth muscle cells: role of tyrosine protein kinases and calcium in activation of mitogen-activated protein kinase[1]," *J. Pharmacol. Exp. Ther.*, 290(1):28-37, 1999.
Jameson et al., "A rationally designed CD4 analogue inhibits experimental alergic encephalomyelitis," *Nature*, 368:744-746, 1994.
Lam et al., "A new type synthetic peptide library for identifying ligand-binding activity," *Nature*, 354:744-746, 1994.

(Continued)

*Primary Examiner*—Robert Landsman
*Assistant Examiner*—Bruce D. Hissong
(74) *Attorney, Agent, or Firm*—Clark & Elbing LLP; Kristina Bieker-Brady; Jan N. Tittel

(57) ABSTRACT

The present invention relates to a method for identifying a non-competitive peptide, which inhibits the activity of a cytokine receptor. This method includes the steps of selecting a candidate peptide containing from about 7 to about 20 amino acids derived from a flexible region of a cytokine receptor, and determining the ability of the peptide to inhibit or promote the oligomerization and/or activation of the receptor by measuring an activity of the receptor in the absence or the presence of the candidate peptide, wherein the non-competitive peptide is selected when the activity of the receptor is measurably lower in the presence of the peptide as compared to in the absence of the peptide so identified. This invention also provides agonists of cytokine receptor activity. Pharmaceutical compositions that comprise the identified peptides are disclosed. Also disclosed are methods for treating patients with a disease or condition associated with abnormal cytokine receptor mediated function or activity such as inflammatory, autoimmune and vascular diseases.

3 Claims, 17 Drawing Sheets

OTHER PUBLICATIONS

Lam, "Application of combinatorial library methods in cancer research and drug discovery," *Anti-Cancer Drug Design*, 12:145-167, 1997.

Merrifield, "Solid phase peptide synthesis. I. The synthesis of a tetrapeptide," *J. Am. Chem. Soc.*, 85:2149, 1964.

Piossek et al., Vascular endothelial growth factor (VEGF) receptor II-derived peptides inhibit VEGF,: *The Journal of Biological Chemistry*, 274(9):5612-5619, 1999.

Powell et al., "Peptide stability in drug development. II. Effect of single amino acid substitution and glycosylation on peptide reactivity in human serum," *Pharmaceutical Res.*, 10(9):1268-1273, 1993.

Scott and Smith, "Searching for peptide ligands with an epitope library," *Science*, 249:386-390, 1990.

Tamaskovic et al., "Enzyme-linked immunosorbent assay for the measurement of JNK activity in cell extracts," Biol. Chem, 380:569-578, 1999.

Tan et al., "A small peptide derived from flt-1 (VEGFR-1) functions as an angiogenic inhibitor," *FEBS Letters*, 494:150-156, 2001.

Vigers et al., "X-ray crystal structure of a small antagonistic peptide bound to interleukin-1 receptor type 1," *J. Biol. Chem.*, 275(47):36927-36933, 2000.

Yoon et al., "Antibodies to domains II and III of the IL-1 receptor accessory protein inhibit IL-1β activity but not binding: regulation of IL-1 responses is via type 1 receptor, not the accessory protein," *Journal of Immunology*, 1998.

Zuckermann et al., "Discovery of nanomolar ligands for 7-transmembrane G-protein-coupled receptors from a diverse N-(Substituted) glycine peptoid library," J. Med. Chem, 37:2673-2685, 1994.

* cited by examiner

MQSKVLLAVALWLCVETRAASVGLPSVSLDLPRLSIQKDILTIKANTTLQITCRGQRDLD 60
                                                         ↑
                                                      Ig-like 1

WLWPNNQSGSEQRVEVTECSDGLPCKTLTIPKVIGNDTGAYKCFYRETDLASVIYVYVQD 120

YRSPPIASVSDQHGVVYITENKNKTVVIPCLGSISNLNVSLCARYPEKRFVPDGNRISWD 180
              ↑
           Ig-like 2

SKKGFTIPSYMISYAGMVPCEAKINDESYQSIMYIVVVVGYRIYDVVLSPSEGIELSVGE 240
                                                       ↑
                                                    Ig-like 3

KLVLNCTARTELNVGIDFNWEYPSSKHQHKKLVNRDLKTQSGSEMKKFLSTLTIDGVTRS 300

DQGLYTCAASSGLMTKKNSTFVRVHEKPFVAFGSGMESLV<u>EATVGERVRIPAKYLGYPPP</u> 360
                                              ↑
                                           Ig-like 4

<u>EIKWYKNGIPLESNHTIKAGHVLTIMEVSERDTGNYTVILTNPISKEKQSHVVSLVVYVP</u> 420

<u>PQIGEKSLISPVDSYQYGTTQTLTCTVYAIPPPHHIHWYWQLEEECANEPSQAVSVTNPY</u> 480
                    ↑
                 Ig-like 5

<u>PCEEWRSVEDFQGGNKIEVNKNQFALIEGKNKTVSTLVIQAANVSALYKCEAVNKVGRGE</u> 540

<u>RVISFHVTRGPEITLQPDMQPTEQESVSLWCTADRSTFENLTWYKLGPQPLPIHVGELPT</u> 600
                          ↑
                       Ig-like 6

PVCKNLDTLWKLNATMFSNSTNDILIMELKNASLQDQGDYV<u>CLAQDRKTKKRHCVVRQLT</u> 660

Ig-like 7
                 ↓
<u>VLERVAPTITGNLENQTTSIGESIEV</u>SCTASGNPPPQIMWFKDNETLVEDSGIVLKDGNR 720

Figure 3

NLTIRRVRKEDEGLYTCQACSVLGQAKVEAFFIIEGAQEKTNLEIIILVGTAVIAMFFWL 780

LLVIILRTVKRANGGELKTGYLSIVMDPDELPLDEHCERLPYDASKWEFPRDRLKLGKPL 840

GRGAFGQVIEADAFGIDKTATCRTVAVKMLKEGATHSEHRALMSELKILIHIGHHLNVVN 900

LLGACTKPGGPLMVIVEFCKFGNLSTYLRSKRNEFVPYKTKGARFRQGKDYVGAIPVDLK 960

RRLDSITSSQSSASSGFVEEKSLSDVEEEEAPEDLYKDFLTLEHLICYSFQVAKGMEFLA 1020

SRKCIHRDLAARNILLSEKNVVKICDFGLARDIYKDPDYVRKGDARLPLKWMAPETIFDR 1080

VYTIQSDVWSFGVLLWEIFSLGASPYPGVKIDEEFCRRLKEGTRMRAPDYTTPEMYQTML 1140

DCWHGEPSQRPTFSELVEHLGNLLQANAQQDGKDYIVLPISETLSMEEDSGLSLPTSPVS 1200

CMEEEEVCDPKFHYDNTAGISQYLQNSKRKSRPVSVKTFEDIPLEEPEVKVIPDDNQTDS 1260

GMVLASEELKTLEDRTKLSPSFGGMVPSKSRESVASEGSNQTSGYQSGYHSDDTDTFVYS 1320

SEEAELLKLIEIGVQTGSTAQILQPDSGTTLSSPPV

FIG. 3 continued

MKVLLRLICFIALLISSLEADKCKEREEKIILVSSANEIDVRPCPLNPNEHKGTITWYKD 60
↑
Ig-like domain 1 →

DSKTPVSTEQASRIHQHKEKLWFVPAKVEDSGHYYCVVRNSSYCLRIKISAKFVENEPNL 120

CYNAQAIFKQKLPVAGDGGLVCPYMEFFKNENNELPKLQWYKDCKPLLLDNIHFSGVKDR 180
↑
Ig-like 2 →

LIVMNVAEKHRGNYTCHASYTYLGKQYPITRVIEFITLEENKPTRPVIVSPANETMEVDL 240
↑
Ig-like 3 →

GSQIQLICNVTGQLSDIAYWKWNGSVIDEDDPVLGEDYYSVENPANKRRSTLITVLNISE 300

IESRFYKHPFTCFAKNTHG[DAAYIQLIYPVTNFQKHMIGI]CVTLTVIIVCSVFIYKIFK 360

IDIVLWYRDSCYDFLPIKASDGKTYDAYILYPKTVGEGSTSDCDIFVFKVLPEVLEKQCG 420

YKLFIYGRDDYVGEDIVEVINENVKKSRRLIIILVRETSGFSWLGGSSEEQIAMYNALVQ 480

DGIKVVLLELEKIQDYEKMPESIKFIKQKHGAIRWSGDFTQGPQSAKTRFWKNVRYHMPV 540

QRRSPSSKHQLLSPATKEKLQREAHVPLG 569

FIG. 4

MTLLWCVVSLYFYGILQSDASERCDDWGLDTMRQIQVFEDEPARIKCPLFEHFLKFNYST 60
↑
Ig-like 1 domain →

AHSAGLTLIWYWTRQDRDLEEPINFRLPENRISKEKDVLWFRPTLLNDTGNYTCMLRNTT 120

YCSKVAFPLEVVQKDSCFNSPMKLPVHKLYIEYGIQRITCPNVDGYFPSSVKPTITWYMG 180
↑
Ig-like 2 →

CYKIQNFNNVIPEGMNLSFLIALISNNGNYTCVVTYPENGRTFHLTRTLTVKVVGSPKNA 240

VPPVIHSPNDHVVYEKEPGEELLIPCTVYFSFLMDSRNEVWWTIDGKKPDDITIDVTINE 300
↑
Ig-like 3 →

SISHSRTEDETRTQILSIKKVTSEDLKRS YVCHARSAKGEVAKAAKVKQKVPAPRYTVEL 360
Juxtamembranous

ACGFGATVLL VVILIVVYHVYWLEMVLFYRAHFGTDETILDGKEYDIYVSYARNAEEEEF 420

VLLTLRGVLENEFGYKLCIFDRDSLPGGIVTDETLSFIQKSRRLLVVLSPNYVLQGTQAL 480

LELKAGLENMASRGNINVILVQYKAVKETKVKELKRAKTVLTVIKWKGEKSKYPQGRFWK 540

QLQVAMPVKKSPRRSSSDEQGLSYSSLKNV

FIG. 5

MKSGSGGGSPTSLWGLLPLSAALSLWPTSGEICGPGIDIRNDYQQLKRLENCTVIEGYLH 60

Chaîne α →

ILLISKAEDYRSYRFPKLTVITEYLLLPRVAGLESLGDLFPNLTVIRGWKLFYNYALVIF 120

EMTNLKDIGLYNLRNITRGAIRIKKNADLCYLSTVDWSLILDAVSNNYIVGNKPPKECGD 180

LCPGTMEEKPMCEKTTINNEYNYRCWTTNRCQKMCPSTCGKRACTENNECCHPECLGSCS 240

↑Cyst rich domain →

APDNDTACVACRHYYYAGVCVPACPPNTYRFEGWRCVDRDFCANILSAESSDSEGFVIHD 300

GECMQECPSGFIRNGSQSMYCIPCEGPCPKVCEEEKKTKTIDSVTSAQMLQGCTIFKGNL 360

← Cyst rich domain ↑↑ L2 domain →

LINIRRGNNIASELENFMGLIEVVTGYVKIRHSHALVSLSFLKNLRLILGEEQLEGNYSF 420

YVLDNQNLQQLWDWDHRNLTIKAGKMYFAFNPKLCVSEIYRMEEVTGTKGRQSKGDINTR 480

NNGERASCESDVLHFTSTTTSKNRIIITWHRYRPPDYRDLISFTVYYKEAPFKNVTEYDG 540

← L2 ↑↑ FbnIII-1 →

QDACGSNSWNMVDVDLPPNKDVEPGILLHGLKPWTQYAVYVKAVTLTMVENDHIRGAKSE 600

ILYIRTNASVPSIPLDVLSASNSSSQLIVKWNPPSLPNGNLSYYIVRWQRQPQDGYLYRH 660

← FbnIII-1 ↑↑ FbnIII-2a →

NYCSKDKIPIRKYADGTIDIEEVTENPKTEVCGGEKGPCCACPKTEAEKQAEKEEAEYRK 720

VPE PLHNSIFVPRPH RKRRDVMQVANTTMSSRSRNTTAADTYNITDPEELETEYPFFES 780

Juxtamembranaire α
← Chaîne α / Chaîne β →

RVDNKERTVISNLRPFTLYRIDIHSCNHEAEKLGCSASNFVFARTMPAEGADDIPGPVTW 840

↑FbnIII-2b domain → ← FbnIII-2b ↑↑ FbnIII-3 →

EPRPENSIFLKWPEPENPNGLILMYEIKYGSQVEDQRECVSRQEYRKYGGAKLNRLNPGN 900

YTARIQATSLSGNGSW TDPVFFYVQAKTGYENFIHLIIALPVAVLLI GGLVIMLYVFHR 960

Juxtamembranous β

KRNNSRLGNGVLYASVNPEYFSAADVYVPDEWEVAREKITMSRELGQGSFGMVYEGVAKG 1020

VVKDEPETRVAIKTVNEAASMRERIEFLNEASVMKEFNCHHVVRLLGVVSQGQPTLVIME 1080

```
LMTRGDLKSYLRSLRPEMENNPVLAPPSLSKMIQMAGEIADGMAYLNANKFVHRDLAARN   1140

CMVAKDFTVKIGDFGMTRDIYETDYYRKGGKGLLPVRWMSPESLKDGVFTTYSDVWSFGV   1200

VLWEIATLAEQPYQGLSNEQVLRFVMEGGLLDKPDNCPDMLFELMRMCWQYNPKMRPSFL   1260

EIISSIKEEMEPGFREVSFYYSEENKLPEPEELDLEPENMESVPLDPSASSSSLPLPDRH   1320

SGHKAENGPGPGVLVLRASFDERQPYAHMNGGRKNERALPLPQSSTC               1367
                    ←——————    β Chain
```

FIG. 6

MGWLCSGLLFPVSCLVLLQVASSGNMKVLQEPTCVSDYMSISTCEWKMNGPTNCSTELRL 60
                        ↑ D1 domain (FbnIII-like) →
LYQLVFLLSRAHTCIPENNGGAGCVCHLLMDDVVSADNYTLDLWAGQQLLWKGSFKPSEH 120
                                                    D1 ←      ↑
VKPRAPGNLTVHTNVSDTLLLTWSNPYPPDNYLYNHLTYAVNIWSENDPADFRIYNVTYL 180
↑ D2 domain →
EPSLRIAASTLKSGISYRARVRAWAQCYNTTWSEWSPSTK[WHNSYREPFEQHLLLGVSVS] 240
                                    ← D2 ↑  Juxtamembranous

CIVILAVCLLCYVSITKIKKEWWDQIPNPARSRLVAIIIQDAQGSQWEKRSRGQEPAKCP 300

HWKNCLTKLLPCFLEHNMKRDEDPHKAAKEMPFQGSGKSAWCPVEISKTVLWPESISVVR 360

CVELFEAPVECEEEEEVEEEKGSFCASPESSRDDFQEGREGIVARLTESLFLDLLGEENG 420

GFCQQDMGESCLLPPSGSTSAHMPWDEFPSAGPKEAPPWGKEQPLHLEPSPPASPTQSPD 480

NLTCTETPLVIAGNPAYRSFSNSLSQSPCPRELGPDPLLARHLEEVEPEMPCVPQLSEPT 540

TVPQPEPETWEQILRRNVLQHGAAAAPVSAPTSGYQEFVHAVEQGGTQASAVVGLGPPGE 600

AGYKAFSSLLASSAVSPEKCGFGASSGEEGYKPFQDLIPGCPGDPAPVPVPLFTFGLDRE 660

PPRSPQSSHLPSSSPEHLGLEPGEKVEDMPKPPLPQEQATDPLVDSLGSGIVYSALTCHL 720

CGHLKQCHGQEDGGQTPVMASPCCGCCCGDRSSPPTTPLRAPDPSPGGVPLEASLCPASL 780

APSGISEKSKSSSSFHPAPGNAQSSSQTPKIVNFVSVGPTYMRVS                825

FIG. 7

A
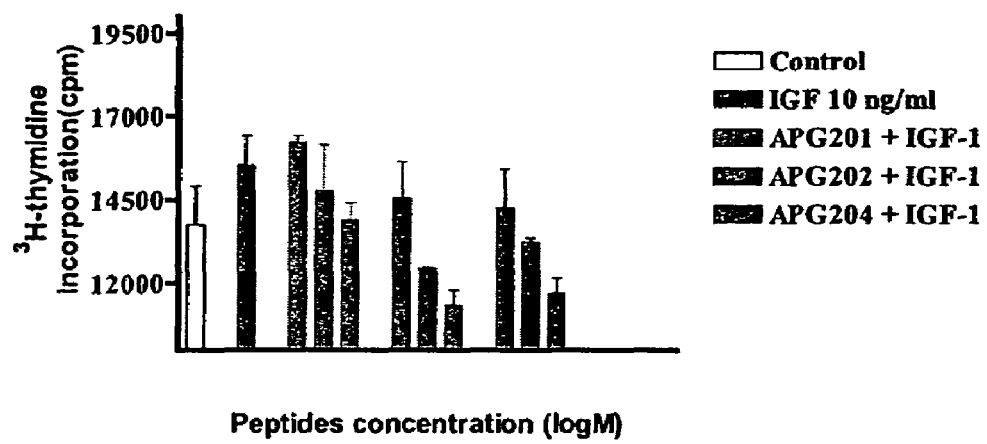
B
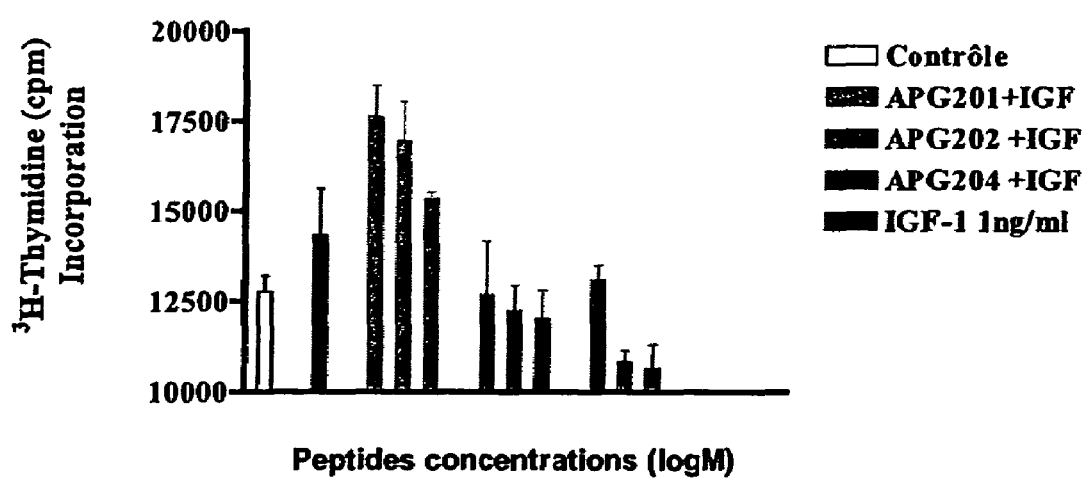
FIG. 8

```
IL1R_HUMAN    ---MKVLLRLICFIALLISSLEADKCKEREEKIILVSSANEIDVRPCP--LNPNEHKG-T
IL1R_MOUSE    MENMKVLLGLICLMVPLLS-LEIDVCTEYPNQIVLFLSVNEIDIRKCP--LTPNKMHGDT
IL1R_RAT      MENMKVLLGFICLIVPLLS-LETDKCTEYPNEVISFSSVNEIDIRSCP--LTPNEMHGGT
IL-1R HORSE   MHKMTSTFLLIGHLILLIPLFSAEECVICN----YFVLVGEPTAISCPVITLPMLHSDYN
                *.  : :*  :   *:. :. : *        . ..*    **   *    . .

IL1R_HUMAN    ITWYKDDSKTPVSTEQASRIHQHKEKLWFVPAKVEDSGHYYCVVRNSSYCLRIKISAKFV
IL1R_MOUSE    IIWYKNDSKTPISADRDSRIHQQNEHLWFVPAKVEDSGYYYCIVRNSTYCLKTKVTVTVL
IL1R_RAT      IIWYKNDSKTPISADKDSRIHQQNEHLWFVPAKMEDSGYYYCIMRNSTYCLKTKITMSVL
IL-1R HORSE   LTWYRNGSNMPITTERRARIHQRKGLLWFIPAALEDSGLYECEVRSLNRSKQKIINLKVF
              : **;:.*: *::::::  :****;;   ***;** :****  * *  :*. . . :. ...

IL1R_HUMAN    ENEPNLCYNAQAIFKQKLPVAGDGGLVCPYMEFFKNENNELPKLQWYKDCKPLLLDN--I
IL1R_MOUSE    ENDPGLCYSTQATFPQRLHIAGDGSLVCPYVSYFKDENNELPEVQWYKNCKPLLLDN--V
IL1R_RAT      ENDPGLCYNTQASFIQRLHVAGDGSLVCPYLDFFKDENNELPKVQWYKNCKPLPLDD--G
IL-1R HORSE   KNDNGLCFNGEMKYDQIVKSANAGKIICPDLENFKDEDNINPEIHWYKECKSGFLEDKRL
              :*: .**:. :     : *. * ::**  :. **:*:*  *::;***:**. *::

IL1R_HUMAN    HFSGVKDRLIVMNVAEKHRGNYTCHASYTYLGKQYPITRVIEFITLEENKPTRPVIVSPA
IL1R_MOUSE    SFFGVKDKLLVRNVAEEHRGDYICRMSYTFRGKQYPVTRVIQFITIDENKRDRPVILSPR
IL1R_RAT      NFFGFKNKLMVMNVAEEHRGNYTCRTSYTYQGKQYPVTRVITFITIDDSKRDRPVIMSPR
IL-1R HORSE   VLAEGENAILILNVTIQDKGNYTCRMVYTYMGKQYNVSRTMNLEVKESPLKMRPEFIYPN
              :   :: ::: **: :.:*;* *:   **: **** ::*.:  :  . :.    ** :: *

IL1R_HUMAN    NETMEVDLGSQIQLICNVTG-QLSDIAYWKWNGSVIDEDDPVLGEDYYSVENPANKRRST
IL1R_MOUSE    NETIEADPGSMIQLICNVTG-QFSDLVYWKWNGSEIEWNDPFLAEDYQFVEHPSTKRKYT
IL1R_RAT      NETMEADPGSTIQLICNVTG-QFTDLVYWKWNGSEIEWDDPILAEDYQFLEHPSAKRKYT
IL-1R HORSE   NNTIEVELGSHVVMECNVSSGVYGLLPYWQVNDEDVDSFDSTYREQFYEEGMPHG--IAV
              *:*:*..: ** : : ***:.   : **: *..  :: *.  *:: *

IL1R_HUMAN    LITVLNISEIESRFYKHPFTCFAKNTHGIDAAYIQLIYPVTNFQKHMIGICVTLTVIIVC
IL1R_MOUSE    LITTLNISEVKSQFYRYPFICVVKNTNIFESAHVQLIYPVPDFKNYLIGGFIILTATIVC
IL1R_RAT      LITTLNVSEVKSQFYRYPFICFVKNTHILETAHVRLVYPVPDFKNYLIGGFAIFTATAVF
IL-1R HORSE   SGTKFNISEVKLKDYAYKFFCHFIYDSQEFTSYIKLEHPVQNIRGYLIGGGISLIFLLFL
               * :*:**:: : * : *        ::::;:* :**  ::: :;**     :

IL1R_HUMAN    SVFIYKIFKIDIVLWYRDSCYDFLPIKASDGKTYDAYILYPKTVGEGSTSDCDIFVFKVL
IL1R_MOUSE    CVCIYKVFKVDIVLWYRDSCSGFLPSKASDGKTYDAYILYPKTLGEGSFSDLDTFVFKLL
IL1R_RAT      CACIYKVFKVDIVLWYRDSCSDFLPRKASDGRTYDAYVLYPKTYGEGSFAYLDTFVFKLL
IL-1R HORSE   ILIVYKIFKIDIVLWYRSSCHPLLGKKVSDGKIYDAYVLYPKNR-ESCLYSSDIFALKIL
              :**:**:******.** :*  *.***: ****:****. *..    * *.:*;*

IL1R_HUMAN    PEVLEKQCGYKLFIYGRDDYVGEDIVEVINENVKKSRRLIIILVRETSGFSWLGGSSEEQ
IL1R_MOUSE    PEVLEGQFGYKLFIYGRDDYVGEDTIEVTNENVKKSRRLIIILVRDMGGFSWLGQSSEEQ
IL1R_RAT      PEVLEGQFGYKLFICGRDDYVGEDTIEVTNENVKRSRRLIIILVRDMGSFSCLGQSSEEQ
IL-1R HORSE   PEVLERQCGYNLFIFGRNDLAGEAVIDVTDEKIHQSRRVIIILVPEPSCYGILEDASEKH
              ***** * **;*** **:* .**  ::* :*:::;***:*****  ;  :. *  :**::

IL1R_HUMAN    IAMYNALVQDGIKVVLLELEKIQDYEKMPESIKFIKQKHGAIRWSGDFTQGPQSAKTRFW
IL1R_MOUSE    IAIYNALIQEGIKIVLLELEKIQDYEKMPDSIQFIKQKHGVICWSGDFQERPQSAKTRFW
IL1R_RAT      IAIYDALIREGIKIILLELEKIQDYEKMPESIQFIKQKHGAICWSGDFKERPQSAKTRFW
IL-1R HORSE   LAVYNALIQDGIKIILIELEKIEDYANMPESIKYVKQKYGAIRWTGDFSERSHSASTRFW
              :*:*:**::;:;***;:*****:**.**  :*:**::***:.* *:***  :.:**.****

IL1R_HUMAN    KNVRYHMPVQRRSPSSKHQLLSP----ATKEKLQREAHVPLG
IL1R_MOUSE    KNLRYQMPAQRRSPLSKHRLLTLDPVRDTKEKLPAATHLPLG
IL1R_RAT      KNLRYQMPAQRRSPLSKHHLLTLDPVLDTKEKLQAETHLPLG
IL-1R HORSE   KKVRYHMPSRKHGSSSGFHLSS--------------------
              *;;**:** :::.. * ..:* :
```

FIGURE 11

```
IL4R_HUMAN   MGWLCSGLLFPVSCLVLLQVASSGNMKVLQEPTCVSDYMSISTCEWKMNGPTNCSTELRL
IL4R_MOUSE   MGRLCTKFLTSVGCLILLLVTGSGSIKVLGEPTCFSDYIRTSTCEWFLDSAVDCSSQLCL
IL-4R HORSE  MGRLCTKFLTSVGCLILLLVTGSGSIKVLGEPTCFSDYIRTSTCEWFLDSAVDCSSQLCL
             ** **: :* .*.**:** *:.**.:*** ****.***:  *****  ::...:**::* *

IL4R_HUMAN   LYQLVFLLS-EAHTCIPENNGGAGCVCHLLMDDVVSADNYTLDLWAGQQLLWKGSFKPSE
IL4R_MOUSE   HYRLMFFEFSENLTCIPRNSASTVCVCHMEMNRPVQSDRYQMELWAEHRQLWQGSFSPSG
IL-4R HORSE  HYRLMFFEFSENLICIPRNSASTVCVCHMEMNRPVQSDRYQMELWAEHRQLWQGSFSPSG
              *:*:*:   * ***.*...: ****: *: *.:*.* ::*** ::  **:***.**

IL4R_HUMAN   HVKPRAPGNLTVHTNVSDTLLLTWSNPYPPDNYLYNHLTYAVNIWSENDPADFRIYNVTY
IL4R_MOUSE   NVKPLAPDNLTLHTNVSDEWLLTWNNLYPSNNLLYKDLISMVNISREDNPAEFIVYNVTY
IL-4R HORSE  NVKPLAPDNLTLHTNVSDEWLLTWNNLYPSNNLLYKDLISMVNISREDNPAEFIVYNVTY
             :*** **.***:****** ****.* **.:* **:.*   *** *::**:* :*****

IL4R_HUMAN   LEPSLRIAASTLKSGISYRARVRAWAQCYNTTWSEWSPSTKWHNSYREPFEQHLLLGVSV
IL4R_MOUSE   KEPRLSFPINILMSGVYYTARVRVRSQILTGTWSEWSPSITWYNHFQLPLIQRLPLGVTI
IL-4R HORSE  KEPRLSFPINILMSGVYYTARVRVRSQILTGTWSEWSPSITWYNHFQLPLIQRLPLGVTI
              ** * :. . * **: * ****. :*  . ******** .*:* ::  *: *:* ***::

IL4R_HUMAN   SCIVILAVCLLCYVSITKIKKEWWDQIPNPARSRLVAIIQDAQGSQWEKRSRGQEPAKC
IL4R_MOUSE   SCLCIPLFCLFCYFSITKIKKIWWDQIPTPARSPLVAIIIQDAQVPLWDKQTRSQESTKY
IL-4R HORSE  SCLCIPLFCLFCYFSITKIKKIWWDQIPTPARSPLVAIIIQDAQVPLWDKQTRSQESTKY
             **: *  .**:**.******* ******.**** ********** .  *:*:.*.**.:*

IL4R_HUMAN   PHWKNCLTKLLPCFLEHNMKRDEDPHKAAKEMPFQGSGKSAWCPVEISKTVLWPE--SIS
IL4R_MOUSE   PHWKTCLDKLLPCLLKHRVKKKTDFPKAAPTKSLQSPGKAGWCPMEVSRTVLWPENVSVS
IL-4R HORSE  PHWKTCLDKLLPCLLKHRVKKKTDFPKAAPTKSPQSPGKAGWCPMEVSRTVLWPENVSVS
             ****.** *****:*:*.:*::. *  ***   . *.**:.***:*:*:****** *:*

IL4R_HUMAN   VVRCVELFEAPVECEEEEEVEEEKGSFCASPESSRDD-FQEGREGIVARLTESLFLDLLG
IL4R_MOUSE   VVRCMELFEAPVQNVEEEEDEIVKEDLSMSPENSGGCGFQESQADIMARLTENLFSDLLE
IL-4R HORSE  VVRCMELFEAPVQNVEEEEDEIVKEDLSMSPENSGGCGFQESQADIMARLTENLFSDLLE
             ****:*******: ****  *  * .:. ***.*  . ***.: .*:*****.** ***

IL4R_HUMAN   EENGGFCQQDMGESCLLPPSGSTSAHMPWDEFPSAGPKEAPPWGKEQPLHLEPSPPASPT
IL4R_MOUSE   AENGGLGQSALAESCSPLPSGSGQASVSWACLPMGPSEEATCQVTEQPSHPGPLS-GSPA
IL-4R HORSE  AENGGLGQSALAESCSPLPSGSGQASVSWACLPMGPSEEATCQVTEQPSHPGPLS-GSPA
             ****: *. :.*** ****  .* :.* :* . . .:**.   .***    *  .**:

IL4R_HUMAN   QSPDNLTCTETPLVIAGNPAYRSFSNSLSQSPCPRELGPDPLLARHLEEVEPEMPCVPQL
IL4R_MOUSE   QSPAPTLACTQVPLVLADNPAYRSFSDCCSPAPNPGELAPEQQQADHLEEEEPPSPADPHS
IL-4R HORSE  QSPAPTLACTQVPLVLADNPAYRSFSDCCSPAPNPGELAPEQQQADHLEEEEPPSPADPHS
             ***.  .*:**:.***:*.********:. * :* * **.*:    * **** **  *. *:

IL4R_HUMAN   SEPTTVPQPEPETWEQILRRNVLQHGAAAAPVSAPTSGYQEFVHAVEQGGTQASAVVGLG
IL4R_MOUSE   SGPPMQP---VESWEQILHMSVLQHGAAAGSTPAPAGGYQEFVQAVKQGAAQDPGVPGVR
IL-4R HORSE  SGPPMQP---VESWEQILHMSVLQHGAAAGSTPAPAGGYQEFVQAVKQGAAQDPGVPGVR
             * *.  *   *:*****:.   *********....**:.******:**:**:**.:*  ..* *:

IL4R_HUMAN   PPGEAGYKAFSSLLASSAVSPEKCGFGASSGEEGYKPFQDLIPGCPGDPAPVPVPLFTFG
IL4R_MOUSE   PSGDPGYKAFSSLLSSNGIRGDTAAAGTDDGHGGYKPFQNPVP----NQSPSSVPLFTFG
IL-4R HORSE  PSGDPGYKAFSSLLSSNGIRGDTAAAGTDDGHGGYKPFQNPVP----NQSPSSVPLFTFG
             *.*:.*********:*...:   :... *:...*.  ******:  :*    : :* .*******

IL4R_HUMAN   LDREPPRSPQSSHLPSSSPEHLGLEPGEKVEDMPKPPLPQEQATDPLVDSLGSGIVYSAL
IL4R_MOUSE   LDTELSPSPLNSDPPKSPPECLGLELGLKGGDWVKAPPPADQVPKPFGDDLGFGIVYSSL
IL-4R HORSE  LDTELSPSPLNSDPPKSPPECLGLELGLKGGDWVKAPPPADQVPKPFGDDLGFGIVYSSL
             ** * . ** .* *.*.** **** * *  *.*   :*...*:  *:.** *****.*

IL4R_HUMAN   TCHLCGHLKQCHGQEDGGQTPVMASPCCGCCCGDRSSPPTTPLRAPDPSPGGVPLEASLC
IL4R_MOUSE   TCHLCGHLKQHHSQEEGGQSPIVASPGCGCCYDDRSPSLGSLSGALESCPEGIPPEANLM
IL-4R HORSE  TCHLCGHLKQHHSQEEGGQSPIVASPGCGCCYDDRSPSLGSLSGALESCPEGIPPEANLM
             **********  *.**:***::::*** **** .***..   :     * :..* *:* **.*

IL4R_HUMAN   PASLAPSGISEKSKSSSSFHPAPGNAQSSSQTPKIVNFVSVGPTYMRVS
IL4R_MOUSE   SAPKTPSNLS----------GEGKGPGHSPVPSQTTEVPVGALGIAVS
IL-4R HORSE  SAPKTPSNLS----------GEGKGPGHSPVPSQTTEVPVGALGIAVS
             .*. :**.:*            *:..* .*..*.* ..  *.**.  : **
```

Figure 12

```
VGR2_HUMAN    MQSKVLLAVALWLCVETRAASVGLPSVSLDLPRLSIQKDILTIKANTTLQITCRGQRDLD
VGR2_MOUSE    MESKALLAVALWFCVETRAASVGLPGDFLHPPKLSTQKDILTILANTTLQITCRGQRDLD
VGR2_RAT      MESRALLAVALWFCVETRAASVGLPGDSLHPPKLSTQKDILTILANTTLQITCRGQRDLD
VGR2_QUAIL    ---MELGPLRVLTVLLCLAPVFAGLFISMDQPTLSIQKSVLTITTNDTLNITCSGQRAVY
                 *  .: :   :   *. ..     :.  * ** **.:***  :* **;*** ***  :

VGR2_HUMAN    WLWPNNQSGSEQRVEVTECS--DGLFCKTLTIPKVIGNDTGAYKCFYRETDLASVIYVYV
VGR2_MOUSE    WLWPNAQRDSEERVLVTECGGGDSIFCKTLTIPRVVGNDTGAYKCSYRDVDIASTVYVYV
VGR2_RAT      WLWPNTPRDSEERVLVTECG--DSIFCKTLTVPRVVGNDTGAYKCFYRDTDVSSIVYVYV
VGR2_QUAIL    WSWPNNQSSVEKRLAVTGCS--EGPFCKTLTLLRVIGNDTGDYRCLYGDSQAATTIYVYV
              * ***        . *:*: ** *.  :. ******: :*:**** *:*  *  :  :  :: :****

VGR2_HUMAN    QDYRSPFIASVSDQHGVVYITENKNKTVVIPCLGSISNLNVSLCARYPEKRFVPDGNRIS
VGR2_MOUSE    RDYRSPFIASVSDQHGIVYITENKNKTVVIPCRGSISNLNVSLCARYPEKRFVPDGNRIS
VGR2_RAT      QDHRSPFIASVSDEHGIVYITENKNKTVVIPCRGSISNLNVSLCARYPEKRFVPDGNRIS
VGR2_ QUAIL   QDYRSPFVTSVGDQLGIVYITKN--KTVVVPCLGTVSNLNVSLHAKYPEKVFVPDGKSIS
              :*:****::**.*: *:****:*   ****:** *::*******  *:****  *****: **

VGR2_HUMAN    WDSKKGFTIPSYMISYAGMVFCEAKINDESYQSIMYIVVVVGYRIYDVVLSPSHGIELSV
VGR2_MOUSE    WDSEIGFTLPSYMISYAGMVFCEAKINDETYQSIMYIVVVVGYRIYDVILSPPHEIELSA
VGR2_RAT      WDSEKGFTIPSYMISYAGMVFCEAKINDETYQSIMYIVLVVGYRIYDVVLSPPHEIELSA
VGR2_QUAIL    WDNKKGFTIPSHLINYAGMVFCEAKIDNESYQSVIYIVAVVGYRIYDLTMNPHYQVELAV
              **.:  ***:**::*.***********:*;***;:*** ********;  :.*  :  :**:.

VGR2_HUMAN    GEKLVLNCTARTELNVGIDFNWEYPSSKHQHKKLVNRDLKTQSGSEMKKFLSTLTIDGVT
VGR2_MOUSE    GEKLVLNCTARTELNVGLDFTWHSPPSKSHHKKIVNRDVKPFPGTVAKMFLSTLTIESVT
VGR2_RAT      GEKLVLNCTARTELNVGLDFSWQFPSSKHQHKKIVNRDVKSLPGTVAKMFLSTLTIDSVT
VGR2_QUAIL    GEKLVLNCTVRTELNVGIDFRWDYPSIKERRATIRDLKTTAG---EIKTFVSTLTIESVN
              *********.*******:** *. *. *  :: .: :  ..    *  *;:*****;.*.

VGR2_HUMAN    RSDQGLYTCAASSGLMTKKNSTFVRVHEKPFVAFGSGMESLVEATVGERVRIPAKYLGYP
VGR2_MOUSE    KSDQGEYTCVASSGRMIKRNRTFVRVHTKPFIAFGSGMKSLVEATVGSQVRIPVKYLSYP
VGR2_RAT      KSDQGEYTCTAYSGLMTKKNKTFVRVHTKPFIAFGSGMKSLVEATVGSQVRIPVKYLSYP
VGR2_QUAIL    LSDKGRYTCAASSGRMNMKNSSYPIIHESPFIHLEK-MENVVEMKLGDTVSIPVKFKGYP
              **:*  ***.*  ** *   :* :;. :* .**:  :  .  *;.:** .;*. * **.*; .**

VGR2_HUMAN    PPEIKWYKNGIPLESNHTIKAGHVLTIMEVSERDTGNYTVILTNPISKEKQSHVVSLVVY
VGR2_MOUSE    APDIKWYRNGRPIESNYTMIVGDELTIMEVTERDAGNYTVILTNPISMEKQSHMVSLVVN
VGR2_RAT      APDIKWYRNGRPIESNYTMIVGDELTIMEVSERDAGNYTVILTNPISMEKQSHMVSLVVN
VGR2_QUAIL    PPEAKWYKNGKVINANHTVKLGYALVITEATEKDAGNYTVVLTNPTNKMQKRHTFTLLVN
              .*: ***:**   :::*:*:  *  *.* *.:;*;*;*****:****  .  ::  * ..;*:*

VGR2_HUMAN    VPPQIGEKSLISPVDSYQYGTTQTLTCTVYAIPPPHHIHWYWQLEEECANEPSQAVSVTN
VGR2_MOUSE    VPPQIGEKALISPMDSYQYGTMQTLTCTVYANPPLHHIQWYWQLEEACSYRPG----QTS
VGR2_RAT      VPPQIGEKALISPMDSYQYGTMQTLTCTVYANPPLHHIQWYWQLEEACSYRPS----QTN
VGR2_QUAIL    VPPQIGENALMAPVDSYKYGSTQALTCTIYAVPPPAAVLWYWQLEEECTFSPQKVRLGAN
              *******::.*;;*;***;**; *;****;** **   : *******  *:   *      :.

VGR2_HUMAN    PYPCEEWRSVEDFQGGNKIEVNKNQFALIEGKNKTVSTLVIQAANVSALYKCEAVNKVGR
VGR2_MOUSE    PYACKEWRHVEDFQGGNKIEVTKNQYALIEGKNKTVSTLVIQAANVSALYKCEAINKAGR
VGR2_RAT      PYTCKEWRHVKDFQGGNKIEVTKNQYALIEGKNKTVSTLVIQAAYVSALYKCEAINKAGR
VGR2_QUAIL    PYACRKWKVISERKGGNQVEIKQR-VVTIAGKTKTVSTLVIQAANVSALYRCMATNRAGS
              **.*.:*: :.: :***::*:.:.   . * **.***********; *****:*  *;.*

VGR2_HUMAN    GERVISFHVTRGPEITLQPDMQPTEQESVSLWCTADRSTFENLTWYKLGPQPLPIHVGEL
VGR2_MOUSE    GERVISFHVIRGPEITVQPAAQPTEQESVSLLCTADRNTFENLTWYKLGSQATSVHMGES
VGR2_RAT      GERVISFHVIRGPEITVQPATQPTERESMSLLCTADRNTFENLTWYKLGSQATSVHMGES
VGR2_QUAIL    SERVISFHVTRGLEINLQPRSQLTEKDNTSLQCTADKFTFEKLSWYKLSTHVSQTPFGGL
              .******** ** **.:**  * **:. ** ****; ***:***;*;****..;     .*

VGR2_HUMAN    PTPVCKNLDTLWKLNATMFSN-STNDILIMELKNASLQDQGDYVCLAQDRKTKKRHCVVR
VGR2_MOUSE    LTPVCKNLDALWKLNGTMFSN-STNDILIVAFQNASLQDQGDYVCSAQDKKTKKRHCLVK
VGR2_RAT      LTPVCKNLDALWKLNGTVFSN-STNDILIVAFQNASLQDQGNYVCSAQDKKTKKRHCLVK
VGR2_QUAIL    PMPVCKNLDALQKLNATVSNVNGENVTLELILRNISLQDGGDYVCIAQDKKKAKTQHCLVK
              *******.* ***.*: .  *     *  *  : ;:****  **;*;*.:***;*;*;:**;*:
```

Figure 13

```
VGR2_HUMAN    QLTVLERVAPTITGNLENQTTSIGESIEVSCTASGNPPPQIMWFKDNETLVEDSGIVLKD
VGR2_MOUSE    QLIILERMAPMITGNLENQTTTIGETIEVTCPASGNPTPHITWFKDNETLVEDSGIVLRD
VGR2_RAT      QLVILERMAPMITGNLENQTTTIGETIEVVCPTSGNPTPLITWFKDNETLVEDSGIVLKD
VGR2_QUAIL    HLTVQEPLHPRLVGNLENQTTNIGETIEVLCTVNGVPPPNITWFKNSETLFEDSGIVLKD
              :*  : *  :    * :.*******.***:***  *...* *.* * ***:.***.*******:*

VGR2_HUMAN    GNRNLTIRRVRKEDEGLYTCQACSVLGCAKVEAFFIIEGAQEKTNLEIIILVGTAVIAMF
VGR2_MOUSE    GNRNLTIRRVRKEDGGLYTCQACNVLGCARAETLFIIEGAQEKTNLEVIILVGTAVIAMF
VGR2_RAT      GNRNLTIRRVRKEDGGLYTCQACNVLGCARAETLFIIEGVQEKTNLEVIILVGTAVIAMF
VGR2_QUAIL    GNKTLTIRRVRKEDGGLYTCLACNILGCKKAEAFFSVQGAEEKTNLELIILVGTAVIAMF
              **:.********* ***** **.:***  :..*;:*  ::*.:******:**********

VGR2_HUMAN    FWLLLVIILRTVKRANGGELKTGYLSIVMDPDELPLDEHCERLPYDASKWEFPRDRLKLG
VGR2_MOUSE    FWLLLVILVRTVKRANEGELKTGYLSIVMDPDELPLDERCERLPYDASKWEFPRDRLKLG
VGR2_RAT      FWLLLVILVRTVKRANEGELKTGYLSIVMDPDELPLDERCERLPYDASKWEFPRDRLKLG
VGR2_QUAIL    FWLLLVIILRTVKRANGGDMKTGYLSIIMDPDEVPIDEHCERLPYDASKWEFPRDRLKLG
              ******.:******* *::*******:*****.*:**:**:**********************

VGR2_HUMAN    KPLGRGAFGQVIEADAFGIDKTATCRTVAVKMLKEGATHSEHRALMSELKILIHIGHHLN
VGR2_MOUSE    KPLGRGAFGQVIEADAFGIDKTATCKTVAVKMLKEGATHSEHRALMSELKILIHIGHHLN
VGR2_RAT      KPLGRGAFGQVIEADAFGIDKTATCKTVAVKMLKEGATHSEHRALMSELKILIHIGHHLN
VGR2_QUAIL    KPLGRGAFGQVIEADAFGIDKTATCRTVAVKMLKEGATHSEHRALMSELKILIHIGHHLN
              *************************:**********************************

VGR2_HUMAN    VVNLLGACTKPGGPLMVIVEFCKFGNLSTYLRSKRNEFVPYKTKGARFRQGKD-YVGAIP
VGR2_MOUSE    VVNLLGACTKPGGPLMVIVEFSKFGNLSTYLRGKRNEFVPYKSKGARFRQGKD-YVGELS
VGR2_RAT      VVNLLGACTKPGGPLMVIVEFCKFGNLSTYLRGKRNEFVPYKSKGARFRSGKD-YVGELS
VGR2_QUAIL    VVNLLGACTKPGGPLMVIVEYCKFGNLSAYLRSKRSEFIPYKMKSARFRQGKENYTGDIS
              ********************:.******:***.***.**.**:***  *.****.**:  *.*   :.

VGR2_HUMAN    VDLKRRLDSITSSQSSASSGFVEEKSLSDVEEEEAP-EDLYKDFLTLEHLICYSFQVAKG
VGR2_MOUSE    VDLKRRLDSITSSQSSASSGFVEEKSLSDVEEEEAS-EELYKDFLTLEHLICYSFQVAKG
VGR2_RAT      VDLKRRLDSITSSQSSASSGFVEEKSLSDVEEEEAS-EELYKDFLTLEHLICYSFQVAKG
VGR2_QUAIL    TDLKQRLDSITSSQSSTSSGFVEERSLSDVEEEDAGSEDLCKNPLTMEDLICYSFVARG
              .***:***********:*******:********:*    *:*  *:  **:*.*********:*

VGR2_HUMAN    MEFLASRKCIHRDLAARNILLSEKNVVKICDFGLARDIYKDPDYVRKGDARLPLKWMAPE
VGR2_MOUSE    MEFLASRKCIHRDLAARNILLSEKNVVKICDFGLARDIYKDPDYVRKGDARLPLKWMAPE
VGR2_RAT      MEFLASRKCIHRDLAARNILLSEKNVVKICDFGLARDIYKDPDYVRKGDPRLPLKWMAPE
VGR2_QUAIL    MEFLASRKCIHRDLAARNILLSDNNVVKICDFGLARDIYKDPDYVRKGDARLPLKWMAPE
              **********************::*************************************.**********

VGR2_HUMAN    TIFDRVYTIQSDVWSFGVLLWEIFSLGASPYPGVKIDEEFCRRLKEGTRMRAPDYTTPEM
VGR2_MOUSE    TIFDRVYTIQSDVWSFGVLLWEIFSLGASPYPGVKIDEEFCRRLKEGTRMRAPDYTTPEM
VGR2_RAT      TIFDRIYTIQSGVWSFGVLLWEIFSLGASPYPGVKIDEKFCRRLKEGTRMRAPDYTTPEM
VGR2_QUAIL    TIFDRVYTIQSDVWSFGVLLWEIFSLGASPYPGVKIDEEFCRRLKEGTRMRAPDYTTPEM
              *****:*****.***********************************:.**********************

VGR2_HUMAN    YQTMLDCWHGEPSQRPTFSELVEHLGNLLQANAQQDGKDYIVLPISETLSMEEDSGLSLP
VGR2_MOUSE    YQTMLDCWHEDPNQRPSFSELVEHLGNLLQANAQQDGKDYIVLPMSETLSMEEDSGLSLP
VGR2_RAT      YQTMLDCWHEDPNQRPAFSELVEHLGNLLQANAQQDGKDYIVLPMSETLSMEEDSGLSLP
VGR2_QUAIL    YQTMLDCWHGDPKQRPTFSELVEHLGNLLQANVRQDGKDYVVLPLSVSLNMEEDSGLSLP
              ********* :*.***:***************..:******:***:*  :*.**********

VGR2_HUMAN    TSPVSCMEEEEVCDPKFHYDNTAGISQYLQNSKRKSRPVSVKTFEDIPLEEPEVKVIPDD
VGR2_MOUSE    TSPVSCMEEEEVCDPKFHYDNTAGISHYLQNSKRKSRPVSVKTFEDIPLEEPEVKVIPDD
VGR2_RAT      TSPVSCMEEEEVCDPKFHYDNTAGISHYLQNSKRKSRPVSVKTFEDIPLEEPEVKVIPDD
VGR2_QUAIL    TSPASCKEEEEVCDPKFHYDNTAGISQYRQGSKRKSRPVSVKTFEDIPLVTT-VKVVQEE
              ***.** ******************:*  *.*****************   . ***:  ::

VGR2_HUMAN    NQTDSGMVLASEELKTLEDRTK-LSPSFGGMVPSKSRESVASEGSNQTSGYQSGYHSDDT
VGR2_MOUSE    SQTDSGMVLASEELKTLEDRNK-LSPSFGGMMPSKSRESVASEGSNQTSGYQSGYHSDDT
VGR2_RAT      SQTDSGMVLASEELKTLEDRNK-LSPSFGGMMPSKSRESVASEGSNQTSGYQSGYHSDDT
VGR2_QUAIL    NQTDSGMVLASEELKTLEEQDKQVKIPFSTLAPSKSNESVMSEASNQTSGYQSGYHSDDM
              .****************:::  *  :.. .*.  :  ****.***  **.************
```

Figure 13 (continued)

```
VGR2_HUMAN      DTTVYSSEEAELLKLIEIGVQTGSTAQILQPDSGTTLSSPPV-------------
VGR2_MOUSE      DTTVYSSDEAGLLKMVDAAVHADSGTTLQLTSCLNGSGPVPAPPPTPGNHERGAA
VGR2_RAT        DTTVYSSDEAGLLKLVDVAGHVDSGTTLRSSPV----------------------
VGR2_QUAIL      DNMVCSSEDTELLCAQEASPTLPRCAWPGIYSPAPVASLPL--------------
                *. * **::: **       :  .         :
```

Figure 13 (continued)

CYTOKINE RECEPTOR MODULATORS AND METHOD OF MODULATING CYTOKINE RECEPTOR ACTIVITY

This application claims the benefit of U.S. Provisional Application No. 60/420,679, filed Oct. 24, 2002, and U.S. Provisional Application No. 60/423,530, filed Nov. 5, 2002. The entire text of the above provisional applications are specifically incorporated by reference.

FIELD OF THE INVENTION

The present invention relates to cytokine receptor agonists and antagonists, to a method of identifying same, and to a method of modulating cytokine receptors activity with same. More specifically, the present invention is concerned with extracellular, non-competitive cytokine receptor modulators, a method of identifying same, their identification and their uses. More particularly, the present invention is concerned with extracellular, non-competitive cytokine receptor antagonists, a method of identifying same, their identification and their therapeutic uses.

BACKGROUND OF THE INVENTION

Cytokines are generic terms for designating biologically active hormone-like proteins (interleukins, interferons, tumor necrosis factor, growth factors) that mediate their effects through a superfamily of receptors. Cytokines and their receptors constitute a powerful control network by which cells signal and coordinate cell proliferation and differentiation, cell death and survival. Cytokines are low molecular weight peptides having very potent biological activity. Their mechanism of action is generally autocrine and paracrine and act by ultimately regulating gene expression.

Cytokines and their receptors are thus implicated in major diseases. They regulate hematopoiesis, immunity and development of the nervous system. Most of all, they contribute to the development of afflictions such as cancer, inflammatory and autoimmune reactions, asthma, allergy, thrombosis, vascular diseases and septic shock by influencing aberrant or overexpressing genes leading to diseases. Cytokines and growth factors mediate tightly regulated biological effects in order to ensure proper control and functioning of the immune system. Therefore, cytokines are also involved in pathological conditions such as inflammation (e.g. rhumatoid arthritis) and tissue degeneration. Diseases which may develop or progress as a result of defects in cytokine or growth factor mediated cell signaling have a high prevalence in the population and are associated with significant morbidity and/or mortality. For these reasons cytokine receptors are important therapeutic target.

The treatments available for these pathologies are currently limited. They often result in high toxicity and secondary effects. The demand in the medical world for safer and more targeted therapies is therefore considerable.

The current approaches in the field of cytokines antagonists include the development of soluble receptors, monoclonal antibodies directed against cytokines, mimetics of cytokines, antisense techniques and kinases inhibitors. Few of these strategies have been successful in drug development, however. Nevertheless, certain antibodies targeting the ligand and the receptor, natural soluble receptor inhibitors (eg. IL1ra), and decoy soluble receptors have displayed interesting results. For instance, Trastuzumab (Herceptin, Roche) a monoclonal antibody which binds the HER-2/neu protein tyrosine kinase, and ZD1839 (Iressa, Astra-Zeneca), a small molecule which binds the EGF receptor are either in clinical trials or available for the treatment of certain diseases.

Non competitive antagonists of cytokines have also been described. In international application no. WO 93/14781 published in 1993, Fox describes the use of non-competitive peptides targeting intracellular domains of EGF. Intracellular domains are difficult to reach by peptides because of the barrier that the cell membrane constitutes.

Antagonists of the prior art are thus either competitive (e.g. soluble receptors, antibodies, cytokine mimetics), not very selective (e.g. tyrosine kinase inhibitors), costly to produce or difficult to apply in vivo (e.g. antisense). Because the ligand exceeds by far the concentration of the receptor, the concentration of competitive antagonists needed to inhibit the receptor is often substantial.

There is therefore a need for non-competitive, selective, extracellular and simple to identify, select and produce antagonists of cytokines.

The present invention seeks to meet these needs and other needs.

The present description refers to a number of documents, the content of which is herein incorporated by reference in their entirety.

SUMMARY OF THE INVENTION

The present invention thus concerns non-competitive and selective extracellular cytokine receptor modulators, and methods of selecting and of using same.

The peptides, derivatives and peptidomimetics thereof of the present invention are derived from selected cytokine receptor flexible regions. Cytokine receptor agonists or antagonists of the present invention possess a unique mechanism and site of action for inhibiting cytokine receptors activity. They are peptides strategically positioned on at least one of an extracellular flexible region including juxtamembranous regions, flexible regions between domains of the cytokine receptor, and oligomerization site, that are important for the appropriate conformation of the receptor which enables signaling. In one embodiment the flexible region is required for proper oligomerization to occur. In such an embodiment, appropriate conformation of the receptor is needed to allow adequate positioning of the protein chains to enable oligomerization of the receptor and its resulting activation.

Cytokine receptors subfragments or peptides of this invention may promote or stabilize a particular conformation of the cytokine receptor which results in inhibition or activation of the receptor activity. In particular, the antagonists of this invention do not necessarily interfere directly with the oligomerization site. They may, for example, exert their antagonistic activity by directly or indirectly preventing the oligomerization of the complementary protein chains (of homodimers as well as heterodimers receptors) of the extracellular domain of the cytokine receptor. This process effectively prevents activation of the intracellular receptor domains responsible for cytokine enzymatic function. Subsequent cell transduction events leading to overexpression of the ligand and/or cell bound receptors responsible in part for disease expression are thereby prevented.

In the alternative, one can use cytokine receptors subfragment peptides or derivatives to promote or stabilize the active cytokine receptor structure capable signal transduction. Such peptides are considered agonists of the present invention. Cytokine receptor modulators of the present invention possess a number of advantages over the prior art.

Because they have extracellular targets, unlike certain known drug candidates which target intracellular regions of the cytokine receptors, the antagonists of the present invention do not necessitate a prior permeabilization or other disruption of cell membranes to gain access to the target in order to produce a pharmacological response.

Because they are non competitive, a smaller amount of the antagonists of the present invention is necessary to inhibit the receptor that they target, as compared to competitive inhibitors.

As peptides, the antagonists of the present invention are advantageously simple to synthesize.

In order to provide a clear and consistent understanding of terms used in the present description, a number of definitions are provided herein below.

In view of the importance of the function of cytokine receptors in numerous pathway and conditions in animals, the present invention has broad impact on the screening, identification, validation and treatment of conditions or diseases associated with abnormal functioning of these cytokine receptors.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, N.Y.).

Cytokine Receptors

The term "cytokine" refers herein to any cytokine including growth factor. Similarly, the term "cytokine receptors" refers herein to any cytokine receptor including growth factor receptors. The cytokine receptors comprise a number of families including 1—tyrosine kinases receptors, such as vascular endothelial growth factor receptors (VEGFR), PDGFR, IGF-1R, FGFR, EGFR; 2—type I receptors, such as Interleukins-2, 3, 4, 5, 7, 9 and 15; 3—type II receptors, such as interleukins 10, IFNαR, IFNβR, IFNR; 4—TGFβ; 5—chemokines; and 6—NGF/TNF; 6—interleukins-1 types I and II. The present invention encompasses peptidic agonists or antagonists directed at any cytokine.

The method of identifying cytokines antagonists of the present invention is based on the localization of flexible extracellular regions, including regions between domains, long loops between two β chains, as well as juxtamembranous regions of the receptor, which are important for the appropriate conformation and/or oligomerization of the subunits of the receptor and/or its resulting activation. These regions can be determined using for example crystallography data, model structures, data bases, sequence alignments and the like. For example, the targeted regions were established herein based on crystal structure data provided by crystallography for IL-1R and IGF-1R and on published model structure for IL-4R. Databases such as Swiss-Prot and NCBI as well as sequences alignments with CLUSTALW and MOTIFSCAN enabled a comparison between many regions constituting the receptors domains and their structural similarities with flexible regions of the vascular endothelial growth factor receptor (VEGFR). It should be noted that the flexible regions of the present invention need not be directly involved in oligomerization. Indeed, regions which facilitate oligomerization or regions that are implicated in conformational changes needed for receptor signaling are also within the scope of the present invention. The same principle apply to the identification of cytokine agonists.

The terminology "juxtamembranous region of a receptor" refers herein to an extracellular region of the receptor located in the vicinity of the cellular membrane. More particularly in a region which spans a length of up to about 20 amino acids.

The terminology "flexible region of a receptor" refers herein to any region of the receptor that possesses sufficient flexibility to enable this region to bend, extend, twist or otherwise change its conformation and by which conformational change alone or in combination with other conformational changes of other flexible regions, receptor's activity is induced or facilitated. It includes juxtamembranous regions, oligomerization regions including those having secondary structures such as α helix, β sheet, loops, β turns, and flexible regions between domains of the receptor or in long loops between two β chains.

Peptides Preparation

The peptides of this invention, including the analogs and other modified variants, may generally be synthesized according to the FMOC protocol in an organic phase with protective groups. They can be purified with a yield of 70% with HPLC on a C18 column and eluted with an acetonitrile gradient of 10-60%. Their molecular weight can then be verified by mass spectrometry.

The peptides of the invention may also be prepared according to the solid phase synthetic method. For example, the solid phase synthesis is well known and is a common method for preparation of peptides, as are a variety of modifications of that technique [Merrifield (1964), J. Am. Chem. Soc., 85: 2149; Stewart and Young (1984), Solid Phase Peptide Synthesis, Pierce Chemical Company, Rockford, Ill.; Bodansky and Bodanszky (1984), The Practice of Peptide Synthesis, Springer-Verlag, New York; Atherton and Sheppard (1989), Solid Phase Peptide Synthesis: A Practical Approach, IRL Press, New York].

Alternatively, peptides of this invention may be prepared in recombinant systems using polynucleotide sequences encoding the peptides. It is understood that a peptide of this invention may contain more than one of the above described modifications within the same peptide. Also included in this invention are pharmaceutically acceptable salt complexes of the peptides of this invention or their derivatives.

Peptides

Peptides of the present invention may therefore be constituted solely of L-amino acid sequences identical to amino acid sequences of flexible regions of an animal cytokine receptor and preferably of the human cytokines receptor that they target (subfragment peptides) and any mutated peptide that can be generated.

While subfragment peptides are effective in inhibiting wild-type cytokines in vitro, their effectiveness in vivo might be compromised by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Power, et al. (1993), Pharmaceutical Res., 10:1268-1273). In light of this, it is often advantageous to utilize modified versions of subfragment peptides. The modified peptides retain the structural characteristics of the original L-amino acid peptides that confer biological activity with regard to cytokines, but are advantageously not readily susceptible to cleavage by proteases and/or exopeptidases.

Therefore, in specific modes, the peptides of this invention are not subfragment peptides, although their amino acid sequence is derived from the linear sequence of the human cytokine receptors or the corresponding sequences of non-human cytokine receptors and able to inhibit a cytokine receptor's activation (e.g. oligomerization) and more particularly the activation of a human cytokine receptor. Particularly, suitable non-human cytokine receptors sources include mouse, rat, quail and horse. It is thus apparent that multiple systems can provide suitable peptides and derivatives from which the cytokine receptor antagonists of the present invention can be derived.

The term "peptides" as referred to herein therefore includes cytokine receptor subfragment peptides, D-peptides and other modified forms of the peptides, so long as the modification does not alter ability to modulate cytokine receptor activity. All agonists and antagonists peptides of this invention share the ability to modulate the activity of specific cytokines receptors. Non-limiting examples of modifications include N-terminal acetylation, glycosylation, and biotinylation. Particular modified versions of the subfragment peptides according to the present invention are further described below. Although the peptides of the present invention encompass any peptide derived from the flexible regions of cytokines receptors, preferred peptides of the present invention are chosen so as to be specific to a particular receptor isoform (e.g. VEGFR-2) to ensure that their spatial conformation is complementary to the flexible region that they target. This latter characteristic is obtained by choosing where the peptide will be cut according to the properties afforded by each amino-acid in the remaining sequence (e.g. if the peptide has to follow the specific curve of the domain targeted).

The term "peptides derived from a flexible region" refers herein to peptides of 5 to about 20 amino acids that have been generated to correspond to segments of 5 to 20 contiguous amino acids located anywhere in the flexible regions and that may have been subjected to further modification or functional derivation as described herein. Preferably, the peptides derived from a flexible region is a peptide of at least 7 amino acids.

D-amino acid peptides can have modifications at the N-terminal amino-acid and at the C-terminal amino-acid. The presence of an N-terminal or C-terminal D-amino acid increases the serum stability of a peptide which otherwise contains L-amino acids, because exopeptidases acting on these residues cannot utilize a D-amino acid as a substrate (Powell, et al. (1993)). Cyclic peptides have no free N- or C-termini. Thus, they are not susceptible to proteolysis by exopeptidases, although they are of course susceptible to endopeptidases, which do not cleave at peptide termini. Thus, the amino acid sequences of the peptides with N-terminal or C-terminal D-amino acids and of the cyclic peptides are usually identical to the sequences of the subfragment peptides to which they correspond, except for the presence of an N-terminal or C-terminal D-amino acid residue, or their circular structure, respectively.

Substitution of unnatural amino acids for natural amino acids in a subsequence of the subfragment of cytokine receptor peptide can also confer resistance to proteolysis. Such a substitution can, for instance, confer resistance to proteolysis by exopeptidases acting on the N-terminus. Such substitutions have been described (Coller, et al. (1993), J. Biol. Chem., 268:20741-20743, incorporated herein by reference) and these substitutions do not affect biological activity. Furthermore, the synthesis of peptides with unnatural amino acids is routine and known in the art (see, for example, Coller, et al. (1993), supra).

An other effective approach to confer resistance to peptidases acting on the N-terminal or C-terminal residues of a peptide is to add chemical groups at the peptide termini, such that the modified peptide is no longer a substrate for the peptidase. One such chemical modification is glycosylation of the peptides at either or both termini. Certain chemical modifications, in particular N-terminal glycosylation, have been shown to increase the stability of peptides in human serum [Powell et al. (1993), supra]. Other chemical modifications which enhance serum stability include, but are not limited to, the addition of an N-terminal alkyl group, consisting of a lower alkyl of from 1 to 20 carbons, such as an acetyl group, and/or the addition of a C-terminal amide or substituted amide group. In particular the present invention includes modified peptides consisting of subfragment peptides bearing an N-terminal acetyl group and a C-terminal amide group.

Longer peptide sequences which result from the addition of extra amino acid residues to the peptides of the invention are encompassed in the present invention since they should have the same biological activity (inhibit oligomerization of cytokines) as the peptides described above. While peptides having a substantial number of additional amino acids are not excluded, it will be recognized that some large polypeptides may assume a configuration that masks the effective sequence, thereby preventing binding to cytokines. These derivatives will act as competitive antagonists and are thereby excluded from the invention. Thus, while the present invention encompasses peptides or derivatives having an extension, such longer peptides should be selected as not destroying the modulating activity of the peptide or derivative.

The present invention also encompasses peptides constituted of the sequences of two peptides having separately the property of inhibiting the activation (e.g. oligomerization) of a particular cytokine receptor, but not being contiguous within the flexibility regions. These peptides can also be described as having a sequence corresponding to the particular cytokine receptor with an internal deletion.

In another embodiment of this invention the peptides are reverse-D peptides corresponding to the amino acid sequence of the cytokine. The term "reverse-D peptide" refers herein to peptides containing D-amino acids, arranged in a reverse sequence relative to a peptide containing L-amino acids. Thus, the C-terminal residue of an L-amino acid peptide becomes N-terminal for the D-amino acid peptide, and so forth. For example, the sequence of the reverse-D peptide corresponding to subfragment peptide SEQ ID NO: 1 is: GVLIIIELNTKEQA. Reverse-D peptides retain the same tertiary conformation, and therefore the same activity, as the L-amino acid peptides, but are more stable to enzymatic degradation in vitro and in vivo, and thus have greater therapeutic efficacy than the original peptide (Brady and Dodson (1994), Nature, 368: 692-693; Jameson et al. (1994), Nature, 368: 744-746).

As used herein, the designation "functional derivative" denotes, in the context of a functional derivative of an amino acid sequence, a molecule that retains a biological activity (either function or structural) that is substantially similar to that of the original sequence. This functional derivative or equivalent may be a natural derivative or may be prepared synthetically. Such derivatives include amino acid sequences having substitutions, deletions, or additions of one or more amino acids, provided that the biological activity of the protein is conserved (e.g. it acts as a non-competitive inhibitor or agonist of a cytokine receptor). The substituting amino acid generally has chemico-physical properties which are similar to that of the substituted amino acid. The similar chemico-physical properties include, similarities in charge, bulkiness, hydrophobicity, hydrophilicity and the like. The term "functional derivatives" is intended to include "segments", "variants", "analogs" or "chemical derivatives" of the subject matter of the present invention.

Thus, the term "variant" refers herein to a protein which is substantially similar in structure and biological activity to the protein or nucleic acid of the present invention.

The functional derivatives of the present invention can be synthesized chemically or produced through recombinant DNA technology. All these methods are well known in the art.

While peptides of specific embodiments of the present invention are preferably derived from human cytokines receptors, the invention should not be so limited. Indeed, in view of the significant conservation of flexible regions of these genes throughout evolution, sequences from different species, as discussed above and preferably mammalian species, could be used in the assays of the present invention. For instance, non-limiting examples for the VEGFR protein are the quail, mouse, rat and horse VEGFR protein sequences which show 70%, 82% and 82% similarity, respectively with the human VEGFR protein sequence. Similarly, the IL-1R mouse, rat and horse protein sequences show a 68%, 67% and 77% sequence similarity, respectively. Also, the IL-4R mouse and horse protein sequences show a 48% and 59% sequence similarity, respectively (as calculated by blast™).

For administration to humans, the prescribing medical professional will ultimately determine the appropriate form and dosage for a given patient, and this can be expected to vary according to the chosen therapeutic regimen (e.g. peptides, variants, mimetics), the response and condition of the patient as well as the severity of the disease.

Composition within the scope of the present invention should contain the active agent (e.g. peptide) in an amount effective to achieve the desired therapeutic effect while avoiding adverse side effects. Typically, the nucleic acids in accordance with the present invention can be administered to mammals (e.g. humans) in doses ranging from 0.005 to 1 mg per kg of body weight per day of the mammal which is treated. Pharmaceutically acceptable preparations and salts of the active agent are within the scope of the present invention and are well known in the art (Remington's Pharmaceutical Science, 16th Ed., Mack Ed.). For the administration of polypeptides, antagonists, agonists and the like, the amount administered should be chosen so as to avoid adverse side effects. The dosage will be adapted by the clinician in accordance with conventional factors such as the extent of the disease and different parameters from the patient. Typically, 0.001 to 50 mg/kg/day will be administered to the mammal.

Assays to Identify Peptides of the Present Invention

Preferred methods for testing the ability of candidate compounds to inhibit the various cytokine receptors activity are presented herein. It will be understood that the invention is not so limited. Indeed, often assays well known in the art can be used in order to identify non-competitive, extracellular agonists or antagonists of the present invention.

As used herein, "cytokine receptor activity or activation" refers to any detectable biological activity of these proteins. This includes any physiological function attributable to a cytokine receptor such as any standard biochemical measurement of these receptors, conformational changes, phosphorylation status, any downstream effect of the receptor's signaling such as protein phosphorylation, kinase effect or any other feature of the protein that can be measured with techniques known in the art. Measuring the effect of a candidate peptide on its ability to modulate the oligomerization of the receptor is measuring a cytokine receptor's activity according to this invention. Broadly intra- or inter-molecular binding of the receptor in the absence vs the presence of the peptide of the invention is yet another example of a biological activity according to the invention.

The assays of this invention employ either a natural or recombinant cytokine receptor. A cell fraction or cell free screening assays for inhibitors of cytokine receptor activity can use in situ purified, or purified recombinant cytokine receptor. Cell-based assays can employ cells which express cytokine receptor naturally, or which contain recombinant cytokine receptor. In all cases, the biological activity of cytokine receptor can be directly or indirectly measured; thus inhibitors or activators of cytokine receptor activity can be identified. The inhibitors or activators themselves may be further modified by standard combinatorial chemistry techniques to provide improved analogs of the originally identified compounds.

It shall be understood that the "in vivo" experimental model can also be used to carry out an "in vitro" assay.

In Vitro Assays

In one embodiment, candidate peptides are tested for their ability to activate or inhibit cytokine receptor's ability to modulate cellular proliferation with the incorporated triated thymidine method. In yet other preferred embodiments, candidate peptides are tested for their ability to inhibit a particular cytokine receptor's ability to modulate cellular proliferation, using for example, the assays described in Baker F. L. et al. (1995) Cell Prolif. 28(1):1-15; Cheviron N. et al. (1996) Cell Prolif. 29(8):437-46; Hu Z. W. et al. (1999) J. Pharmacol. Exp. Ther. 290(1):28-37; and Elliott K. et al. (1999) Oncogene 18(24):3564-73.

In another preferred embodiment, candidate peptides are tested for their ability to modulate the phosphorylation state of cytokine protein or portion thereof, or an upstream or downstream target protein, using for example an in vitro kinase assay. Briefly, a cytokine receptor target molecule (e.g. an immunoprecipitated receptor from a cell line expressing such a molecule), can be incubated with radioactive ATP, e.g., [gamma-$^{32}$P]-ATP, in a buffer containing $MgCl^2$ and $MnCl^2$, e.g., 10 mM $MgCl^2$ and 5 mM $MnCl^2$. Following the incubation, the immunoprecipitated receptor target molecule, can be separated by SDS-polyacrylamide gel electrophoresis under reducing conditions, transferred to a membrane, e.g., a PVDF membrane, and autoradiographed. The appearance of detectable bands on the autoradiograph indicates that the receptor substrate has been phosphorylated. Phosphoaminoacid analysis of the phosphorylated substrate can also be performed in order to determine which residues on the receptor substrate are phosphorylated. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards. Assays such as those described in, for example, Tamaskovic R. et al. (1999) Biol. Chem. 380(5):569-78.

In other embodiments, candidate peptides targeting IL-1R are tested with $PGE_2$ levels, IL-6, collagenase expression in chondrocytes and RPE; candidate peptides targeting IGF-1R are tested with Akt in Du145 and PC12; candidate peptides targeting IL-4R are tested with Akt in Thelper and PAEC and with VCAM-1 expression in PAEC.

In Vivo Assays

The assays described above may be used as initial or primary screens to detect promising lead compounds for further development. Lead peptides will be further assessed in additional, different screens. Therefore, this invention also includes secondary cytokine receptors screens which may involve various assays utilizing mammalian cell lines expressing these receptors or other assays.

Tertiary screens may involve the study of the identified inhibitors in animal models for clinical symptoms. Accordingly, it is within the scope of this invention to further use an agent (peptide or peptidomimetic) identified as described herein in an appropriate animal model such as a rat or a mouse. For example, a peptide can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatment (e.g. treatments of different types of disorders associated with a deregulation or malfunction of a cytokine receptor), as described herein. Preferred such experiments include collagen-induced arthritis in rat, acute septic shock in rat, tumor growth in immunosuppressed mouse, sensitization of the airways in newborn mice and any other known animal model including transgenics.

Assays to Identify Peptidomimetics

Non-peptidyl compounds generated to replicate the backbone geometry and pharmacophore display (peptidomimetics) of the peptides identified by the methods of the present invention often possess attributes of greater metabolic stability, higher potency, longer duration of action and better bioavailability.

The peptidomimetics compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, Anticancer Drug Des. 12: 145, 1997). Examples of methods for the synthesis of molecular libraries can be found in the art, for example in: DeWitt et al. (1993) Proc. Natl. Acad. Sci. USA. 90:6909; Erb et al. (1994) Proc. Natl. Acad. Sci. USA 91:11422; Zuckermann et al. (1994), J. Med. Chem. 37:2678; Cho et al. (1993) Science 261 :1303; Carrell et al. (1994) Angew. Chem, Int. Ed Engl. 33:2059; and ibid 2061; and in Gallop et al. (1994). Med Chem. 37:1233. Libraries of compounds may be presented in solution (e.g. Houghten (1992) Biotechniques 13:412-421) or on beads (Lam (1991) Nature 354:82-84), chips (Fodor (1993) Nature 364:555-556), bacteria or spores (Ladner U.S. Pat. No. 5,223,409), plasmids (Cull et al. (1992) Proc Natl Acad Sci USA 89:1865-1869) or on phage (Scott and Smith (1990); Science 249:386-390). Examples of methods for the synthesis of molecular libraries can be found in the art, for example in: DeWitt et al. (1993) supra; Erb et al. (1994) supra; Zuckermann et al. (1994) supra; Cho et al. (1993) supra; Carrell et al. (1994) supra, or luciferase, and the enzymatic label detected by determination of conversion of an appropriate substrate to product.

In one embodiment, the peptidomimetics compounds of the present invention are preferably obtained with the following three phase process. 1) Scanning the peptides of the present invention to identify regions of secondary structure necessary for recognition and activity toward the cytokine receptor; 2) use conformationally constrained dipeptide surrogates to refine the backbone geometry and provide organic platforms corresponding to these surrogates; 3) Use the best organic platforms to display organic pharmocophores in libraries of candidates designed to mimic the desired activity of the native peptide. In more details the three phases are as follows.

In phase 1, the peptide leads are scanned and their structure abridged to identify the requirements for their activity. A series of peptide analogs of the original are synthesized. In phase 2, the best peptide analogs are investigated using the conformationally constrained dipeptide surrogates. Indolizidin-2-one, indolizidin-9-one and quinolizidinone amino acids ($I^2$aa, $I^9$aa and Qaa respectively)) are used as platforms for studying backbone geometry of the best peptide candidates. These platforms are introduced at specific regions of the peptide in order to orient the pharmacophores in different directions. Biological evaluation of these analogs identifies improved leads that mimic the geometric requirements for activity. In phase 3, the platforms from the most active leads are used to display organic surrogates of the pharmacophores responsible for activity of the native peptide. The pharmacophores and scaffolds are combined in a parallel synthesis format.

In summary, based on the disclosure herein, those skilled in the art can develop peptides and peptidomimetics screening assays which are useful for identifying compounds which are useful for inhibiting cytokine receptors. Compounds so identified might also be shown to activate these receptors. The assays of this invention may be developed for low-throughput, high-throughput, or ultra-high throughput screening formats. Of course, assays of the present invention include assays which are amenable to automation.

More specifically, in accordance with one embodiment, the present invention, there is provided a method for identifying a non-competitive peptide which inhibits the oligomerization of a cytokine receptor, the method comprising the steps of selecting a candidate peptide containing from about 7 to about 20 amino acids derived from a flexible region of the receptor, and determining the ability of the peptide to inhibit the oligomerization of the receptor by measuring an activity of the receptor in the presence of a compound known to activate the receptor and in the absence or the presence of the candidate peptide, wherein the non-competitive peptide is selected when the activity of the receptor is measurably lower in the presence of the peptide as compared to in the absence thereof.

There is also provided a non-competitive extracellular cytokine receptor antagonist wherein the antagonist is a peptide containing from about 7 to about 20 amino-acids derived from a flexible region of the cytokine receptor.

The present invention also provides methods of treating diseases or conditions associated with a abnormal activity of a cytokine receptor comprising administration of a suitable amount of peptide or derivative of the invention.

The present invention also relates to pharmaceutical compositions comprising a modulating amount a or cytokine receptor subfragment peptide or derivative of the present invention, together with a suitable pharmacological carrier.

The terms "inhibiting," "reducing" or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

In the appended drawings:

FIG. 3 shows the sequence of the human VEGFR-2 (Flk-1). Boxed or underlined sequences represent the identified flexible region of VEGFR (SEQ ID NO:20);

FIG. 4 shows the sequence of human Interleukin-1 receptor (IL-1R-alpha). Boxed or underlined sequences represent the identified flexible region of IL-1R-alpha (SEQ ID NO:21);

FIG. 5 shows the sequence of human Interleukin-1 receptor accessory protein (IL-1RacP). Boxed or underlined sequences represent the identified flexible region of IL-1RacP (SEQ ID NO:22);

FIG. 6 shows the sequence of human Insulin-like growth factor I receptor (IGF-1R). Boxed or underlined sequences represent the identified flexible region of IGF-1R (SEQ ID NO:23);

FIG. 7 shows the sequence of the human alpha chain of the Interleukin 4 receptor (IL-4R). Boxed or underlined sequences represent the identified flexible region of IL-4R (SEQ ID NO:24);

FIG. 8 graphically illustrates results of proliferation assays in carcinome A549 cells in presence of IGF-1 (10 ng/ml-Panel A) (1 ng/ml-Panel B) and various concentrations of the peptides APG-201, APG-202 and APG-204;

FIG. 11 shows an alignment of the human IL-1R sequence with corresponding mouse, rat and horse sequences (SEQ ID NOS:25, 26, 27, and 28);

FIG. 12 shows an alignment of the human IL-4R sequence with corresponding mouse and horse sequences (SEQ ID NOS:29, 60, and 61); and FIG. 13 shows an alignment of the human VEGFR2 sequence with corresponding mouse, rat and quail sequences (SEQ ID NOS:62, 63, 64, and 65).

DESCRIPTION OF SPECIFIC EMBODIMENTS

Figure 1:
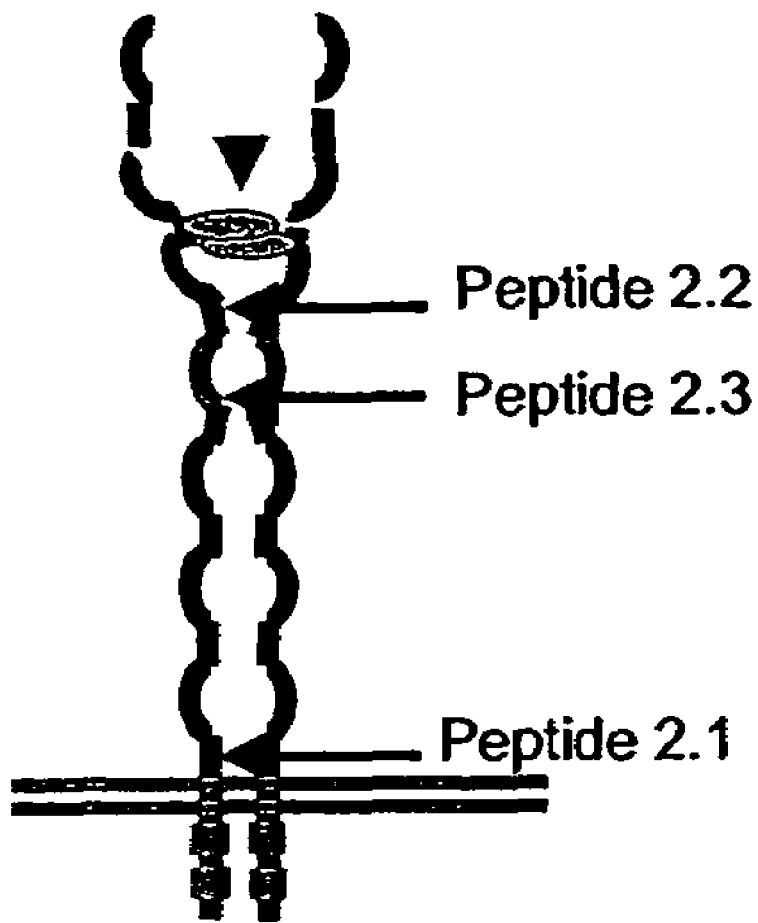
FIG. 1 schematically illustrates the position of VEGFR antagonists on the receptor according to specific embodiments of the present invention.

Table 1 presents the localization of flexible regions of various representative members of the cytokine receptors families along with exemplary peptide sequences derived from these regions and chosen for their specificity to the particular member they target. As explained above, many peptides can be derived from the targeted regions of the present invention and the peptides described hereinbelow are only exemplary.

TABLE 1

Amino acids involved in the oligomerization and stability of receptors of representative members of various cytokine receptors

| CYTOKINES RECEPTOR TYPES | SPECIFIC RECEPTORS | REGIONS TARGETED | LOCALISATION OF THE SEQUENCE FROM THE STARTING METHIONINE | PEPTIDE SEQUENCES |
|---|---|---|---|---|
| Tyrosine Kinase receptor | VEGFR2 (Flk-1) | Juxtamembranous | Aa 745-770 | AQEKTNLEIIILVG (2.1) SEQ ID NO. 1 |
| | | Ig3-Ig4 | Aa 320-350 | EATVGERVRL (2.2) SEQ ID NO. 2 |

TABLE 1-continued

Amino acids involved in the oligomerization and stability of receptors of representative members of various cytokine receptors

| CYTOKINES RECEPTOR TYPES | SPECIFIC RECEPTORS | REGIONS TARGETED | LOCALISATION OF THE SEQUENCE FROM THE STARTING METHIONINE | PEPTIDE SEQUENCES |
|---|---|---|---|---|
| | | Ig-4 dimerization domain | Aa 350-400 | LPLESNHTLK (2.3) SEQ ID NO. 3 |
| | | Ig-4-Ig-5 | Aa 400-440 | SPVDSYQYGTT; SEQ ID NO. 4 VILTNPISKE; SEQ ID NO. 5 |
| | | Ig-5-Ig 6 | Aa 481-565 | NKVGRGERVI; SEQ ID NO. 6 MPPTEQESV SEQ ID NO. 7 |
| | | Ig-6-Ig-7 | Aa 640-685 | RKTKKRHCV; SEQ ID NO. 8 TVLERVAPT; SEQ ID NO. 9 TSIGESIEV SEQ ID NO. 10 |
| | IGF-1R | On chain α: | | |
| | | Juxtamembranous | Aa 725-740 | SIFVPRPERK; SEQ ID NO. 11 NFLHNSIFV; SEQ ID NO. 12 |
| | | Cyst rich domain-L2 | Aa 320-335 | EGPCPKVCE; SEQ ID NO. 13 |
| | | L2-FbnIII-1 | Aa 487-527 | ESDVLHFTST; SEQ ID NO. 14 |
| | | FbnIII-1-FbnIII2a | Aa 595-620 | RTNASVPSI; SEQ ID NO. 15 |
| | | FbnIII-2a-Insert domain | Aa 660-690 | IRKYADGTI; SEQ ID NO. 16 |
| | | On chain β: | | |
| | | Insert domain-FbnIII2b | Aa 780-799 | ENFIHLIIA; SEQ ID NO. 17 AKTGYENFIH; SEQ ID NO. 18 |
| | | FbnIII2b-FbnIII3 | Aa 820-840 | KERTVISNLR; SEQ ID NO. 19 |
| | | Juxtamembranous | Aa 917-947 | FVFARTMPA; SEQ ID NO. 30 |
| | EGFR | Juxtamembranous | Aa 640-650 | NGPKIPSIAT; SEQ ID NO. 31 |
| | | Loop L2-S2 (flexible) | Aa 495-515 | ATGQVCHAL; SEQ ID NO. 32 |
| | | Loop S1-L2 (Hinge) | Aa 335-345 | RKVCNGIGIGE; SEQ ID NO. 33 |
| Type I: Chain γc | IL-4R | Juxtamembranous | Aa 210-240 | WHNSYREPF; SEQ ID NO. 34 YREPFEQHLL; SEQ ID NO. 35 |

TABLE 1-continued

Amino acids involved in the oligomerization and stability of receptors of representative members of various cytokine receptors

| CYTOKINES RECEPTOR TYPES | SPECIFIC RECEPTORS | REGIONS TARGETED | LOCALISATION OF THE SEQUENCE FROM THE STARTING METHIONINE | PEPTIDE SEQUENCES |
|---|---|---|---|---|
| | | Hinge zone D2 | Aa 125-216 | SDTLLLTWS; SEQ ID NO. 36 IYNVTYLE; SEQ ID NO. 37 IAASTLKSGIS; SEQ ID NO. 38 |
| | | Loop D1-D2 | Aa 112-125 | KPSEHVKPR; SEQ ID NO. 39 |
| Single chain | GHR | Juxtamembranous flexible region (D1-D2) | Aa 250-270 Aa 160-240 | FTCEEDFYFPW; SEQ ID NO. 40 SVDEIVQPD; SEQ ID NO. 41 MDPIDTTSVPVY; SEQ ID NO. 42 |
| IL-1R | IL-1R | Juxtamembranous | Aa 320-341 | IDAAYIQLIYPV; SEQ ID NO. 43 LIYPVTNFQKHM SEQ ID NO. 44 |
| | | Between Ig-like domain 2 and 3 (Hinge) | Aa 209-240 | LEENKPTRPV; SEQ ID NO. 45 NKPTRPVIVS; SEQ ID NO. 46 |
| | | Ig-like 2 loop e2-f2 (pas int.ligand) | Aa 181-200 | VAEKHRGNYT; SEQ ID NO. 47 WNGSVIDED SEQ ID NO. 48 |
| | IL-1RacP | Juxtamembranous | Aa 330-370 | VPAPRYTVEL; SEQ ID NO. 49 APRYTVELA; SEQ ID NO. 50 |
| | | Hinge regions: | | |
| | | Loop Ig-1-2: | Aa 115-160 | VQKDSCFNSPM; SEQ ID NO. 51 MKLPVHKLY SEQ ID NO. 52 |
| | | Loop Ig-2-3 | Aa 170-266 | VGSPKNAVPPV; SEQ ID NO. 53 VTYPENGRTF; SEQ ID NO. 54 IHSPNDHVVY; SEQ ID NO. 55 |
| | | dimerization region | Aa 200-215; 275-295; 300-315 | LISNNGNYT; SEQ ID NO. 56 VWWTIDGKKPD; SEQ ID NO. 57 WTIDGKKPDDI; SEQ ID NO. 58 HSRTEDETRTQ SEQ ID NO. 59 |

Cytokines receptors modulators according to specific embodiments of the present invention will now be described as well as the procedure to identify them and to test their efficiency in vitro and/or in vivo by the following non-limiting examples.

EXAMPLE 1

VEGFR

Identification of VEGFR2 Antagonists

VEGF is a proliferating agent for endothelial cells. Its receptor (VEGFR) is present at the plasma membrane of endothelial cells as a monomer and its homodimerization is necessary for generating autophosphorylation via its intrinsic tyrosine kinase domain.

The method of identifying VEGFR antagonists of the present invention is based on the localization of extracellular flexible regions including regions between domains and juxtamembranous regions of the receptor that are important for the appropriate conformation and oligomerization of the subunits of the receptor and its resulting activation. These regions were established based on crystal structure data provided by crystallography. The antagonists able to bind to these regions block the signal transduction by interfering with the oligomerization. The regions so identified appear in green in FIG. 3. One of those regions is located under the IG-like 3 domain where ligand binding is located, namely between residues 320 and 350. The ligand binding location also appears in FIG. 1. A second region was identified in the oligomerization domain of two subunits of Ig-like 4, namely between residues 350 and 400. A third region was identified located at the juncture of the receptor with the cellular membrane, namely between residues 745 and 770. This region is important for the dimer stability. These regions do not interfere with the ligand binding so that any antagonist (peptide, small molecule) targeting these regions is not a competitor for the ligand binding sites (non-competitive antagonist) and prevents or limits the oligomerization required for the autophosphorylation of the receptor. Three D-peptides of up to 12 amino-acids (designated 2.1, 2.2 and 2.3) were derived from the amino-acid sequence of these regions and tested as antagonists. As mentioned earlier, D-peptides are preferred over subfragment peptides (of course subfragments could also be rendered protease resistant by well known means) because they are less likely degradable by various proteases. These particular peptides were selected among all those that could have been derived from the identified flexible regions of interest because of their specificity to VEGFR-flk-1: sequences alignments were performed with other receptors from VEGFR's family (PDGFR, Flt-1) showing the specificity of the selected three peptides. Of course, such alignments enable a selection of other specific peptides or alternatively of more general antagonists. It should be understood that the principles related to positioning discussed herein in relation to VEGFR can be applied to other types of cytokine receptors sharing similar morphologies.

The location of the three peptides appear in FIG. 1, the ligand binding region appears in red, the oligomerization domain per se appears in green and the tyrosine kinase domain appears in purple.

In FIG. 3, the domains of the VEGFR isoform VEGFR-2 are identified with arrows pointing at the start of each domain. The regions where antagonists of the present invention may bind to prevent the oligomerization and/or activation of the receptor are boxed or underlined. The underlined sequences denote the regions between domains while the boxed sequences denote the juxtamembranous regions. The regions from where peptides 2.1, 2.2 and 2.3 are derived are identified in italic and are underlinded. The sequences that the peptides target according to the invention appear underlined and boxed.

Characterization of Peptides In Vitro

To determine the efficient and non cytotoxic concentration of VEGF to use in the assay, a dose-response curve of VEGF was generated in two types of cells, namely microvascular endothelial cells and pulmonary artery endothelial cells (PAEC) that had been transfected with the Flk-1 gene. The proliferation was then measured in those two types of cells in the presence of peptides 2.1, 2.2 and 2.3 and of VEGF (2 ng/ml) pursuant to the incorporated tritiated thymidine method. The cells were preincubated at 37° C. with the different peptides at different concentrations. They were incubated with VEGF (2 ng/ml) for 24 hours. The cells were contacted with $^3$H-Thymidine for 24 hours, washed and lysed. The radioactivity was measured with a scintillation counter.

Figure 2:
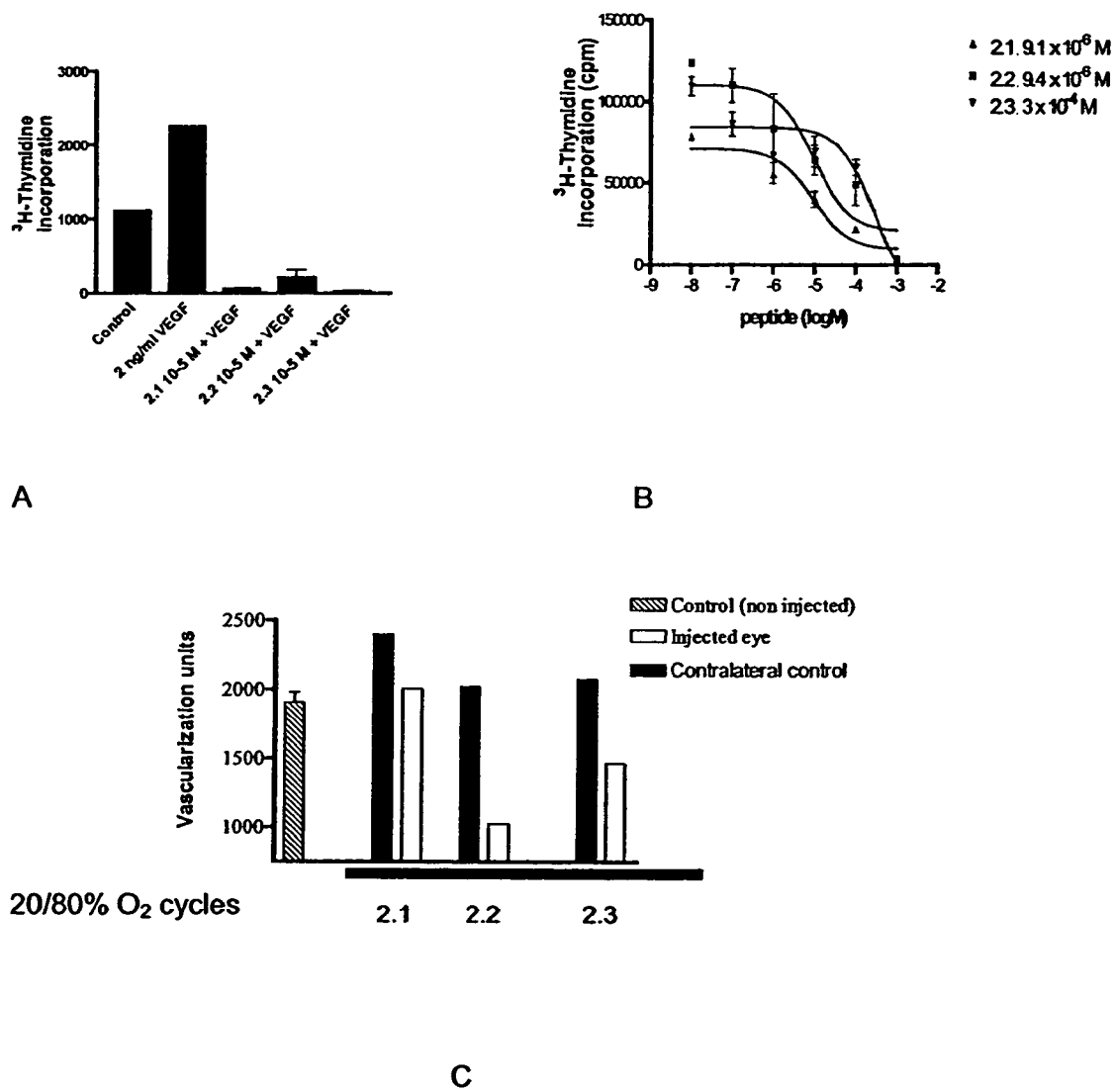
FIG. 2 graphically illustrates in panel A results of proliferation assay in porcine microvascular endothelial cells in presence of VEGF (2 ng/ml) and peptides 2.1, 2.2, 2.3 (10 µM). In panel B are graphically illustrated dose-response of peptides in pulmonary arterial endothelial cells (PAEC) in presence of VEGF (2 ng/ml) and increasing doses of peptides. In panel C is graphically illustrated the effect of intravitreally injected peptides (10 µM [estimated final intraocular concentration]) of the present invention on neovascularization in rat retinas exposed to hyperoxic conditions.
Figure 9:
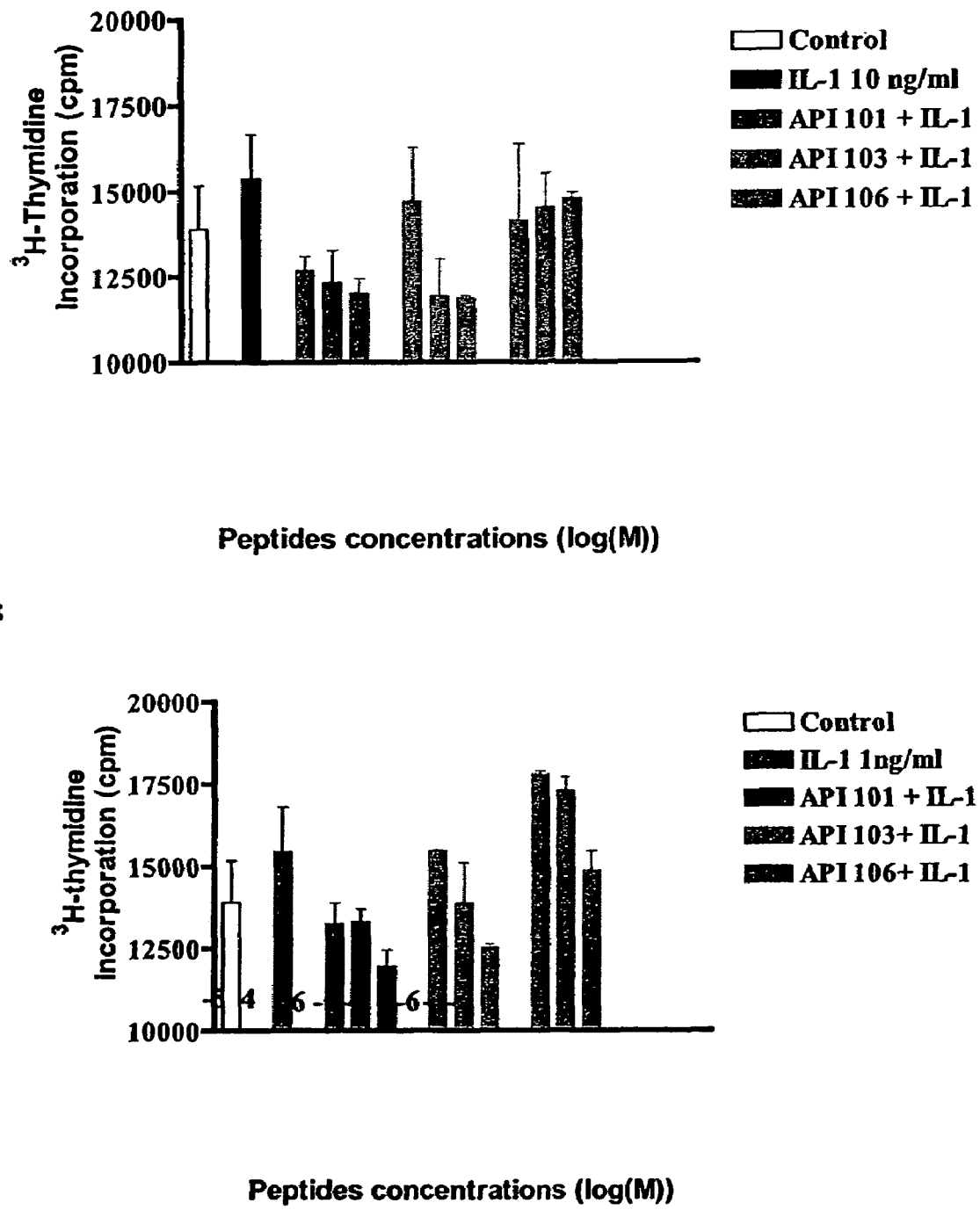
FIG. 9 graphically illustrates results of proliferation assays in carcinome A549 cells in presence of IL-1 (10 ng/ml-Panel A) (1 ng/ml-Panel B) and various concentrations of the peptides API-101, API-103 and API-106.

As may be seen in panels A and B of FIG. 2, the peptides 2.1, and 2.2 completely abrogated VEGF induced proliferation in microvascular endothelial cells, and in PAEC with an $EC_{50}$ of 9 µM, respectively. In addition, using these PAEC transfected with the cDNAs for either of the VEGFR isoforms Flk-1 and Flt, the selectivity of the peptides was demonstrated as they were shown to be ineffective in modulating biological functions in the VEGFR Flt isoform-containing cells (data not shown).

Characterization of Peptides In Vivo

Ischemic Retinopathy Model

The efficiency of the selected peptides was verified in vivo in a ischemic retinopathy model, a phenomena highly dependant on VEGF activation. Rat pups were exposed to 80% $O_2$ followed by a period of normoxia (21% $O_2$). The peptides were injected at a final concentration of 10 µM in the vitreous body. The retinas were then retrieved, colored with the ADPase method and mounted on slides. Photographs of the retinas were taken with a microscope linked to a computer and the vascular density was evaluated with the Image prosoftware. As illustrated in FIG. 2, panel C, the results of this experiment demonstrated that all peptides tested prevented induced neovascularization in vivo. Peptide 2.2 was shown to be the most effective inhibitor of neovascularization. Specific peptides of the present invention were shown to prevent effects generated by activation of Flk-1 with VEGF by interfering with flexible regions of Flk-1 receptor.

EXAMPLE 2

Insulin-Like Growth Factor-1 Receptor (IGF-1R)

IGF-1 is a small peptide and a member of a family of insulin related peptides. It consists of 70 amino acids and has structural similarity with insulin. IGF-1 is secreted by many tissues (cartilage, bone, epithelium, endothelium) but mostly by the liver to act on other tissues in an endocrine fashion. It exerts its actions by binding to IGF-1R upon which it sends a mitogenic signal. It can also protect cells from apoptosis, promote proliferation, regulate cell adhesion and motility and differentiation. The receptor itself is expressed in most cell types except in the hepatocytes. Because of its growth inducing functions, IGF-1R is also very much involved in malignant transformation or differentiation in various types of cancer such as glioblastomas, neuroblastomas, prostate, breast and ovarian cancer.

IGF-1 plays a critical role in cell growth, survival and metastatic differentiation. IGF-1R is a transmembrane tyrosine kinase protein, which is widely expressed. Increased IGF-1R expression is observed in a number of tumour types, and epidemiological data implicates it in cancers such as those of the prostate and breast. Recent progress has been made on its 3-dimensional structure. ps Design of Peptides for IGF-1

The approach described in Example 1 is used to generate antagonists to IGF-1R. The precise localization of these regions is described in Table 1 above along with exemplary sequences of subfragment peptides or modified peptides targeting one of these regions and presenting specificity to IGF-1R. Three D-peptides (designated APG201, APG202 and APG204) were then derived from the amino-acid sequence of these regions to act as antagonists. The sequences of these peptides antagonists are as follows: APG-201 SLFVPRPERK; APG-202 ESDVLHFTST; APG-204 LRKYADGTL. They generally correspond to the subfragment peptides having sequences SEQ ID NOs: 11, 14 and 16, respectively, except where the subfragment peptide contained an isoleucine. Similarly, In that case, this amino-acid was replaced by leucine in the synthesized peptide for economic reasons.

Characterization of Peptides In Vitro and In Vivo

The affinity is determined using binding studies on cells expressing and overexpressing IGF-1R. The selectivity is tested by performing bioassays on cells expressing receptors from the same family as IGF-1R and the specificity is tested against receptors of another family of cytokine.

The proliferation of IGF-1 was measured in A549 carcinoma cells in the presence of peptides APG201; APG202 and APG204 and of IGF-1 (10 ng/ml-Panel A) and (1 ng/ml-Panel B) pursuant to the incorporated tritiated thymidine method. The cells were preincubated at 37° C. with the different peptides at different concentrations, namely $10^{-7}$, $10^{-6}$ and $10^{-5}$M. They were then incubated with IGF-1 (10 ng/ml or 1 ng/ml) for 24 hours. The cells were then contacted with $^3$H-Thymidine for 24 hours, washed and lysed. The radioactivity was then measured with a scintillation counter.

As may be seen in panels A and B of FIG. 8, the peptides completely abrogated IGF-1 induced proliferation in A549 carcinoma cells with an $EC_{50}$ of $10^{-8}$M for APG-202 and 204; and of $10^{-6}$M for APG-201.

Further in vitro testing of the antagonists are conducted as described in Table 2.

In vivo experiments are described in Table 5.

TABLE 2

In vitro bioassays for IGF-1R antagonist screening

| Cells | Type | Bioassay | Method |
|---|---|---|---|
| Du145 | Prostate cancer cell line | Proliferation Akt phosphorylation | $^3$H-Thymidine incorporation Western Blot |
| PC12 | Pheochromocytoma cell line | Same as above | Same as above |

EXAMPLE 3

Interleukin 4 (IL-4)

IL-4 is a key cytokine involved in the development of allergic inflammation and allergy. It is generated early on in the process of inflammation in asthma. In allergy it is associated with the production of IgE immunoglobulins by B lymphocytes and will also up-regulate the expression of the IgE receptor on cell surface of B-lymphocytes, basophils and mast cells. In asthma it induces the expression of vascular cell adhesion molecule (VCAM-1) on vascular endothelium. This effect leads to direct migration chemotaxis of T lymphocytes, monocytes, basophils and eosinophils to the inflammatory site on pulmonary vascular endothelial cells. IL-4 inhibits eosinophil apoptosis and promotes eosinophilic inflammation by augmenting their presence in part by increasing expression of eotaxin. Another essential biological effect of IL-4 is Th2 differentiation and proliferation; in this process IL-4 diminishes T lymphocyte apoptosis. The II-4 receptor is a cell-surface protein consisting of an α subunit coupled to a γ subunit for signal transduction; its activation requires oligomerization.

Although IL-4R and IL-13R share a similar IL-4Rα chain, the two receptors exhibit distinct functions; moreover, the main receptor present on TH2 cells is that of IL-4, which for the most part consists of the IL-4Rα and IL-4γc chains. Nevertheless, the identification of modulators of IL-4R activity. Derived from the IL-4Rα are expected to also modulate IL-13R activity.

Design of Peptides for IL-4R

The approach described in Example 1 is used to generate antagonists to IL-4R. The precise localization of these regions is described in Table 1 above along with exemplary sequences of subfragment peptides or modified peptides targeting one of these regions and presenting specificity to IL-4R Characterization of Peptides In Vitro and In Vivo The affinity is determined using binding studies on cells expressing and overexpressing IL-4R. The selectivity is tested by performing bioassays on cells expressing receptors from the same family as IL-4R and the specificity is tested against receptors of another family of cytokine.

The proliferation of IL-4 was measured in A549 carcinoma cells in the presence of peptides API-401, API-402, API-403, API-404 and API-405 and of IL-4 (1 ng/ml) pursuant to the incorporated tritiated thymidine method. The cells were preincubated at 37° C. with the different peptides. They were then incubated with IL-4 (1 ng/ml) for 24 hours. The cells were then contacted with $^3$H-Thymidine for 24 hours, washed and lysed. The radioactivity was then measured with a scintillation counter. The sequences of peptides antagonists used are as follows: API-401 YREPFEQHLL, API-402 SDTLLLTWS; API-403 LYNVTYLE; API-404 LAASTLKSGLS; and API405 KPSEHVKPR. They generally correspond to the subfragment peptides having sequences SEQ ID NOs: 35, 36, 37, 38 and 39, respectively except where the subfragment peptide contained an isoleucine. In that case, this amino-acid was replaced by leucine in the synthesized peptide as mentioned previously.

Figure 10:
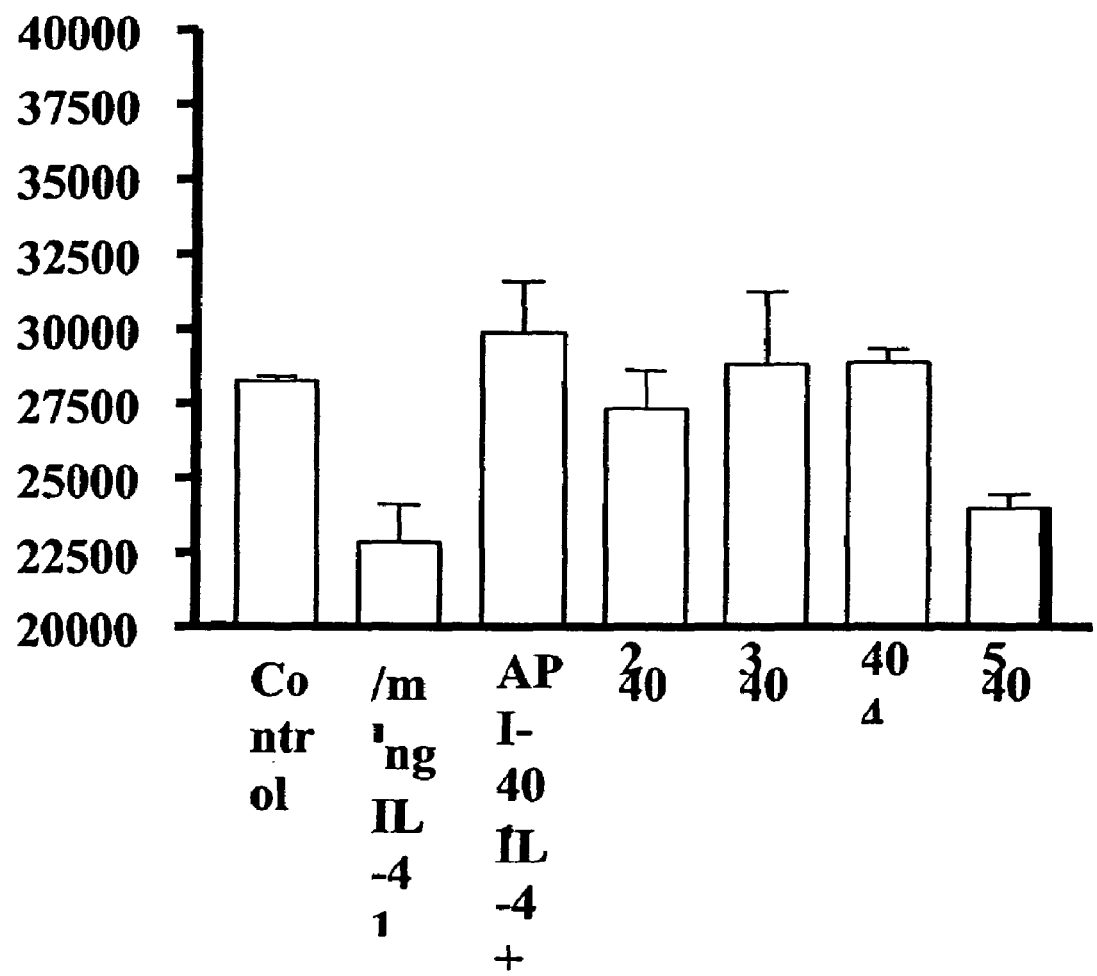
FIG. 10 graphically illustrates results of proliferation assays in carcinome A549 cells in presence of IL-4 (1 ng/ml) and various concentrations of the peptides API-401, API-402, API-403, API-404 and API-405.

As may be seen in FIG. 10, four out of five peptides prevented IL-4 from stopping proliferation in A549 carcinoma cells.

Further In vitro testing of the antagonists is conducted, as described in Table 3. In vivo experiments are described in Table 5.

TABLE 3

In vitro bioassays for IL-4R antagonist screening

| Cells | Type | Bioassay | Method |
|---|---|---|---|
| T helper | T helper cells | Proliferation Akt phosphorylation | $^3$H-Thymidine incorporation Western Blot |
| PAEC | Human pulmonary artery endothelial cells | VCAM-1 expression | Western blot |

EXAMPLE 4

Interleukin-1

Interleukin-1 (IL-1) plays a primary upstream role in the regulation of inflammation by stimulating generation of other inflammatory mediators and by enhancing the process of inflammation directly. Along with TNF, IL-1 is considered as a prototype for inflammatory cytokines. The effects of IL-1 are not limited to inflammation and this cytokine plays a role in bone formation and remodeling, insulin secretion and fever induction. IL-1 is also a major player in acute and chronic inflammation (e.g. septic shock, inflammatory bowel diseases, osteoarthritis, or rhumatoid arthritis), Alzheimer's disease and a number of autoimmune diseases. Monocytes are predominant sources of IL-1 but many other cell types express the protein: non-limiting examples include fibroblasts, endothelial cells, smooth muscle cells, osteoclasts, astrocytes, epithelial cells T-cells, B-cells and numerous cancer cells.

The interleukin-1 family of proteins consists of distinct but structurally related molecules: IL-1α, IL-1β, and IL-18 which elicit a biologic response and IL-1Ra, a naturally produced receptor antagonist. IL-1α is the predominant form in mice, IL-1β is predominant in human but both exert their effect through the same receptor. In addition, IL-1 induces the production of other inflammatory mediators like IL-6 and prostaglandin $PGE_2$ (induces COX-2 and PGE synthase expression) and induces proliferation and activation of numerous cell types.

As a major pro-inflammatory cytokine, IL-1 is a potentially powerful target for therapeutic interventions in diseases associated with articular cartilage injury such as in arthritis. Osteoarthritis and rhumatoid arthritis are only second to heart diseases for causing work disabilities in USA and their prevalence increase dramatically with age. Approximately 60 millions of American>40 years of age are at risk. In 1997, direct medical and disability costs for arthritis were approximately $75B (US). Other important disorders for which IL-1 contributes significantly include ulcerative colitis and Crohn's disease, which are also major causes of absenteeism in USA, and other types of auto-immune diseases.

Two distinct receptors of IL-1 have been cloned and characterized: IL-1R which generates the biological effects of IL-1, and IL-1RII which is a natural antagonist. In addition, a receptor accessory protein (IL-1RAcP), which is the putative signal-transducing subunit of the receptor complex has been identified. IL-1R type I is found mainly on T cells, keratinocytes, fibroblasts, chondrocytes, synoviocytes and epithelial cells. In order to generate a biological effect, IL-1R has to bind to IL-1 and subsequently to IL-1RacP which is necessary for signal transduction. The extracellular portion of IL-1R contains 3 Ig-like domains that bind IL-1. Of note, according to studies involving antibodies directed against extracellular portions of IL-1RacP, the latter does not interact with the cytokine and could therefore also be an excellent target for non-competitive peptidomimetic design.

Design of Peptides for IL-1R

The regions of the IL-1 receptor complex which were targeted are the third domain of IL-1R containing a flexible region and interacts with the accessory protein but not with the ligand. The equivalent domain on IL-1RacP, is the juxtamembranous regions of IL-1R and IL-1AcP and the regions between the second and third extracellular domains of IL-1RacP. The precise localization of these regions is described in Table 1 above along with exemplary sequences of subfragment peptides or modified peptides targeting one of these regions and presenting specificity to IL-1R.

Characterization of Peptides In Vitro and In Vivo

The affinity of the subfragment peptides or derivative is determined using binding studies on cells expressing or over-expressing IL-1R. The selectivity is tested by performing bioassays on cells expressing receptors from the same family as IL-1R (e.g. IL-18R) and the specificity is tested against receptors of another family of cytokine.

The proliferation effect of IL-1 was measured in A549 carcinoma cells in the presence of peptides API101; API103 and API106 and of IL-1 (10 ng/ml-Panel A) and (1 ng/ml-Panel B) pursuant to the incorporated tritiated thymidine method. The cells were preincubated at 37° C. with the different peptides at different concentrations, namely $10^{-6}$, $10^{-5}$ and $10^{-4}$ M. They were then incubated with IL-1 (10 ng/ml or 1 ng/ml) for 24 hours. The cells were then contacted with $^3$H-Thymidine for 24 hours, washed and lysed. The radioactivity was then measured with a scintillation counter. The sequences of the peptides antagonists used are as follows: API-101 APRYTVELA, API-103 MKLPVHKLY; and API-106 VGSPKNAVPPV. They generally correspond to the subfragment peptides having sequences SEQ ID NO: 50, NO: 52 and NO: 53, respectively except where the subfragment peptide contained an isoleucine. In that case, this isoleucine was replaced by a conservative leucine in the synthesized peptide for economic reasons.

As may be seen in panels A and B of FIG. 9, the peptides completely abrogated IL-1 induced proliferation in A549 carcinoma cells with an $EC_{50}$ of $10^{-6}$M for API-101 and 103; and of $10^{-5}$M for API-106.

The goal of the next experiment was to verify if the identified peptides can reverse the physiological actions of the natural cytokine in vivo either by injecting them through the jugular or directly in the stomach (to verify the stability of the peptide through the digestive tractus). 300 g Sprague-Dawley rats were anesthetized with isoflurane (2.5-4%). IL-1β was injected through the jugular. Blood was taken from the carotid for further analyses before and after (10 minutes) every injection. Peptides were then injected either directly in the stomach with a catheter or in the jugular at the concentration desired. Arterial blood pressure and other physiological characteristics were monitered at all time.

A severe hypotension induced by IL-1β was observed when administrated to the rats by either ways mentioned above. The following peptides constitute examples of antagonists that were able to prevent hypotension:

API-101.10 (target: juxtamembranous portion of the accessory protein of IL-1R, derivative of API-101):

1) When administrated by jugular injection after IL-1β injection (5 ug/kg) it prevented hypotension by 95% at a concentration of $10^{-8}$M. This demonstrated that the peptide has an hypotensor effect in vivo in animals by reversing the effect of IL-1β (data not shown).

2) When administrated directly into the stomach, the peptide at a concentration of $10^{-5}$M, reduced IL-1β induced hypotension by 60%. This result demonstrated that oral administration of the 101.10 peptide still maintained a major effect on IL-1β induced hypotension. (Data not shown)

In another experiment, vasomotricity variation of piglets pial vessels was studied to further evaluate the particular effect of cytokine receptor subfragments on the vasodilatator effect of IL-1β. Brains were dissected from Yorkshire piglets. Slices of brain exposing the pial vessels were pinned to a wax base of a 20 ml bath containing Krebs buffer (pH 7.4) equilibrated with 95% $O_2$-5% $CO_2$ and maintained at 37° C. Microvessels were visualized and recorded using a video camera mounted on a dissecting microscope. Vascular diameter was measured using a digital image analyzer and the images were recorded before and after topical application of constricting agent U46619 at $10^{-7}$M. After stabilization of the vasomotricity, IL-1β was added until stabilization of vasodilatation. Peptides were then injected at different concentrations from $10^{-10}$ to $10^{-5}$M. Reversal of vasodilatation (i.e. vasoconstriction) was visualized and measured as previously mentioned. IL-1β induced vasodilatation in the microvasculature of the piglet brain was observed. Examples of the inhibitory activity of cytokine subfragment peptides are given below:

1) API-101 and 101.10 (Juxtamembranous part of accessory protein) could prevent the vasodilation induced by IL-1β (75 ng/ml) with an $IC_{50}$ of 182 nM (API-101) and 10.8 nM (API-101.10). The range of concentrations of the peptide administered was from $10^{-10}$ to $10^{-5}$ M (data not shown)

2) API-108 (hinge Ig-3 region of accessory protein) could prevent vasodilatation with an $IC_{50}$ of 1.9 nM (data not shown). The range of concentrations of the peptide administered was from $10^{-10}$ to $10^{-5}$ M.

These results demonstrate that targeting of two flexible regions of one component of the receptor we could prevent IL-1 β activity at a very low $IC_{50}$ and therefore with a very high efficiency.

Another way of assessing the effect of cytokine receptor subfragments on IL-1R activity in vivo is by measuring $PGE_2$ levels in rat blood serum. Rat blood samples were collected from in vivo experiments (e.g. Protocol for IL-1 induced hypotension) and centrifuged at maximum speed for 15 minutes. The serum was then passed through a Waters column in order to isolate the lipidic part. Samples were evaporated and $PGE_2$ quantities were determined with an RIA assay using a commercial kit (Cederlane).

If the cytokine receptor subfragment peptides can prevent hypotention in vivo they should be able to prevent also the synthesis of $PGE_2$. The prostaglandin was therefore measured in serum of rats used for experiments mentioned above (e.g. Arterial Blood Pressure variation measurement). An example of results obtained with a particular cytokine receptor subfragment peptide is described below:

1) API-101.10 could prevent $PGE_2$ synthesis in vivo by 80% when the peptide was injected in the jugular. The same results were obtained when the peptide was injected directly in the stomach (data not shown).

These experiments demonstrate that the identified peptides derived from different flexible regions of a cytokine receptor (in this particular example, receptor IL-1R/IL-1RacP) are efficient and very potent in vitro and an vivo at reversing various biological effects of IL-1β.

From these experiments the efficiency and specificity of the method used to select particular cytokine subfragment peptides to modulate cytokine receptor activity is clearly demonstrated. Furthermore, the particular experiments presented above (with the IL-1R/IL-1RacP receptors) serves as a complete example of how one can select a particular cytokine receptor subfragment peptide (derivitize and/or protect it if desired), test its modulating activity in vitro and than its efficiency and potency in vivo. It also demonstrate that the modulating activities demonstrated in vitro are translatable to the in vivo situation.

The stability and selectivity of the peptides in vitro and in vivo is further verified with the tests described in Table 4, and Table 5 below, respectively.

TABLE 4

In vitro bioassays for IL-1R antagonist screening

| Cells | Type | Bioassay | Method |
|---|---|---|---|
| Chondrocytes | Human chondrocytes | $PGE_2$ levels<br>IL-6<br>Proliferation<br>Collagenase expression | RIA kit<br>RIA kit<br>$^3$H-Thymidine incorporation<br>Western Blot |
| RPE | Human retinal pigment epithelial cells | Same as above | Same as above |
| Thymocytes | EL4 - Mouse thymocytes -High IL1R expression | Proliferation | $^3$H-Thymidine incorporation |
| Fibroblasts | Human F7100 | Proliferation | $^3$H-Thymidine incorporation |

Table 5 summarizes the nature of the in vivo experiments performed with various peptides of the present invention. They are presented in more details below.

TABLE 5

In vivo experiments to assess efficacy and specificity of antagonists against IL-1R, IGF-1R and IL-4R

| Target | Animal model | Method | Treatment | Parameters |
|---|---|---|---|---|
| IL-1R | Collagen-induced arthritis in rat | s.c. injections of type II collagen in incomplete Freund's adjuvant | Following onset of arthritis, continuous delivery of the drug via osmotic pump | Destruction of cartilage assessed by histological staining and digital imaging |
| | Arterial blood pressure variation measurement in rats | Injection of IL-1b in jgular | 10 minutes following IL-1b, injection of peptide | Blood pressure variation measurements |

TABLE 5-continued

In vivo experiments to assess efficacy and specificity
of antagonists against IL-1R, IGF-1R and IL-4R

| Target | Animal model | Method | Treatment | Parameters |
|---|---|---|---|---|
| | Vasomotricity experiment on piglet pial vessels | Topical application of U46619 agent as vasoconstrictor than, IL-1b as a vasodilatator | antagonist in jugular or stomach. Following U46619 induced vasodilatation, application of peptide antagonist in microvessels | Vascular diameters |
| | $PGE_2$ levels in rat blood serum | Injection of IL-1b in jugular | injection of peptide antagonist in jugular or stomach and measurement of $PGE_2$ levels by RIA kit | $PGE_2$ levels |
| | Acute septic shock in rat | LPS-induced septic shock | Preceding i.v. bolus of LPS the animal will receive an i.v. bolus of the antagonist | Blood pressure, body temperature and cardiac rhythm will be monitored during the whole experiment (60 min) |
| IGF-IR | Tumor growth in immunosuppressed mouse (nude mouse) | s.c. injection of tumoral cell line | Continuous delivery of the antagonist with osmotic pump after latency to obtain solid tumor | Tumor size monitoring |
| IL-4R | Sensitization of the airways in newborn mice | Exposure of the animals ovalbumin (i.p. injection and aerosolized) | i.p. injection of receptor antagonist | IgE and TNF-γ dosage |

Acute Septic Shock in Rats

The efficiency of the peptides is also verified with the acute septic shock in Sprague-Dawley rat. Sprague-Dawley (160-180 gm) rats (Charles River) are anesthesed with a solution 9:1 xelazine/ketamine at a concentration of 1 mg/Kg. A tracheotomy is performed so as to maintain ventilation with a tube linked to a respirator. A cannula is inserted into the right carotide artery to enable monitoring of the systemic arterial with a Stratham pressure transducer linked to a multichannel Gould apparatus. The right jugular vein is cannuled to enable drug administration. The animal is placed under radial heat to maintain a constant normal temperature. The septic shock is obtained by systemic injection of a lipopolysaccharide bolus (LPS) (1 mg/kg: Sigma). A decrease of about 30 mm Hg is observed after ~5 minutes.

Collagen-Induced Arthritis Protocol in Lewis Rat

Type II Collagen (CII) that has been isolated and purified from bovine articulary is obtained from Sigma. CII (2 mg/ml) is dissolved over night at 4° C. with agitation in 0.01 M acetic acid. The solution is then emulsified in an incomplete Freund's adjuvant (CII: ICFA, Difco Laboratories, Detroit, Mich.). Lewis female rats (Charles River) of 140-180 gm and of 8 week old are immunised with 0.5 ml of the emulsion (0.5 mg CII) with many intradermal injections in the back and one or two injections in the tail base. The animals are then reinjected 7 days later in the tail base with 0.2 ml (0.2 mg CII) so as to obtain an acute inflammatory reaction. A different time points during the experiment (1 to 24 days) animals are sacrificed and knuckle joints samples are taken to be fixed and coated so as to enable cryosections of 6-7 μm. A double coloration of Goldner and toluidine blue is performed on slides to measure the importance of the articular inflammation. Digitalised images are taken and analysed with the Image Pro Plus™ 4.1 software.

Tumor Growth in Immunosuppressed Mouse (Nude Mouse)

The colon Colo 205™ carcinoma cell line is obtained from the American Type Culture Collection (ATCC: Rockville, Md.). Cells are maintained in a RPMI-1640 culture and grown in 100 mm Petri at 37° C. in a humidified atmosphere controlled to maintain 5% CO2 and 95% air. The medium is supplemented with 10% FCS, 2 mM L-glutamine, 100 U/ml penicillin and 100 μg/ml streptomycin.

$2.5 \times 10^6$ carcinoma colon Colo 205™ cells in 100 μl de PBS are injected subcutaneously in the back (needle 25 G: BD, NJ) in 6 weeks old immunodeficient female mice (Balb/c, nu/nu: Charles River). Treatment begins 5 days after injection of tumorous cells measuring ~0.5×0.5 cm. the tumour volume is measured every two days according to the following formula: length×width×height, with a vernier caliper. 14 days after the beginning of treatments, animals are sacrificed and tumours are sampled to be weighted and measured in volume. Specimens are then fixed in a 10% formalin buffer for 24H and then transferred in 70% ethanol. Tumours are then coated with paraffin and sections are cut for immunohistochemistry purposes. The general morphology is evaluated with a hematoxyline/eosin coloration.

Although the present invention has been described hereinabove by way of specific embodiments thereof, it can be modified, without departing from the spirit and nature of the subject invention as defined in the appended claims. In particular, although the flexible regions of all cytokines have not all been described herein nor have all peptidic extracellular non competitive modulators encompassed by the present invention targeting these regions have been described, in light of the procedure described above for screening peptides and identifying peptides of the present invention, a person of ordinary skill in the art would be able to rapidly develop peptidic modulators of cytokine receptor by selecting peptides of 5 to 20 amino acid derived from known flexible regions of cytokines.

REFERENCES

Christine Piossek et al. "Vascular Endothelial Growth Factor (VEGF) Receptor II-derived Peptides Inhibit VEGF" *The Journal of Biological Chemistry* vol. 274, No. 9, Feb. 26, 1999, pp. 5612-5619.

Daren C. W. Tan et al "A small peptide derived from flt-1 (VEGFR-1) functions as an angiogenic inhibitor" *FEBS Letters* 494 (2001) 150-156.

Guy Vigers et al. "X-Ray Crystal Structure of a Small Antagonist Peptide Bound to Interleukin-1Receptor Type 1" *The Journal of Biological Chemistry* vol. 275, No. 47, Nov. 24, 2000, pp. 36927-36933.

Do-Young Yoon et al. "Antibodies to domains II and III of the IL-1Receptor Accessory Protein Inhibit IL-1β Activity But Not Binding: Regulation of IL-1 Responses Is Via Type I Receptor, Not the Accessory Protein" *Journal of Immunology,* 1998.

What is claimed is:

1. A non-competitive extracellular cytokine receptor antagonist, wherein said antagonist consists of the amino acid sequence EATVGERVRL (SEQ ID NO:2), and wherein contacting a cell expressing a vascular endothelial growth factor receptor (VEGFR) with said antagonist decreases VEGF-induced proliferation of said cell relative to a control cell not contacted with said antagonist or inhibits VEGF-induced neovascularization relative to a control not contacted with said antagonist.

2. A method of inhibiting human VEGFR activity in a cell, said method comprising contacting a cell with a peptide, wherein said peptide consists of the amino acid sequence EATVGERVRL (SEQ ID NO:2), wherein said peptide inhibiting VEGFR activity is characterized by a decrease in VEGF-induced proliferation of said cell relative to a control cell not contacted with said peptide.

3. The method of claim 2, wherein said decrease in proliferation comprises inhibition of VEGF-induced neovascularization.

* * * * *

SEQUENCE LISTING

```
<160> NUMBER OF SEQ ID NOS: 65

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Gly Val Leu Ile Ile Ile Glu Leu Asn Thr Lys Glu Gln Ala
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Glu Ala Thr Val Gly Glu Arg Val Arg Leu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Leu Pro Leu Glu Ser Asn His Thr Leu Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence:  Synthetic
```

-continued

```
      Peptide

<400> SEQUENCE: 4

Ser Pro Val Asp Ser Tyr Gln Tyr Gly Thr Thr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Val Ile Leu Thr Asn Pro Ile Ser Lys Glu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 6

Asn Lys Val Gly Arg Gly Glu Arg Val Ile
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Met Pro Pro Thr Glu Gln Glu Ser Val
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 8

Arg Lys Thr Lys Lys Arg His Cys Val
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 9

Thr Val Leu Glu Arg Val Ala Pro Thr
1               5

<210> SEQ ID NO 10
```

<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Thr Ser Ile Gly Glu Ser Ile Glu Val
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Ser Ile Phe Val Pro Arg Pro Glu Arg Lys
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Asn Phe Leu His Asn Ser Ile Phe Val
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Glu Gly Pro Cys Pro Lys Val Cys Glu
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Glu Ser Asp Val Leu His Phe Thr Ser Thr
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

```
Arg Thr Asn Ala Ser Val Pro Ser Ile
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Ile Arg Lys Tyr Ala Asp Gly Thr Ile
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Glu Asn Phe Ile His Leu Ile Ile Ala
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Ala Lys Thr Gly Tyr Glu Asn Phe Ile His
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Lys Glu Arg Thr Val Ile Ser Asn Leu Arg
1               5                   10

<210> SEQ ID NO 20
<211> LENGTH: 1356
<212> TYPE: PRT
<213> ORGANISM: Homo sapiens

<400> SEQUENCE: 20

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60
```

```
Asn Asn Gln Ser Gly Ser Glu Gln Arg Val Glu Val Thr Glu Cys Ser
 65                  70                  75                  80

Asp Gly Leu Phe Cys Lys Thr Leu Thr Ile Pro Lys Val Ile Gly Asn
             85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
```

-continued

Ile Glu Val Asn Lys Asn Gln Phe Ala Leu Ile Glu Gly Lys Asn Lys
            485                 490                 495
                500                 505                 510

Thr Val Ser Thr Leu Val Ile Gln Ala Ala Asn Val Ser Ala Leu Tyr
                515                 520                 525

Lys Cys Glu Ala Val Asn Lys Val Gly Arg Gly Glu Arg Val Ile Ser
            530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
            595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Ile Leu
            755                 760                 765

Val Gly Thr Ala Val Ile Ala Met Phe Phe Trp Leu Leu Leu Val Ile
            770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
            835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910

```
Met Val Ile Val Glu Phe Cys Lys Phe Gly Asn Leu Ser Thr Tyr Leu
        915                 920                 925

Arg Ser Lys Arg Asn Glu Phe Val Pro Tyr Lys Thr Lys Gly Ala Arg
        930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ala Ser Ser Gly
                965                 970                 975

Phe Val Glu Glu Lys Ser Leu Ser Asp Val Glu Glu Glu Ala Pro
            980                 985                 990

Glu Asp Leu Tyr Lys Asp Phe Leu Thr Leu Glu His Leu Ile Cys Tyr
            995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305
```

-continued

```
Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 21
<211> LENGTH: 569
<212> TYPE: PRT
<213> ORGANISM: Homo sapiens

<400> SEQUENCE: 21

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
                20                  25                  30

Val Ser Ser Ala Asn Glu Ile Asp Val Arg Pro Cys Pro Leu Asn Pro
            35                  40                  45

Asn Glu His Lys Gly Thr Ile Thr Trp Tyr Lys Asp Asp Ser Lys Thr
        50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320
```

```
Asp Ala Ala Tyr Ile Gln Leu Ile Tyr Pro Val Thr Asn Phe Gln Lys
            325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
            355                 360                 365

Asp Ser Cys Tyr Asp Phe Leu Pro Ile Lys Ala Ser Asp Gly Lys Thr
            370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
            405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
            435                 440                 445

Arg Leu Ile Ile Ile Leu Val Arg Glu Thr Ser Gly Phe Ser Trp Leu
            450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
            485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
            515                 520                 525

Arg Phe Trp Lys Asn Val Arg Tyr His Met Pro Val Gln Arg Arg Ser
            530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
            565

<210> SEQ ID NO 22
<211> LENGTH: 570
<212> TYPE: PRT
<213> ORGANISM: Homo sapiens

<400> SEQUENCE: 22

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
            35                  40                  45

Leu Phe Glu His Phe Leu Lys Phe Asn Tyr Ser Thr Ala His Ser Ala
            50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
            85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
```

-continued

```
               115                 120                 125
Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Val Ile Pro
                180                 185                 190

Glu Gly Met Asn Leu Ser Phe Leu Ile Ala Leu Ile Ser Asn Gly
                195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
                260                 265                 270

Leu Met Asp Ser Arg Asn Glu Val Trp Trp Thr Ile Asp Gly Lys Lys
                275                 280                 285

Pro Asp Asp Ile Thr Ile Asp Val Thr Ile Asn Glu Ser Ile Ser His
                290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
                340                 345                 350

Ala Pro Arg Tyr Thr Val Glu Leu Ala Cys Gly Phe Gly Ala Thr Val
                355                 360                 365

Leu Leu Val Val Ile Leu Ile Val Val Tyr His Val Tyr Trp Leu Glu
                370                 375                 380

Met Val Leu Phe Tyr Arg Ala His Phe Gly Thr Asp Glu Thr Ile Leu
385                 390                 395                 400

Asp Gly Lys Glu Tyr Asp Ile Tyr Val Ser Tyr Ala Arg Asn Ala Glu
                405                 410                 415

Glu Glu Glu Phe Val Leu Leu Thr Leu Arg Gly Val Leu Glu Asn Glu
                420                 425                 430

Phe Gly Tyr Lys Leu Cys Ile Phe Asp Arg Asp Ser Leu Pro Gly Gly
                435                 440                 445

Ile Val Thr Asp Glu Thr Leu Ser Phe Ile Gln Lys Ser Arg Arg Leu
                450                 455                 460

Leu Val Val Leu Ser Pro Asn Tyr Val Leu Gln Gly Thr Gln Ala Leu
465                 470                 475                 480

Leu Glu Leu Lys Ala Gly Leu Glu Asn Met Ala Ser Arg Gly Asn Ile
                485                 490                 495

Asn Val Ile Leu Val Gln Tyr Lys Ala Val Lys Glu Thr Lys Val Lys
                500                 505                 510

Glu Leu Lys Arg Ala Lys Thr Val Leu Thr Val Ile Lys Trp Lys Gly
                515                 520                 525

Glu Lys Ser Lys Tyr Pro Gln Gly Arg Phe Trp Lys Gln Leu Gln Val
                530                 535                 540
```

-continued

```
Ala Met Pro Val Lys Lys Ser Pro Arg Arg Ser Ser Asp Glu Gln
545                 550                 555                 560

Gly Leu Ser Tyr Ser Ser Leu Lys Asn Val
                565                 570

<210> SEQ ID NO 23
<211> LENGTH: 1367
<212> TYPE: PRT
<213> ORGANISM: Homo sapiens

<400> SEQUENCE: 23

Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
```

-continued

```
            340                 345                 350
Cys Thr Ile Phe Lys Gly Asn Leu Leu Ile Asn Ile Arg Arg Gly Asn
            355                 360                 365
Asn Ile Ala Ser Glu Leu Glu Asn Phe Met Gly Leu Ile Glu Val Val
            370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Gln Leu Glu Gly
            405                 410                 415
Asn Tyr Ser Phe Tyr Val Leu Asp Asn Gln Asn Leu Gln Gln Leu Trp
            420                 425                 430
Asp Trp Asp His Arg Asn Leu Thr Ile Lys Ala Gly Lys Met Tyr Phe
            435                 440                 445
Ala Phe Asn Pro Lys Leu Cys Val Ser Glu Ile Tyr Arg Met Glu Glu
            450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
            485                 490                 495
Ser Thr Thr Thr Ser Lys Asn Arg Ile Ile Ile Thr Trp His Arg Tyr
            500                 505                 510
Arg Pro Pro Asp Tyr Arg Asp Leu Ile Ser Phe Thr Val Tyr Tyr Lys
            515                 520                 525
Glu Ala Pro Phe Lys Asn Val Thr Glu Tyr Asp Gly Gln Asp Ala Cys
            530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
            565                 570                 575
Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
            595                 600                 605
Ser Val Pro Ser Ile Pro Leu Asp Val Leu Ser Ala Ser Asn Ser Ser
            610                 615                 620
Ser Gln Leu Ile Val Lys Trp Asn Pro Pro Ser Leu Pro Asn Gly Asn
625                 630                 635                 640
Leu Ser Tyr Tyr Ile Val Arg Trp Gln Arg Gln Pro Gln Asp Gly Tyr
            645                 650                 655
Leu Tyr Arg His Asn Tyr Cys Ser Lys Asp Lys Ile Pro Ile Arg Lys
            660                 665                 670
Tyr Ala Asp Gly Thr Ile Asp Ile Glu Glu Val Thr Glu Asn Pro Lys
            675                 680                 685
Thr Glu Val Cys Gly Gly Glu Lys Gly Pro Cys Cys Ala Cys Pro Lys
            690                 695                 700
Thr Glu Ala Glu Lys Gln Ala Glu Lys Glu Glu Ala Glu Tyr Arg Lys
705                 710                 715                 720
Val Phe Glu Asn Phe Leu His Asn Ser Ile Phe Val Pro Arg Pro Glu
            725                 730                 735
Arg Lys Arg Arg Asp Val Met Gln Val Ala Asn Thr Thr Met Ser Ser
            740                 745                 750
Arg Ser Arg Asn Thr Thr Ala Ala Asp Thr Tyr Asn Ile Thr Asp Pro
            755                 760                 765
```

-continued

```
Glu Glu Leu Glu Thr Glu Tyr Pro Phe Phe Glu Ser Arg Val Asp Asn
    770             775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
                835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
                900                 905                 910

Asn Gly Ser Trp Thr Asp Pro Val Phe Phe Tyr Val Gln Ala Lys Thr
                915                 920                 925

Gly Tyr Glu Asn Phe Ile His Leu Ile Ile Ala Leu Pro Val Ala Val
    930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
                995                 1000                1005

Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
    1040                1045                1050

Met Lys Glu Phe Asn Cys His His Val Val Arg Leu Leu Gly Val
    1055                1060                1065

Val Ser Gln Gly Gln Pro Thr Leu Val Ile Met Glu Leu Met Thr
    1070                1075                1080

Arg Gly Asp Leu Lys Ser Tyr Leu Arg Ser Leu Arg Pro Glu Met
    1085                1090                1095

Glu Asn Asn Pro Val Leu Ala Pro Pro Ser Leu Ser Lys Met Ile
    1100                1105                1110

Gln Met Ala Gly Glu Ile Ala Asp Gly Met Ala Tyr Leu Asn Ala
    1115                1120                1125

Asn Lys Phe Val His Arg Asp Leu Ala Ala Arg Asn Cys Met Val
    1130                1135                1140

Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Gly Lys Gly Leu
    1160                1165                1170
```

```
Leu Pro Val Arg Trp Met Ser Pro Glu Ser Leu Lys Asp Gly Val
    1175                1180                1185

Phe Thr Thr Tyr Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Ile Lys Glu Glu Met Glu Pro Gly Phe Arg Glu Val Ser
    1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His Ser Gly His
    1310                1315                1320

Lys Ala Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
    1355                1360                1365

<210> SEQ ID NO 24
<211> LENGTH: 825
<212> TYPE: PRT
<213> ORGANISM: Homo sapiens

<400> SEQUENCE: 24

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175
```

```
Val Thr Tyr Leu Glu Pro Ser Leu Arg Ile Ala Ser Thr Leu Lys
            180                 185                 190

Ser Gly Ile Ser Tyr Arg Ala Arg Val Arg Ala Trp Ala Gln Cys Tyr
            195                 200                 205

Asn Thr Thr Trp Ser Glu Trp Ser Pro Ser Thr Lys Trp His Asn Ser
            210                 215                 220

Tyr Arg Glu Pro Phe Glu Gln His Leu Leu Gly Val Ser Val Ser
225                 230                 235                 240

Cys Ile Val Ile Leu Ala Val Cys Leu Leu Cys Tyr Val Ser Ile Thr
                245                 250                 255

Lys Ile Lys Lys Glu Trp Trp Asp Gln Ile Pro Asn Pro Ala Arg Ser
                260                 265                 270

Arg Leu Val Ala Ile Ile Gln Asp Ala Gln Gly Ser Gln Trp Glu
            275                 280                 285

Lys Arg Ser Arg Gly Gln Glu Pro Ala Lys Cys Pro His Trp Lys Asn
            290                 295                 300

Cys Leu Thr Lys Leu Leu Pro Cys Phe Leu Glu His Asn Met Lys Arg
305                 310                 315                 320

Asp Glu Asp Pro His Lys Ala Ala Lys Glu Met Pro Phe Gln Gly Ser
                325                 330                 335

Gly Lys Ser Ala Trp Cys Pro Val Glu Ile Ser Lys Thr Val Leu Trp
                340                 345                 350

Pro Glu Ser Ile Ser Val Val Arg Cys Val Glu Leu Phe Glu Ala Pro
                355                 360                 365

Val Glu Cys Glu Glu Glu Glu Val Glu Glu Glu Lys Gly Ser Phe
            370                 375                 380

Cys Ala Ser Pro Glu Ser Ser Arg Asp Asp Phe Gln Glu Gly Arg Glu
385                 390                 395                 400

Gly Ile Val Ala Arg Leu Thr Glu Ser Leu Phe Leu Asp Leu Leu Gly
                405                 410                 415

Glu Glu Asn Gly Gly Phe Cys Gln Gln Asp Met Gly Glu Ser Cys Leu
                420                 425                 430

Leu Pro Pro Ser Gly Ser Thr Ser Ala His Met Pro Trp Asp Glu Phe
                435                 440                 445

Pro Ser Ala Gly Pro Lys Glu Ala Pro Pro Trp Gly Lys Glu Gln Pro
            450                 455                 460

Leu His Leu Glu Pro Ser Pro Pro Ala Ser Pro Thr Gln Ser Pro Asp
465                 470                 475                 480

Asn Leu Thr Cys Thr Glu Thr Pro Leu Val Ile Ala Gly Asn Pro Ala
                485                 490                 495

Tyr Arg Ser Phe Ser Asn Ser Leu Ser Gln Ser Pro Cys Pro Arg Glu
                500                 505                 510

Leu Gly Pro Asp Pro Leu Leu Ala Arg His Leu Glu Glu Val Glu Pro
            515                 520                 525

Glu Met Pro Cys Val Pro Gln Leu Ser Glu Pro Thr Thr Val Pro Gln
530                 535                 540

Pro Glu Pro Glu Thr Trp Glu Gln Ile Leu Arg Arg Asn Val Leu Gln
545                 550                 555                 560

His Gly Ala Ala Ala Ala Pro Val Ser Ala Pro Thr Ser Gly Tyr Gln
                565                 570                 575

Glu Phe Val His Ala Val Glu Gln Gly Gly Thr Gln Ala Ser Ala Val
            580                 585                 590
```

-continued

Val Gly Leu Gly Pro Pro Gly Glu Ala Gly Tyr Lys Ala Phe Ser Ser
        595                 600                 605

Leu Leu Ala Ser Ser Ala Val Ser Pro Glu Lys Cys Gly Phe Gly Ala
        610                 615                 620

Ser Ser Gly Glu Glu Gly Tyr Lys Pro Phe Gln Asp Leu Ile Pro Gly
625                 630                 635                 640

Cys Pro Gly Asp Pro Ala Pro Val Pro Leu Phe Thr Phe Gly
                645                 650                 655

Leu Asp Arg Glu Pro Pro Arg Ser Pro Gln Ser Ser His Leu Pro Ser
            660                 665                 670

Ser Ser Pro Glu His Leu Gly Leu Glu Pro Gly Glu Lys Val Glu Asp
        675                 680                 685

Met Pro Lys Pro Pro Leu Pro Gln Glu Gln Ala Thr Asp Pro Leu Val
    690                 695                 700

Asp Ser Leu Gly Ser Gly Ile Val Tyr Ser Ala Leu Thr Cys His Leu
705                 710                 715                 720

Cys Gly His Leu Lys Gln Cys His Gly Gln Glu Asp Gly Gly Gln Thr
                725                 730                 735

Pro Val Met Ala Ser Pro Cys Cys Gly Cys Cys Cys Gly Asp Arg Ser
            740                 745                 750

Ser Pro Pro Thr Thr Pro Leu Arg Ala Pro Asp Pro Ser Pro Gly Gly
        755                 760                 765

Val Pro Leu Glu Ala Ser Leu Cys Pro Ala Ser Leu Ala Pro Ser Gly
    770                 775                 780

Ile Ser Glu Lys Ser Lys Ser Ser Ser Phe His Pro Ala Pro Gly
785                 790                 795                 800

Asn Ala Gln Ser Ser Ser Gln Thr Pro Lys Ile Val Asn Phe Val Ser
                805                 810                 815

Val Gly Pro Thr Tyr Met Arg Val Ser
            820                 825

<210> SEQ ID NO 25
<211> LENGTH: 569
<212> TYPE: PRT
<213> ORGANISM: Homo sapiens

<400> SEQUENCE: 25

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

-continued

```
Met Glu Phe Phe Lys Asn Glu Asn Glu Leu Pro Lys Leu Gln Trp
145                 150                 155                 160

Tyr Lys Asp Cys Lys Pro Leu Leu Asp Asn Ile His Phe Ser Gly
            165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
        210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
            245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
        290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
            325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
        355                 360                 365

Asp Ser Cys Tyr Asp Phe Leu Pro Ile Lys Ala Ser Asp Gly Lys Thr
        370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
            405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
        435                 440                 445

Arg Leu Ile Ile Ile Leu Val Arg Glu Thr Ser Gly Phe Ser Trp Leu
450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
            485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
        515                 520                 525

Arg Phe Trp Lys Asn Val Arg Tyr His Met Pro Val Gln Arg Arg Ser
        530                 535                 540

Pro Ser Ser Lys His Gln Leu Leu Ser Pro Ala Thr Lys Glu Lys Leu
545                 550                 555                 560
```

Gln Arg Glu Ala His Val Pro Leu Gly
              565

<210> SEQ ID NO 26
<211> LENGTH: 576
<212> TYPE: PRT
<213> ORGANISM: Mus sp.

<400> SEQUENCE: 26

Met Glu Asn Met Lys Val Leu Leu Gly Leu Ile Cys Leu Met Val Pro
1               5                   10                  15

Leu Leu Ser Leu Glu Ile Asp Val Cys Thr Glu Tyr Pro Asn Gln Ile
            20                  25                  30

Val Leu Phe Leu Ser Val Asn Glu Ile Asp Ile Arg Lys Cys Pro Leu
        35                  40                  45

Thr Pro Asn Lys Met His Gly Asp Thr Ile Ile Trp Tyr Lys Asn Asp
    50                  55                  60

Ser Lys Thr Pro Ile Ser Ala Asp Arg Asp Ser Arg Ile His Gln Gln
65                  70                  75                  80

Asn Glu His Leu Trp Phe Val Pro Ala Lys Val Glu Asp Ser Gly Tyr
                85                  90                  95

Tyr Tyr Cys Ile Val Arg Asn Ser Thr Tyr Cys Leu Lys Thr Lys Val
            100                 105                 110

Thr Val Thr Val Leu Glu Asn Asp Pro Gly Leu Cys Tyr Ser Thr Gln
        115                 120                 125

Ala Thr Phe Pro Gln Arg Leu His Ile Ala Gly Asp Gly Ser Leu Val
    130                 135                 140

Cys Pro Tyr Val Ser Tyr Phe Lys Asp Glu Asn Asn Glu Leu Pro Glu
145                 150                 155                 160

Val Gln Trp Tyr Lys Asn Cys Lys Pro Leu Leu Leu Asp Asn Val Ser
                165                 170                 175

Phe Phe Gly Val Lys Asp Lys Leu Leu Val Arg Asn Val Ala Glu Glu
            180                 185                 190

His Arg Gly Asp Tyr Ile Cys Arg Met Ser Tyr Thr Phe Arg Gly Lys
        195                 200                 205

Gln Tyr Pro Val Thr Arg Val Ile Gln Phe Ile Thr Ile Asp Glu Asn
    210                 215                 220

Lys Arg Asp Arg Pro Val Ile Leu Ser Pro Arg Asn Glu Thr Ile Glu
225                 230                 235                 240

Ala Asp Pro Gly Ser Met Ile Gln Leu Ile Cys Asn Val Thr Gly Gln
                245                 250                 255

Phe Ser Asp Leu Val Tyr Trp Lys Trp Asn Gly Ser Glu Ile Glu Trp
            260                 265                 270

Asn Asp Pro Phe Leu Ala Glu Asp Tyr Gln Phe Val Glu His Pro Ser
        275                 280                 285

Thr Lys Arg Lys Tyr Thr Leu Ile Thr Thr Leu Asn Ile Ser Glu Val
    290                 295                 300

Lys Ser Gln Phe Tyr Arg Tyr Pro Phe Ile Cys Val Val Lys Asn Thr
305                 310                 315                 320

Asn Ile Phe Glu Ser Ala His Val Gln Leu Ile Tyr Pro Val Pro Asp
                325                 330                 335

Phe Lys Asn Tyr Leu Ile Gly Gly Phe Ile Ile Leu Thr Ala Thr Ile
            340                 345                 350

Val Cys Cys Val Cys Ile Tyr Lys Val Phe Lys Val Asp Ile Val Leu
        355                 360                 365

```
Trp Tyr Arg Asp Ser Cys Ser Gly Phe Leu Pro Ser Lys Ala Ser Asp
    370                 375                 380

Gly Lys Thr Tyr Asp Ala Tyr Ile Leu Tyr Pro Lys Thr Leu Gly Glu
385                 390                 395                 400

Gly Ser Phe Ser Asp Leu Asp Thr Phe Val Phe Lys Leu Leu Pro Glu
                405                 410                 415

Val Leu Glu Gly Gln Phe Gly Tyr Lys Leu Phe Ile Tyr Gly Arg Asp
                420                 425                 430

Asp Tyr Val Gly Glu Asp Thr Ile Glu Val Thr Asn Glu Asn Val Lys
        435                 440                 445

Lys Ser Arg Arg Leu Ile Ile Ile Leu Val Arg Asp Met Gly Gly Phe
450                 455                 460

Ser Trp Leu Gly Gln Ser Ser Glu Glu Gln Ile Ala Ile Tyr Asn Ala
465                 470                 475                 480

Leu Ile Gln Glu Gly Ile Lys Ile Val Leu Leu Glu Leu Glu Lys Ile
                485                 490                 495

Gln Asp Tyr Glu Lys Met Pro Asp Ser Ile Gln Phe Ile Lys Gln Lys
                500                 505                 510

His Gly Val Ile Cys Trp Ser Gly Asp Phe Gln Glu Arg Pro Gln Ser
        515                 520                 525

Ala Lys Thr Arg Phe Trp Lys Asn Leu Arg Tyr Gln Met Pro Ala Gln
530                 535                 540

Arg Arg Ser Pro Leu Ser Lys His Arg Leu Leu Thr Leu Asp Pro Val
545                 550                 555                 560

Arg Asp Thr Lys Glu Lys Leu Pro Ala Ala Thr His Leu Pro Leu Gly
                565                 570                 575

<210> SEQ ID NO 27
<211> LENGTH: 576
<212> TYPE: PRT
<213> ORGANISM: Rattus sp.

<400> SEQUENCE: 27

Met Glu Asn Met Lys Val Leu Leu Gly Phe Ile Cys Leu Ile Val Pro
1               5                   10                  15

Leu Leu Ser Leu Glu Thr Asp Lys Cys Thr Glu Tyr Pro Asn Glu Val
                20                  25                  30

Ile Ser Phe Ser Ser Val Asn Glu Ile Asp Ile Arg Ser Cys Pro Leu
            35                  40                  45

Thr Pro Asn Glu Met His Gly Gly Thr Ile Ile Trp Tyr Lys Asn Asp
        50                  55                  60

Ser Lys Thr Pro Ile Ser Ala Asp Lys Asp Ser Arg Ile His Gln Gln
65                  70                  75                  80

Asn Glu His Leu Trp Phe Val Pro Ala Lys Met Glu Asp Ser Gly Tyr
                85                  90                  95

Tyr Tyr Cys Ile Met Arg Asn Ser Thr Tyr Cys Leu Lys Thr Lys Ile
                100                 105                 110

Thr Met Ser Val Leu Glu Asn Asp Pro Gly Leu Cys Tyr Asn Thr Gln
            115                 120                 125

Ala Ser Phe Ile Gln Arg Leu His Val Ala Gly Asp Gly Ser Leu Val
        130                 135                 140

Cys Pro Tyr Leu Asp Phe Phe Lys Asp Glu Asn Asn Glu Leu Pro Lys
145                 150                 155                 160

Val Gln Trp Tyr Lys Asn Cys Lys Pro Leu Pro Leu Asp Asp Gly Asn
```

-continued

```
                165                 170                 175
Phe Phe Gly Phe Lys Asn Lys Leu Met Val Met Asn Val Ala Glu Glu
            180                 185                 190

His Arg Gly Asn Tyr Thr Cys Arg Thr Ser Tyr Thr Tyr Gln Gly Lys
            195                 200                 205

Gln Tyr Pro Val Thr Arg Val Ile Thr Phe Ile Thr Ile Asp Asp Ser
            210                 215                 220

Lys Arg Asp Arg Pro Val Ile Met Ser Pro Arg Asn Glu Thr Met Glu
225                 230                 235                 240

Ala Asp Pro Gly Ser Thr Ile Gln Leu Ile Cys Asn Val Thr Gly Gln
            245                 250                 255

Phe Thr Asp Leu Val Tyr Trp Lys Trp Asn Gly Ser Glu Ile Glu Trp
            260                 265                 270

Asp Asp Pro Ile Leu Ala Glu Asp Tyr Gln Phe Leu Glu His Pro Ser
            275                 280                 285

Ala Lys Arg Lys Tyr Thr Leu Ile Thr Thr Leu Asn Val Ser Glu Val
            290                 295                 300

Lys Ser Gln Phe Tyr Arg Tyr Pro Phe Ile Cys Phe Val Lys Asn Thr
305                 310                 315                 320

His Ile Leu Glu Thr Ala His Val Arg Leu Val Tyr Pro Val Pro Asp
            325                 330                 335

Phe Lys Asn Tyr Leu Ile Gly Gly Phe Ala Ile Phe Thr Ala Thr Ala
            340                 345                 350

Val Phe Cys Ala Cys Ile Tyr Lys Val Phe Lys Val Asp Ile Val Leu
            355                 360                 365

Trp Tyr Arg Asp Ser Cys Ser Asp Phe Leu Pro Arg Lys Ala Ser Asp
            370                 375                 380

Gly Arg Thr Tyr Asp Ala Tyr Val Leu Tyr Pro Lys Thr Tyr Gly Glu
385                 390                 395                 400

Gly Ser Phe Ala Tyr Leu Asp Thr Phe Val Phe Lys Leu Leu Pro Glu
            405                 410                 415

Val Leu Glu Gly Gln Phe Gly Tyr Lys Leu Phe Ile Cys Gly Arg Asp
            420                 425                 430

Asp Tyr Val Gly Glu Asp Thr Ile Glu Val Thr Asn Glu Asn Val Lys
            435                 440                 445

Arg Ser Arg Arg Leu Ile Ile Ile Leu Val Arg Asp Met Gly Ser Phe
            450                 455                 460

Ser Cys Leu Gly Gln Ser Ser Glu Glu Gln Ile Ala Ile Tyr Asp Ala
465                 470                 475                 480

Leu Ile Arg Glu Gly Ile Lys Ile Ile Leu Leu Glu Leu Glu Lys Ile
            485                 490                 495

Gln Asp Tyr Glu Lys Met Pro Glu Ser Ile Gln Phe Ile Lys Gln Lys
            500                 505                 510

His Gly Ala Ile Cys Trp Ser Gly Asp Phe Lys Glu Arg Pro Gln Ser
            515                 520                 525

Ala Lys Thr Arg Phe Trp Lys Asn Leu Arg Tyr Gln Met Pro Ala Gln
            530                 535                 540

Arg Arg Ser Pro Leu Ser Lys His His Leu Leu Thr Leu Asp Pro Val
545                 550                 555                 560

Leu Asp Thr Lys Glu Lys Leu Gln Ala Glu Thr His Leu Pro Leu Gly
            565                 570                 575
```

<210> SEQ ID NO 28

```
<211> LENGTH: 555
<212> TYPE: PRT
<213> ORGANISM: Equus sp.

<400> SEQUENCE: 28

Met His Lys Met Thr Ser Thr Phe Leu Leu Ile Gly His Leu Ile Leu
1               5                   10                  15

Leu Ile Pro Leu Phe Ser Ala Glu Glu Cys Val Ile Cys Asn Tyr Phe
            20                  25                  30

Val Leu Val Gly Glu Pro Thr Ala Ile Ser Cys Pro Val Ile Thr Leu
        35                  40                  45

Pro Met Leu His Ser Asp Tyr Asn Leu Thr Trp Tyr Arg Asn Gly Ser
50                  55                  60

Asn Met Pro Ile Thr Thr Glu Arg Arg Ala Arg Ile His Gln Arg Lys
65                  70                  75                  80

Gly Leu Leu Trp Phe Ile Pro Ala Ala Leu Glu Asp Ser Gly Leu Tyr
                85                  90                  95

Glu Cys Glu Val Arg Ser Leu Asn Arg Ser Lys Gln Lys Ile Ile Asn
            100                 105                 110

Leu Lys Val Phe Lys Asn Asp Asn Gly Leu Cys Phe Asn Gly Glu Met
        115                 120                 125

Lys Tyr Asp Gln Ile Val Lys Ser Ala Asn Ala Gly Lys Ile Ile Cys
130                 135                 140

Pro Asp Leu Glu Asn Phe Lys Asp Glu Asp Asn Ile Asn Pro Glu Ile
145                 150                 155                 160

His Trp Tyr Lys Glu Cys Lys Ser Gly Phe Leu Glu Asp Lys Arg Leu
                165                 170                 175

Val Leu Ala Glu Gly Glu Asn Ala Ile Leu Ile Leu Asn Val Thr Ile
            180                 185                 190

Gln Asp Lys Gly Asn Tyr Thr Cys Arg Met Val Tyr Thr Tyr Met Gly
        195                 200                 205

Lys Gln Tyr Asn Val Ser Arg Thr Met Asn Leu Glu Val Lys Glu Ser
210                 215                 220

Pro Leu Lys Met Arg Pro Glu Phe Ile Tyr Pro Asn Asn Asn Thr Ile
225                 230                 235                 240

Glu Val Glu Leu Gly Ser His Val Val Met Glu Cys Asn Val Ser Ser
                245                 250                 255

Gly Val Tyr Gly Leu Leu Pro Tyr Trp Gln Val Asn Asp Glu Asp Val
            260                 265                 270

Asp Ser Phe Asp Ser Thr Tyr Arg Glu Gln Phe Tyr Glu Glu Gly Met
        275                 280                 285

Pro His Gly Ile Ala Val Ser Gly Thr Lys Phe Asn Ile Ser Glu Val
290                 295                 300

Lys Leu Lys Asp Tyr Ala Tyr Lys Phe Phe Cys His Phe Ile Tyr Asp
305                 310                 315                 320

Ser Gln Glu Phe Thr Ser Tyr Ile Lys Leu Glu His Pro Val Gln Asn
                325                 330                 335

Ile Arg Gly Tyr Leu Ile Gly Gly Ile Ser Leu Ile Phe Leu Leu
            340                 345                 350

Phe Leu Ile Leu Ile Val Tyr Lys Ile Phe Lys Ile Asp Ile Val Leu
        355                 360                 365

Trp Tyr Arg Ser Ser Cys His Pro Leu Leu Gly Lys Lys Val Ser Asp
370                 375                 380

Gly Lys Ile Tyr Asp Ala Tyr Val Leu Tyr Pro Lys Asn Arg Glu Ser
```

```
                385                 390                 395                 400
Cys Leu Tyr Ser Ser Asp Ile Phe Ala Leu Lys Ile Leu Pro Glu Val
                405                 410                 415

Leu Glu Arg Gln Cys Gly Tyr Asn Leu Phe Ile Phe Gly Arg Asn Asp
            420                 425                 430

Leu Ala Gly Glu Ala Val Ile Asp Val Thr Asp Glu Lys Ile His Gln
            435                 440                 445

Ser Arg Arg Val Ile Ile Ile Leu Val Pro Glu Pro Ser Cys Tyr Gly
        450                 455                 460

Ile Leu Glu Asp Ala Ser Glu Lys His Leu Ala Val Tyr Asn Ala Leu
465                 470                 475                 480

Ile Gln Asp Gly Ile Lys Ile Ile Leu Ile Glu Leu Glu Lys Ile Glu
                485                 490                 495

Asp Tyr Ala Asn Met Pro Glu Ser Ile Lys Tyr Val Lys Gln Lys Tyr
                500                 505                 510

Gly Ala Ile Arg Trp Thr Gly Asp Phe Ser Glu Arg Ser His Ser Ala
            515                 520                 525

Ser Thr Arg Phe Trp Lys Lys Val Arg Tyr His Met Pro Ser Arg Lys
        530                 535                 540

His Gly Ser Ser Ser Gly Phe His Leu Ser Ser
545                 550                 555

<210> SEQ ID NO 29
<211> LENGTH: 825
<212> TYPE: PRT
<213> ORGANISM: Homo sapiens

<400> SEQUENCE: 29

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr
        195                 200                 205
```

-continued

```
Asn Thr Thr Trp Ser Glu Trp Ser Pro Ser Thr Lys Trp His Asn Ser
210                 215                 220
Tyr Arg Glu Pro Phe Glu Gln His Leu Leu Leu Gly Val Ser Val Ser
225                 230                 235                 240
Cys Ile Val Ile Leu Ala Val Cys Leu Leu Cys Tyr Val Ser Ile Thr
                245                 250                 255
Lys Ile Lys Lys Glu Trp Trp Asp Gln Ile Pro Asn Pro Ala Arg Ser
            260                 265                 270
Arg Leu Val Ala Ile Ile Gln Asp Ala Gln Gly Ser Gln Trp Glu
        275                 280                 285
Lys Arg Ser Arg Gly Gln Glu Pro Ala Lys Cys Pro His Trp Lys Asn
290                 295                 300
Cys Leu Thr Lys Leu Leu Pro Cys Phe Leu Glu His Asn Met Lys Arg
305                 310                 315                 320
Asp Glu Asp Pro His Lys Ala Ala Lys Glu Met Pro Phe Gln Gly Ser
                325                 330                 335
Gly Lys Ser Ala Trp Cys Pro Val Glu Ile Ser Lys Thr Val Leu Trp
            340                 345                 350
Pro Glu Ser Ile Ser Val Val Arg Cys Val Glu Leu Phe Glu Ala Pro
        355                 360                 365
Val Glu Cys Glu Glu Glu Glu Val Glu Glu Lys Gly Ser Phe
370                 375                 380
Cys Ala Ser Pro Glu Ser Ser Arg Asp Asp Phe Gln Glu Gly Arg Glu
385                 390                 395                 400
Gly Ile Val Ala Arg Leu Thr Glu Ser Leu Phe Leu Asp Leu Leu Gly
                405                 410                 415
Glu Glu Asn Gly Gly Phe Cys Gln Gln Asp Met Gly Glu Ser Cys Leu
            420                 425                 430
Leu Pro Pro Ser Gly Ser Thr Ser Ala His Met Pro Trp Asp Glu Phe
        435                 440                 445
Pro Ser Ala Gly Pro Lys Glu Ala Pro Pro Trp Gly Lys Glu Gln Pro
450                 455                 460
Leu His Leu Glu Pro Ser Pro Ala Ser Pro Thr Gln Ser Pro Asp
465                 470                 475                 480
Asn Leu Thr Cys Thr Glu Thr Pro Leu Val Ile Ala Gly Asn Pro Ala
                485                 490                 495
Tyr Arg Ser Phe Ser Asn Ser Leu Ser Gln Ser Pro Cys Pro Arg Glu
            500                 505                 510
Leu Gly Pro Asp Pro Leu Leu Ala Arg His Leu Glu Glu Val Glu Pro
        515                 520                 525
Glu Met Pro Cys Val Pro Gln Leu Ser Glu Pro Thr Thr Val Pro Gln
530                 535                 540
Pro Glu Pro Glu Thr Trp Glu Gln Ile Leu Arg Arg Asn Val Leu Gln
545                 550                 555                 560
His Gly Ala Ala Ala Pro Val Ser Ala Pro Thr Ser Gly Tyr Gln
                565                 570                 575
Glu Phe Val His Ala Val Glu Gln Gly Gly Thr Gln Ala Ser Ala Val
            580                 585                 590
Val Gly Leu Gly Pro Pro Gly Glu Ala Gly Tyr Lys Ala Phe Ser Ser
        595                 600                 605
Leu Leu Ala Ser Ser Ala Val Ser Pro Glu Lys Cys Gly Phe Gly Ala
610                 615                 620
Ser Ser Gly Glu Glu Gly Tyr Lys Pro Phe Gln Asp Leu Ile Pro Gly
```

```
                625                 630                 635                 640
Cys Pro Gly Asp Pro Ala Pro Val Pro Val Pro Leu Phe Thr Phe Gly
                    645                 650                 655

Leu Asp Arg Glu Pro Pro Arg Ser Pro Gln Ser Ser His Leu Pro Ser
                660                 665                 670

Ser Ser Pro Glu His Leu Gly Leu Glu Pro Gly Glu Lys Val Glu Asp
            675                 680                 685

Met Pro Lys Pro Pro Leu Pro Gln Glu Gln Ala Thr Asp Pro Leu Val
        690                 695                 700

Asp Ser Leu Gly Ser Gly Ile Val Tyr Ser Ala Leu Thr Cys His Leu
705                 710                 715                 720

Cys Gly His Leu Lys Gln Cys His Gly Gln Glu Asp Gly Gly Gln Thr
                725                 730                 735

Pro Val Met Ala Ser Pro Cys Cys Gly Cys Cys Gly Asp Arg Ser
                    740                 745                 750

Ser Pro Pro Thr Thr Pro Leu Arg Ala Pro Asp Pro Ser Pro Gly Gly
            755                 760                 765

Val Pro Leu Glu Ala Ser Leu Cys Pro Ala Ser Leu Ala Pro Ser Gly
        770                 775                 780

Ile Ser Glu Lys Ser Lys Ser Ser Ser Phe His Pro Ala Pro Gly
785                 790                 795                 800

Asn Ala Gln Ser Ser Ser Gln Thr Pro Lys Ile Val Asn Phe Val Ser
                805                 810                 815

Val Gly Pro Thr Tyr Met Arg Val Ser
            820                 825

<210> SEQ ID NO 30
<211> LENGTH: 9
<212> TYPE: PRT
<213> ORGANISM: Artificial
<220> FEATURE:
<223> OTHER INFORMATION: Peptide

<400> SEQUENCE: 30

Phe Val Phe Ala Arg Thr Met Pro Ala
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 31

Asn Gly Pro Lys Ile Pro Ser Ile Ala Thr
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 32

Ala Thr Gly Gln Val Cys His Ala Leu
1               5
```

```
<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 33

Arg Lys Val Cys Asn Gly Ile Gly Ile Gly Glu
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 34

Trp His Asn Ser Tyr Arg Glu Pro Phe
1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

Tyr Arg Glu Pro Phe Glu Gln His Leu Leu
1               5                   10

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 36

Ser Asp Thr Leu Leu Leu Thr Trp Ser
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 37

Ile Tyr Asn Val Thr Tyr Leu Glu
1               5

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 38

Ile Ala Ala Ser Thr Leu Lys Ser Gly Ile Ser
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 39

Lys Pro Ser Glu His Val Lys Pro Arg
1               5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 40

Phe Thr Cys Glu Glu Asp Phe Tyr Phe Pro Trp
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 41

Ser Val Asp Glu Ile Val Gln Pro Asp
1               5

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 42

Met Asp Pro Ile Asp Thr Thr Ser Val Pro Val Tyr
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 43

Ile Asp Ala Ala Tyr Ile Gln Leu Ile Tyr Pro Val
1               5                   10

<210> SEQ ID NO 44
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 44

Leu Ile Tyr Pro Val Thr Asn Phe Gln Lys His Met
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 45

Leu Glu Glu Asn Lys Pro Thr Arg Pro Val
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 46

Asn Lys Pro Thr Arg Pro Val Ile Val Ser
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 47

Val Ala Glu Lys His Arg Gly Asn Tyr Thr
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 48

Trp Asn Gly Ser Val Ile Asp Glu Asp
1               5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 49

Val Pro Ala Pro Arg Tyr Thr Val Glu Leu
1               5                   10
```

```
<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 50

Ala Pro Arg Tyr Thr Val Glu Leu Ala
1               5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 51

Val Gln Lys Asp Ser Cys Phe Asn Ser Pro Met
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 52

Met Lys Leu Pro Val His Lys Leu Tyr
1               5

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 53

Val Gly Ser Pro Lys Asn Ala Val Pro Pro Val
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 54

Val Thr Tyr Pro Glu Asn Gly Arg Thr Phe
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 55

Ile His Ser Pro Asn Asp His Val Val Tyr
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 56

Leu Ile Ser Asn Asn Gly Asn Tyr Thr
1               5

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 57

Val Trp Trp Thr Ile Asp Gly Lys Lys Pro Asp
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 58

Trp Thr Ile Asp Gly Lys Lys Pro Asp Asp Ile
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 59

His Ser Arg Thr Glu Asp Glu Thr Arg Thr Gln
1               5                   10

<210> SEQ ID NO 60
<211> LENGTH: 810
<212> TYPE: PRT
<213> ORGANISM: Mus sp.

<400> SEQUENCE: 60

Met Gly Arg Leu Cys Thr Lys Phe Leu Thr Ser Val Gly Cys Leu Ile
1               5                   10                  15

Leu Leu Leu Val Thr Gly Ser Gly Ser Ile Lys Val Leu Gly Glu Pro
            20                  25                  30

Thr Cys Phe Ser Asp Tyr Ile Arg Thr Ser Thr Cys Glu Trp Phe Leu
        35                  40                  45
```

-continued

```
Asp Ser Ala Val Asp Cys Ser Ser Gln Leu Cys Leu His Tyr Arg Leu
 50                  55                  60

Met Phe Phe Glu Phe Ser Glu Asn Leu Thr Cys Ile Pro Arg Asn Ser
 65                  70                  75                  80

Ala Ser Thr Val Cys Val Cys His Met Glu Met Asn Arg Pro Val Gln
                 85                  90                  95

Ser Asp Arg Tyr Gln Met Glu Leu Trp Ala Glu His Arg Gln Leu Trp
            100                 105                 110

Gln Gly Ser Phe Ser Pro Ser Gly Asn Val Lys Pro Leu Ala Pro Asp
        115                 120                 125

Asn Leu Thr Leu His Thr Asn Val Ser Asp Glu Trp Leu Leu Thr Trp
    130                 135                 140

Asn Asn Leu Tyr Pro Ser Asn Asn Leu Leu Tyr Lys Asp Leu Ile Ser
145                 150                 155                 160

Met Val Asn Ile Ser Arg Glu Asp Asn Pro Ala Glu Phe Ile Val Tyr
                165                 170                 175

Asn Val Thr Tyr Lys Glu Pro Arg Leu Ser Phe Pro Ile Asn Ile Leu
            180                 185                 190

Met Ser Gly Val Tyr Tyr Thr Ala Arg Val Arg Val Arg Ser Gln Ile
        195                 200                 205

Leu Thr Gly Thr Trp Ser Glu Trp Ser Pro Ser Ile Thr Trp Tyr Asn
    210                 215                 220

His Phe Gln Leu Pro Leu Ile Gln Arg Leu Pro Leu Gly Val Thr Ile
225                 230                 235                 240

Ser Cys Leu Cys Ile Pro Leu Phe Cys Leu Phe Cys Tyr Phe Ser Ile
                245                 250                 255

Thr Lys Ile Lys Lys Ile Trp Trp Asp Gln Ile Pro Thr Pro Ala Arg
            260                 265                 270

Ser Pro Leu Val Ala Ile Ile Ile Gln Asp Ala Gln Val Pro Leu Trp
        275                 280                 285

Asp Lys Gln Thr Arg Ser Gln Glu Ser Thr Lys Tyr Pro His Trp Lys
    290                 295                 300

Thr Cys Leu Asp Lys Leu Leu Pro Cys Leu Leu Lys His Arg Val Lys
305                 310                 315                 320

Lys Lys Thr Asp Phe Pro Lys Ala Ala Pro Thr Lys Ser Leu Gln Ser
                325                 330                 335

Pro Gly Lys Ala Gly Trp Cys Pro Met Glu Val Ser Arg Thr Val Leu
            340                 345                 350

Trp Pro Glu Asn Val Ser Val Ser Val Val Arg Cys Met Glu Leu Phe
        355                 360                 365

Glu Ala Pro Val Gln Asn Val Glu Glu Glu Asp Glu Ile Val Lys
    370                 375                 380

Glu Asp Leu Ser Met Ser Pro Glu Asn Ser Gly Gly Cys Gly Phe Gln
385                 390                 395                 400

Glu Ser Gln Ala Asp Ile Met Ala Arg Leu Thr Glu Asn Leu Phe Ser
                405                 410                 415

Asp Leu Leu Glu Ala Glu Asn Gly Gly Leu Gly Gln Ser Ala Leu Ala
            420                 425                 430

Glu Ser Cys Ser Pro Leu Pro Ser Gly Ser Gly Gln Ala Ser Val Ser
        435                 440                 445

Trp Ala Cys Leu Pro Met Gly Pro Ser Glu Glu Ala Thr Cys Gln Val
    450                 455                 460

Thr Glu Gln Pro Ser His Pro Gly Pro Leu Ser Gly Ser Pro Ala Gln
```

```
            465                 470                 475                 480

Ser Ala Pro Thr Leu Ala Cys Thr Gln Val Pro Leu Val Leu Ala Asp
                485                 490                 495

Asn Pro Ala Tyr Arg Ser Phe Ser Asp Cys Cys Ser Pro Ala Pro Asn
            500                 505                 510

Pro Gly Glu Leu Ala Pro Glu Gln Gln Ala Asp His Leu Glu Glu
        515                 520                 525

Glu Glu Pro Pro Ser Pro Ala Asp Pro His Ser Ser Gly Pro Pro Met
    530                 535                 540

Gln Pro Val Glu Ser Trp Glu Gln Ile Leu His Met Ser Val Leu Gln
545                 550                 555                 560

His Gly Ala Ala Gly Ser Thr Pro Ala Pro Ala Gly Gly Tyr Gln
            565                 570                 575

Glu Phe Val Gln Ala Val Lys Gln Gly Ala Ala Gln Asp Pro Gly Val
        580                 585                 590

Pro Gly Val Arg Pro Ser Gly Asp Pro Gly Tyr Lys Ala Phe Ser Ser
    595                 600                 605

Leu Leu Ser Ser Asn Gly Ile Arg Gly Asp Thr Ala Ala Ala Gly Thr
610                 615                 620

Asp Asp Gly His Gly Gly Tyr Lys Pro Phe Gln Asn Pro Val Pro Asn
625                 630                 635                 640

Gln Ser Pro Ser Ser Val Pro Leu Phe Thr Phe Gly Leu Asp Thr Glu
            645                 650                 655

Leu Ser Pro Ser Pro Leu Asn Ser Asp Pro Lys Ser Pro Pro Glu
        660                 665                 670

Cys Leu Gly Leu Glu Leu Gly Leu Lys Gly Gly Asp Trp Val Lys Ala
    675                 680                 685

Pro Pro Pro Ala Asp Gln Val Pro Lys Pro Phe Gly Asp Asp Leu Gly
690                 695                 700

Phe Gly Ile Val Tyr Ser Ser Leu Thr Cys His Leu Cys Gly His Leu
705                 710                 715                 720

Lys Gln His His Ser Gln Glu Glu Gly Gly Gln Ser Pro Ile Val Ala
            725                 730                 735

Ser Pro Gly Cys Gly Cys Cys Tyr Asp Asp Arg Ser Pro Ser Leu Gly
            740                 745                 750

Ser Leu Ser Gly Ala Leu Glu Ser Cys Pro Glu Gly Ile Pro Pro Glu
        755                 760                 765

Ala Asn Leu Met Ser Ala Pro Lys Thr Pro Ser Asn Leu Ser Gly Glu
    770                 775                 780

Gly Lys Gly Pro Gly His Ser Pro Val Pro Ser Gln Thr Thr Glu Val
785                 790                 795                 800

Pro Val Gly Ala Leu Gly Ile Ala Val Ser
            805                 810

<210> SEQ ID NO 61
<211> LENGTH: 810
<212> TYPE: PRT
<213> ORGANISM: Equus sp.

<400> SEQUENCE: 61

Met Gly Arg Leu Cys Thr Lys Phe Leu Thr Ser Val Gly Cys Leu Ile
1               5                   10                  15

Leu Leu Leu Val Thr Gly Ser Gly Ser Ile Lys Val Leu Gly Glu Pro
            20                  25                  30
```

-continued

```
Thr Cys Phe Ser Asp Tyr Ile Arg Thr Ser Thr Cys Glu Trp Phe Leu
        35                  40                  45

Asp Ser Ala Val Asp Cys Ser Ser Gln Leu Cys Leu His Tyr Arg Leu
        50                  55                  60

Met Phe Glu Phe Ser Glu Asn Leu Ile Cys Ile Pro Arg Asn Ser
 65                  70                  75                  80

Ala Ser Thr Val Cys Val Cys His Met Glu Met Asn Arg Pro Val Gln
                85                  90                  95

Ser Asp Arg Tyr Gln Met Glu Leu Trp Ala Glu His Arg Gln Leu Trp
            100                 105                 110

Gln Gly Ser Phe Ser Pro Ser Gly Asn Val Lys Pro Leu Ala Pro Asp
            115                 120                 125

Asn Leu Thr Leu His Thr Asn Val Ser Asp Glu Trp Leu Leu Thr Trp
        130                 135                 140

Asn Asn Leu Tyr Pro Ser Asn Asn Leu Leu Tyr Lys Asp Leu Ile Ser
145                 150                 155                 160

Met Val Asn Ile Ser Arg Glu Asp Asn Pro Ala Glu Phe Ile Val Tyr
                165                 170                 175

Asn Val Thr Tyr Lys Glu Pro Arg Leu Ser Phe Pro Ile Asn Ile Leu
            180                 185                 190

Met Ser Gly Val Tyr Tyr Thr Ala Arg Val Arg Val Arg Ser Gln Ile
            195                 200                 205

Leu Thr Gly Thr Trp Ser Glu Trp Ser Pro Ser Ile Thr Trp Tyr Asn
        210                 215                 220

His Phe Gln Leu Pro Leu Ile Gln Arg Leu Pro Leu Gly Val Thr Ile
225                 230                 235                 240

Ser Cys Leu Cys Ile Pro Leu Phe Cys Leu Phe Cys Tyr Phe Ser Ile
                245                 250                 255

Thr Lys Ile Lys Lys Ile Trp Trp Asp Gln Ile Pro Thr Pro Ala Arg
            260                 265                 270

Ser Pro Leu Val Ala Ile Ile Ile Gln Asp Ala Gln Val Pro Leu Trp
        275                 280                 285

Asp Lys Gln Thr Arg Ser Gln Glu Ser Thr Lys Tyr Pro His Trp Lys
        290                 295                 300

Thr Cys Leu Asp Lys Leu Leu Pro Cys Leu Leu Lys His Arg Val Lys
305                 310                 315                 320

Lys Lys Thr Asp Phe Pro Lys Ala Ala Pro Thr Lys Ser Pro Gln Ser
                325                 330                 335

Pro Gly Lys Ala Gly Trp Cys Pro Met Glu Val Ser Arg Thr Val Leu
            340                 345                 350

Trp Pro Glu Asn Val Ser Val Val Arg Cys Met Glu Leu Phe
            355                 360                 365

Glu Ala Pro Val Gln Asn Val Glu Glu Glu Asp Glu Ile Val Lys
        370                 375                 380

Glu Asp Leu Ser Met Ser Pro Glu Asn Ser Gly Cys Gly Phe Gln
385                 390                 395                 400

Glu Ser Gln Ala Asp Ile Met Ala Arg Leu Thr Glu Asn Leu Phe Ser
                405                 410                 415

Asp Leu Leu Glu Ala Glu Asn Gly Gly Leu Gly Gln Ser Ala Leu Ala
            420                 425                 430

Glu Ser Cys Ser Pro Leu Pro Ser Gly Ser Gly Gln Ala Ser Val Ser
            435                 440                 445

Trp Ala Cys Leu Pro Met Gly Pro Ser Glu Glu Ala Thr Cys Gln Val
```

-continued

```
               450                 455                 460
Thr Glu Gln Pro Ser His Pro Gly Pro Leu Ser Gly Ser Pro Ala Gln
465                 470                 475                 480

Ser Ala Pro Thr Leu Ala Cys Thr Gln Val Pro Leu Val Leu Ala Asp
                485                 490                 495

Asn Pro Ala Tyr Arg Ser Phe Ser Asp Cys Cys Ser Pro Ala Pro Asn
            500                 505                 510

Pro Gly Glu Leu Ala Pro Glu Gln Gln Gln Ala Asp His Leu Glu Glu
        515                 520                 525

Glu Glu Pro Pro Ser Pro Ala Asp Pro His Ser Ser Gly Pro Pro Met
530                 535                 540

Gln Pro Val Glu Ser Trp Glu Gln Ile Leu His Met Ser Val Leu Gln
545                 550                 555                 560

His Gly Ala Ala Ala Gly Ser Thr Pro Ala Pro Ala Gly Gly Tyr Gln
                565                 570                 575

Glu Phe Val Gln Ala Val Lys Gln Gly Ala Ala Gln Asp Pro Gly Val
            580                 585                 590

Pro Gly Val Arg Pro Ser Gly Asp Pro Gly Tyr Lys Ala Phe Ser Ser
        595                 600                 605

Leu Leu Ser Ser Asn Gly Ile Arg Gly Asp Thr Ala Ala Ala Gly Thr
    610                 615                 620

Asp Asp Gly His Gly Gly Tyr Lys Pro Phe Gln Asn Pro Val Pro Asn
625                 630                 635                 640

Gln Ser Pro Ser Ser Val Pro Leu Phe Thr Phe Gly Leu Asp Thr Glu
                645                 650                 655

Leu Ser Pro Ser Pro Leu Asn Ser Asp Pro Pro Lys Ser Pro Pro Glu
            660                 665                 670

Cys Leu Gly Leu Glu Leu Gly Leu Lys Gly Gly Asp Trp Val Lys Ala
        675                 680                 685

Pro Pro Pro Ala Asp Gln Val Pro Lys Pro Phe Gly Asp Asp Leu Gly
    690                 695                 700

Phe Gly Ile Val Tyr Ser Ser Leu Thr Cys His Leu Cys Gly His Leu
705                 710                 715                 720

Lys Gln His His Ser Gln Glu Glu Gly Gly Gln Ser Pro Ile Val Ala
                725                 730                 735

Ser Pro Gly Cys Gly Cys Cys Tyr Asp Asp Arg Ser Pro Ser Leu Gly
            740                 745                 750

Ser Leu Ser Gly Ala Leu Glu Ser Cys Pro Glu Gly Ile Pro Pro Glu
        755                 760                 765

Ala Asn Leu Met Ser Ala Pro Lys Thr Pro Ser Asn Leu Ser Gly Glu
    770                 775                 780

Gly Lys Gly Pro Gly His Ser Pro Val Pro Ser Gln Thr Thr Glu Val
785                 790                 795                 800

Pro Val Gly Ala Leu Gly Ile Ala Val Ser
                805                 810
```

<210> SEQ ID NO 62
<211> LENGTH: 1356
<212> TYPE: PRT
<213> ORGANISM: Homo sapiens

<400> SEQUENCE: 62

```
Met Gln Ser Lys Val Leu Leu Ala Val Ala Leu Trp Leu Cys Val Glu
1               5                   10                  15
```

-continued

```
Thr Arg Ala Ala Ser Val Gly Leu Pro Ser Val Ser Leu Asp Leu Pro
                 20              25              30

Arg Leu Ser Ile Gln Lys Asp Ile Leu Thr Ile Lys Ala Asn Thr Thr
             35              40              45

Leu Gln Ile Thr Cys Arg Gly Gln Arg Asp Leu Asp Trp Leu Trp Pro
     50              55              60

Asn Asn Gln Ser Gly Ser Glu Gln Arg Val Glu Val Thr Glu Cys Ser
 65              70              75              80

Asp Gly Leu Phe Cys Lys Thr Leu Thr Ile Pro Lys Val Ile Gly Asn
                 85              90              95

Asp Thr Gly Ala Tyr Lys Cys Phe Tyr Arg Glu Thr Asp Leu Ala Ser
                100             105             110

Val Ile Tyr Val Tyr Val Gln Asp Tyr Arg Ser Pro Phe Ile Ala Ser
                115             120             125

Val Ser Asp Gln His Gly Val Val Tyr Ile Thr Glu Asn Lys Asn Lys
130             135             140

Thr Val Val Ile Pro Cys Leu Gly Ser Ile Ser Asn Leu Asn Val Ser
145             150             155             160

Leu Cys Ala Arg Tyr Pro Glu Lys Arg Phe Val Pro Asp Gly Asn Arg
                165             170             175

Ile Ser Trp Asp Ser Lys Lys Gly Phe Thr Ile Pro Ser Tyr Met Ile
                180             185             190

Ser Tyr Ala Gly Met Val Phe Cys Glu Ala Lys Ile Asn Asp Glu Ser
                195             200             205

Tyr Gln Ser Ile Met Tyr Ile Val Val Val Gly Tyr Arg Ile Tyr
                210             215             220

Asp Val Val Leu Ser Pro Ser His Gly Ile Glu Leu Ser Val Gly Glu
225             230             235             240

Lys Leu Val Leu Asn Cys Thr Ala Arg Thr Glu Leu Asn Val Gly Ile
                245             250             255

Asp Phe Asn Trp Glu Tyr Pro Ser Ser Lys His Gln His Lys Lys Leu
                260             265             270

Val Asn Arg Asp Leu Lys Thr Gln Ser Gly Ser Glu Met Lys Lys Phe
                275             280             285

Leu Ser Thr Leu Thr Ile Asp Gly Val Thr Arg Ser Asp Gln Gly Leu
                290             295             300

Tyr Thr Cys Ala Ala Ser Ser Gly Leu Met Thr Lys Lys Asn Ser Thr
305             310             315             320

Phe Val Arg Val His Glu Lys Pro Phe Val Ala Phe Gly Ser Gly Met
                325             330             335

Glu Ser Leu Val Glu Ala Thr Val Gly Glu Arg Val Arg Ile Pro Ala
                340             345             350

Lys Tyr Leu Gly Tyr Pro Pro Pro Glu Ile Lys Trp Tyr Lys Asn Gly
                355             360             365

Ile Pro Leu Glu Ser Asn His Thr Ile Lys Ala Gly His Val Leu Thr
                370             375             380

Ile Met Glu Val Ser Glu Arg Asp Thr Gly Asn Tyr Thr Val Ile Leu
385             390             395             400

Thr Asn Pro Ile Ser Lys Glu Lys Gln Ser His Val Val Ser Leu Val
                405             410             415

Val Tyr Val Pro Pro Gln Ile Gly Glu Lys Ser Leu Ile Ser Pro Val
                420             425             430

Asp Ser Tyr Gln Tyr Gly Thr Thr Gln Thr Leu Thr Cys Thr Val Tyr
```

-continued

```
                435                 440                 445
Ala Ile Pro Pro His His Ile His Trp Tyr Trp Gln Leu Glu Glu
        450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
        500                 505                 510
Thr Val Ser Thr Leu Val Ile Gln Ala Ala Asn Val Ser Ala Leu Tyr
        515                 520                 525
Lys Cys Glu Ala Val Asn Lys Val Gly Arg Gly Glu Arg Val Ile Ser
530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
                580                 585                 590
Ile His Val Gly Glu Leu Pro Thr Pro Val Cys Lys Asn Leu Asp Thr
        595                 600                 605
Leu Trp Lys Leu Asn Ala Thr Met Phe Ser Asn Ser Thr Asn Asp Ile
        610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
Arg Gln Leu Thr Val Leu Glu Arg Val Ala Pro Thr Ile Thr Gly Asn
                660                 665                 670
Leu Glu Asn Gln Thr Thr Ser Ile Gly Glu Ser Ile Glu Val Ser Cys
        675                 680                 685
Thr Ala Ser Gly Asn Pro Pro Pro Gln Ile Met Trp Phe Lys Asp Asn
        690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                725                 730                 735
Cys Gln Ala Cys Ser Val Leu Gly Cys Ala Lys Val Glu Ala Phe Phe
                740                 745                 750
Ile Ile Glu Gly Ala Gln Glu Lys Thr Asn Leu Glu Ile Ile Ile Leu
        755                 760                 765
Val Gly Thr Ala Val Ile Ala Met Phe Phe Trp Leu Leu Leu Val Ile
        770                 775                 780
Ile Leu Arg Thr Val Lys Arg Ala Asn Gly Gly Glu Leu Lys Thr Gly
785                 790                 795                 800
Tyr Leu Ser Ile Val Met Asp Pro Asp Glu Leu Pro Leu Asp Glu His
                805                 810                 815
Cys Glu Arg Leu Pro Tyr Asp Ala Ser Lys Trp Glu Phe Pro Arg Asp
                820                 825                 830
Arg Leu Lys Leu Gly Lys Pro Leu Gly Arg Gly Ala Phe Gly Gln Val
        835                 840                 845
Ile Glu Ala Asp Ala Phe Gly Ile Asp Lys Thr Ala Thr Cys Arg Thr
        850                 855                 860
```

```
Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
                900                 905                 910

Met Val Ile Val Glu Phe Cys Lys Phe Gly Asn Leu Ser Thr Tyr Leu
                915                 920                 925

Arg Ser Lys Arg Asn Glu Phe Val Pro Tyr Lys Thr Lys Gly Ala Arg
930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ala Ser Ser Gly
                965                 970                 975

Phe Val Glu Glu Lys Ser Leu Ser Asp Val Glu Glu Glu Ala Pro
                980                 985                 990

Glu Asp Leu Tyr Lys Asp Phe Leu Thr Leu Glu His Leu Ile Cys Tyr
                995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260
```

```
Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 63
<211> LENGTH: 1367
<212> TYPE: PRT
<213> ORGANISM: Mus sp.

<400> SEQUENCE: 63

Met Glu Ser Lys Ala Leu Leu Ala Val Ala Leu Trp Phe Cys Val Glu
1               5                   10                  15

Thr Arg Ala Ala Ser Val Gly Leu Pro Gly Asp Phe Leu His Pro Pro
                20                  25                  30

Lys Leu Ser Thr Gln Lys Asp Ile Leu Thr Ile Leu Ala Asn Thr Thr
            35                  40                  45

Leu Gln Ile Thr Cys Arg Gly Gln Arg Asp Leu Asp Trp Leu Trp Pro
    50                  55                  60

Asn Ala Gln Arg Asp Ser Glu Glu Arg Val Leu Val Thr Glu Cys Gly
65                  70                  75                  80

Gly Gly Asp Ser Ile Phe Cys Lys Thr Leu Thr Ile Pro Arg Val Val
                85                  90                  95

Gly Asn Asp Thr Gly Ala Tyr Lys Cys Ser Tyr Arg Asp Val Asp Ile
            100                 105                 110

Ala Ser Thr Val Tyr Val Tyr Val Arg Asp Tyr Arg Ser Pro Phe Ile
        115                 120                 125

Ala Ser Val Ser Asp Gln His Gly Ile Val Tyr Ile Thr Glu Asn Lys
    130                 135                 140

Asn Lys Thr Val Val Ile Pro Cys Arg Gly Ser Ile Ser Asn Leu Asn
145                 150                 155                 160

Val Ser Leu Cys Ala Arg Tyr Pro Glu Lys Arg Phe Val Pro Asp Gly
                165                 170                 175

Asn Arg Ile Ser Trp Asp Ser Glu Ile Gly Phe Thr Leu Pro Ser Tyr
            180                 185                 190

Met Ile Ser Tyr Ala Gly Met Val Phe Cys Glu Ala Lys Ile Asn Asp
        195                 200                 205

Glu Thr Tyr Gln Ser Ile Met Tyr Ile Val Val Val Gly Tyr Arg
    210                 215                 220

Ile Tyr Asp Val Ile Leu Ser Pro His Glu Ile Glu Leu Ser Ala
225                 230                 235                 240

Gly Glu Lys Leu Val Leu Asn Cys Thr Ala Arg Thr Glu Leu Asn Val
                245                 250                 255

Gly Leu Asp Phe Thr Trp His Ser Pro Pro Ser Lys Ser His His Lys
            260                 265                 270
```

-continued

```
Lys Ile Val Asn Arg Asp Val Lys Pro Phe Pro Gly Thr Val Ala Lys
            275                 280                 285

Met Phe Leu Ser Thr Leu Thr Ile Glu Ser Val Thr Lys Ser Asp Gln
        290                 295                 300

Gly Glu Tyr Thr Cys Val Ala Ser Ser Gly Arg Met Ile Lys Arg Asn
305                 310                 315                 320

Arg Thr Phe Val Arg Val His Thr Lys Pro Phe Ile Ala Phe Gly Ser
                325                 330                 335

Gly Met Lys Ser Leu Val Glu Ala Thr Val Gly Ser Gln Val Arg Ile
            340                 345                 350

Pro Val Lys Tyr Leu Ser Tyr Pro Ala Pro Asp Ile Lys Trp Tyr Arg
            355                 360                 365

Asn Gly Arg Pro Ile Glu Ser Asn Tyr Thr Met Ile Val Gly Asp Glu
        370                 375                 380

Leu Thr Ile Met Glu Val Thr Glu Arg Asp Ala Gly Asn Tyr Thr Val
385                 390                 395                 400

Ile Leu Thr Asn Pro Ile Ser Met Glu Lys Gln Ser His Met Val Ser
                405                 410                 415

Leu Val Val Asn Val Pro Pro Gln Ile Gly Glu Lys Ala Leu Ile Ser
            420                 425                 430

Pro Met Asp Ser Tyr Gln Tyr Gly Thr Met Gln Thr Leu Thr Cys Thr
            435                 440                 445

Val Tyr Ala Asn Pro Pro Leu His His Ile Gln Trp Tyr Trp Gln Leu
        450                 455                 460

Glu Glu Ala Cys Ser Tyr Arg Pro Gly Gln Thr Ser Pro Tyr Ala Cys
465                 470                 475                 480

Lys Glu Trp Arg His Val Glu Asp Phe Gln Gly Asn Lys Ile Glu
                485                 490                 495

Val Thr Lys Asn Gln Tyr Ala Leu Ile Glu Gly Lys Asn Lys Thr Val
            500                 505                 510

Ser Thr Leu Val Ile Gln Ala Ala Asn Val Ser Ala Leu Tyr Lys Cys
        515                 520                 525

Glu Ala Ile Asn Lys Ala Gly Arg Gly Glu Arg Val Ile Ser Phe His
    530                 535                 540

Val Ile Arg Gly Pro Glu Ile Thr Val Gln Pro Ala Ala Gln Pro Thr
545                 550                 555                 560

Glu Gln Glu Ser Val Ser Leu Leu Cys Thr Ala Asp Arg Asn Thr Phe
                565                 570                 575

Glu Asn Leu Thr Trp Tyr Lys Leu Gly Ser Gln Ala Thr Ser Val His
            580                 585                 590

Met Gly Glu Ser Leu Thr Pro Val Cys Lys Asn Leu Asp Ala Leu Trp
        595                 600                 605

Lys Leu Asn Gly Thr Met Phe Ser Asn Ser Thr Asn Asp Ile Leu Ile
    610                 615                 620

Val Ala Phe Gln Asn Ala Ser Leu Gln Asp Gln Gly Asp Tyr Val Cys
625                 630                 635                 640

Ser Ala Gln Asp Lys Lys Thr Lys Lys Arg His Cys Leu Val Lys Gln
                645                 650                 655

Leu Ile Ile Leu Glu Arg Met Ala Pro Met Ile Thr Gly Asn Leu Glu
            660                 665                 670

Asn Gln Thr Thr Thr Ile Gly Glu Thr Ile Glu Val Thr Cys Pro Ala
        675                 680                 685
```

-continued

```
Ser Gly Asn Pro Thr Pro His Ile Thr Trp Phe Lys Asp Asn Glu Thr
690                 695                 700

Leu Val Glu Asp Ser Gly Ile Val Leu Arg Asp Gly Asn Arg Asn Leu
705                 710                 715                 720

Thr Ile Arg Arg Val Arg Lys Glu Asp Gly Gly Leu Tyr Thr Cys Gln
            725                 730                 735

Ala Cys Asn Val Leu Gly Cys Ala Arg Ala Glu Thr Leu Phe Ile Ile
            740                 745                 750

Glu Gly Ala Gln Glu Lys Thr Asn Leu Glu Val Ile Ile Leu Val Gly
            755                 760                 765

Thr Ala Val Ile Ala Met Phe Phe Trp Leu Leu Leu Val Ile Leu Val
770                 775                 780

Arg Thr Val Lys Arg Ala Asn Glu Gly Glu Leu Lys Thr Gly Tyr Leu
785                 790                 795                 800

Ser Ile Val Met Asp Pro Asp Glu Leu Pro Leu Asp Glu Arg Cys Glu
            805                 810                 815

Arg Leu Pro Tyr Asp Ala Ser Lys Trp Glu Phe Pro Arg Asp Arg Leu
            820                 825                 830

Lys Leu Gly Lys Pro Leu Gly Arg Gly Ala Phe Gly Gln Val Ile Glu
            835                 840                 845

Ala Asp Ala Phe Gly Ile Asp Lys Thr Ala Thr Cys Lys Thr Val Ala
850                 855                 860

Val Lys Met Leu Lys Glu Gly Ala Thr His Ser Glu His Arg Ala Leu
865                 870                 875                 880

Met Ser Glu Leu Lys Ile Leu Ile His Ile Gly His His Leu Asn Val
                885                 890                 895

Val Asn Leu Leu Gly Ala Cys Thr Lys Pro Gly Gly Pro Leu Met Val
            900                 905                 910

Ile Val Glu Phe Ser Lys Phe Gly Asn Leu Ser Thr Tyr Leu Arg Gly
            915                 920                 925

Lys Arg Asn Glu Phe Val Pro Tyr Lys Ser Lys Gly Ala Arg Phe Arg
930                 935                 940

Gln Gly Lys Asp Tyr Val Gly Glu Leu Ser Val Asp Leu Lys Arg Arg
945                 950                 955                 960

Leu Asp Ser Ile Thr Ser Ser Gln Ser Ser Ala Ser Ser Gly Phe Val
            965                 970                 975

Glu Glu Lys Ser Leu Ser Asp Val Glu Glu Glu Ala Ser Glu Glu
            980                 985                 990

Leu Tyr Lys Asp Phe Leu Thr Leu Glu His Leu Ile Cys Tyr Ser Phe
            995                 1000                1005

Gln Val Ala Lys Gly Met Glu Phe Leu Ala Ser Arg Lys Cys Ile
    1010            1015            1020

His Arg Asp Leu Ala Ala Arg Asn Ile Leu Leu Ser Glu Lys Asn
    1025            1030            1035

Val Val Lys Ile Cys Asp Phe Gly Leu Ala Arg Asp Ile Tyr Lys
    1040            1045            1050

Asp Pro Asp Tyr Val Arg Lys Gly Asp Ala Arg Leu Pro Leu Lys
    1055            1060            1065

Trp Met Ala Pro Glu Thr Ile Phe Asp Arg Val Tyr Thr Ile Gln
    1070            1075            1080

Ser Asp Val Trp Ser Phe Gly Val Leu Leu Trp Glu Ile Phe Ser
    1085            1090            1095

Leu Gly Ala Ser Pro Tyr Pro Gly Val Lys Ile Asp Glu Glu Phe
```

```
                    1100                1105                1110

Cys Arg Arg Leu Lys Glu Gly Thr Arg Met Arg Ala Pro Asp Tyr
        1115                1120                1125

Thr Thr Pro Glu Met Tyr Gln Thr Met Leu Asp Cys Trp His Glu
        1130                1135                1140

Asp Pro Asn Gln Arg Pro Ser Phe Ser Glu Leu Val Glu His Leu
        1145                1150                1155

Gly Asn Leu Leu Gln Ala Asn Ala Gln Asp Gly Lys Asp Tyr
        1160                1165                1170

Ile Val Leu Pro Met Ser Glu Thr Leu Ser Met Glu Glu Asp Ser
        1175                1180                1185

Gly Leu Ser Leu Pro Thr Ser Pro Val Ser Cys Met Glu Glu Glu
        1190                1195                1200

Glu Val Cys Asp Pro Lys Phe His Tyr Asp Asn Thr Ala Gly Ile
        1205                1210                1215

Ser His Tyr Leu Gln Asn Ser Lys Arg Lys Ser Arg Pro Val Ser
        1220                1225                1230

Val Lys Thr Phe Glu Asp Ile Pro Leu Glu Glu Pro Glu Val Lys
        1235                1240                1245

Val Ile Pro Asp Asp Ser Gln Thr Asp Ser Gly Met Val Leu Ala
        1250                1255                1260

Ser Glu Glu Leu Lys Thr Leu Glu Asp Arg Asn Lys Leu Ser Pro
        1265                1270                1275

Ser Phe Gly Gly Met Met Pro Ser Lys Ser Arg Glu Ser Val Ala
        1280                1285                1290

Ser Glu Gly Ser Asn Gln Thr Ser Gly Tyr Gln Ser Gly Tyr His
        1295                1300                1305

Ser Asp Asp Thr Asp Thr Thr Val Tyr Ser Ser Asp Glu Ala Gly
        1310                1315                1320

Leu Leu Lys Met Val Asp Ala Ala Val His Ala Asp Ser Gly Thr
        1325                1330                1335

Thr Leu Gln Leu Thr Ser Cys Leu Asn Gly Ser Gly Pro Val Pro
        1340                1345                1350

Ala Pro Pro Pro Thr Pro Gly Asn His Glu Arg Gly Ala Ala
        1355                1360                1365

<210> SEQ ID NO 64
<211> LENGTH: 1343
<212> TYPE: PRT
<213> ORGANISM: Rattus sp.

<400> SEQUENCE: 64

Met Glu Ser Arg Ala Leu Leu Ala Val Ala Leu Trp Phe Cys Val Glu
1               5                   10                  15

Thr Arg Ala Ala Ser Val Gly Leu Pro Gly Asp Ser Leu His Pro Pro
            20                  25                  30

Lys Leu Ser Thr Gln Lys Asp Ile Leu Thr Ile Leu Ala Asn Thr Thr
        35                  40                  45

Leu Gln Ile Thr Cys Arg Gly Gln Arg Asp Leu Asp Trp Leu Trp Pro
    50                  55                  60

Asn Thr Pro Arg Asp Ser Glu Glu Arg Val Leu Val Thr Glu Cys Gly
65                  70                  75                  80

Asp Ser Ile Phe Cys Lys Thr Leu Thr Val Pro Arg Val Val Gly Asn
                85                  90                  95
```

-continued

```
Asp Thr Gly Ala Tyr Lys Cys Phe Tyr Arg Asp Thr Asp Val Ser Ser
            100                 105                 110
Ile Val Tyr Val Tyr Val Gln Asp His Arg Ser Pro Phe Ile Ala Ser
        115                 120                 125
Val Ser Asp Glu His Gly Ile Val Tyr Ile Thr Glu Asn Lys Asn Lys
    130                 135                 140
Thr Val Val Ile Pro Cys Arg Gly Ser Ile Ser Asn Leu Asn Val Ser
145                 150                 155                 160
Leu Cys Ala Arg Tyr Pro Glu Lys Arg Phe Val Pro Asp Gly Asn Arg
                165                 170                 175
Ile Ser Trp Asp Ser Glu Lys Gly Phe Thr Ile Pro Ser Tyr Met Ile
            180                 185                 190
Ser Tyr Ala Gly Met Val Phe Cys Glu Ala Lys Ile Asn Asp Glu Thr
        195                 200                 205
Tyr Gln Ser Ile Met Tyr Ile Val Leu Val Gly Tyr Arg Ile Tyr
    210                 215                 220
Asp Val Val Leu Ser Pro Pro His Glu Ile Glu Leu Ser Ala Gly Glu
225                 230                 235                 240
Lys Leu Val Leu Asn Cys Thr Ala Arg Thr Glu Leu Asn Val Gly Leu
                245                 250                 255
Asp Phe Ser Trp Gln Phe Pro Ser Ser Lys His Gln His Lys Lys Ile
            260                 265                 270
Val Asn Arg Asp Val Lys Ser Leu Pro Gly Thr Val Ala Lys Met Phe
        275                 280                 285
Leu Ser Thr Leu Thr Ile Asp Ser Val Thr Lys Ser Asp Gln Gly Glu
    290                 295                 300
Tyr Thr Cys Thr Ala Tyr Ser Gly Leu Met Thr Lys Lys Asn Lys Thr
305                 310                 315                 320
Phe Val Arg Val His Thr Lys Pro Phe Ile Ala Phe Gly Ser Gly Met
                325                 330                 335
Lys Ser Leu Val Glu Ala Thr Val Gly Ser Gln Val Arg Ile Pro Val
            340                 345                 350
Lys Tyr Leu Ser Tyr Pro Ala Pro Asp Ile Lys Trp Tyr Arg Asn Gly
        355                 360                 365
Arg Pro Ile Glu Ser Asn Tyr Thr Met Ile Val Gly Asp Glu Leu Thr
    370                 375                 380
Ile Met Glu Val Ser Glu Arg Asp Ala Gly Asn Tyr Thr Val Ile Leu
385                 390                 395                 400
Thr Asn Pro Ile Ser Met Glu Lys Gln Ser His Met Val Ser Leu Val
                405                 410                 415
Val Asn Val Pro Pro Gln Ile Gly Glu Lys Ala Leu Ile Ser Pro Met
            420                 425                 430
Asp Ser Tyr Gln Tyr Gly Thr Met Gln Thr Leu Thr Cys Thr Val Tyr
        435                 440                 445
Ala Asn Pro Pro Leu His His Ile Gln Trp Tyr Trp Gln Leu Glu Glu
    450                 455                 460
Ala Cys Ser Tyr Arg Pro Ser Gln Thr Asn Pro Tyr Thr Cys Lys Glu
465                 470                 475                 480
Trp Arg His Val Lys Asp Phe Gln Gly Gly Asn Lys Ile Glu Val Thr
                485                 490                 495
Lys Asn Gln Tyr Ala Leu Ile Glu Gly Lys Asn Lys Thr Val Ser Thr
            500                 505                 510
Leu Val Ile Gln Ala Ala Tyr Val Ser Ala Leu Tyr Lys Cys Glu Ala
```

-continued

```
            515                 520                 525
Ile Asn Lys Ala Gly Arg Gly Glu Arg Val Ile Ser Phe His Val Ile
        530                 535                 540
Arg Gly Pro Glu Ile Thr Val Gln Pro Ala Thr Gln Pro Thr Glu Arg
545                 550                 555                 560
Glu Ser Met Ser Leu Leu Cys Thr Ala Asp Arg Asn Thr Phe Glu Asn
                565                 570                 575
Leu Thr Trp Tyr Lys Leu Gly Ser Gln Ala Thr Ser Val His Met Gly
            580                 585                 590
Glu Ser Leu Thr Pro Val Cys Lys Asn Leu Asp Ala Leu Trp Lys Leu
        595                 600                 605
Asn Gly Thr Val Phe Ser Asn Ser Thr Asn Asp Ile Leu Ile Val Ala
        610                 615                 620
Phe Gln Asn Ala Ser Leu Gln Asp Gln Gly Asn Tyr Val Cys Ser Ala
625                 630                 635                 640
Gln Asp Lys Lys Thr Lys Lys Arg His Cys Leu Val Lys Gln Leu Val
                645                 650                 655
Ile Leu Glu Arg Met Ala Pro Met Ile Thr Gly Asn Leu Glu Asn Gln
            660                 665                 670
Thr Thr Thr Ile Gly Glu Thr Ile Glu Val Val Cys Pro Thr Ser Gly
        675                 680                 685
Asn Pro Thr Pro Leu Ile Thr Trp Phe Lys Asp Asn Glu Thr Leu Val
        690                 695                 700
Glu Asp Ser Gly Ile Val Leu Lys Asp Gly Asn Arg Asn Leu Thr Ile
705                 710                 715                 720
Arg Arg Val Arg Lys Glu Asp Gly Gly Leu Tyr Thr Cys Gln Ala Cys
                725                 730                 735
Asn Val Leu Gly Cys Ala Arg Ala Glu Thr Leu Phe Ile Ile Glu Gly
            740                 745                 750
Val Gln Glu Lys Thr Asn Leu Glu Val Ile Ile Leu Val Gly Thr Ala
        755                 760                 765
Val Ile Ala Met Phe Phe Trp Leu Leu Leu Val Ile Leu Val Arg Thr
        770                 775                 780
Val Lys Arg Ala Asn Glu Gly Glu Leu Lys Thr Gly Tyr Leu Ser Ile
785                 790                 795                 800
Val Met Asp Pro Asp Glu Leu Pro Leu Asp Glu Arg Cys Glu Arg Leu
                805                 810                 815
Pro Tyr Asp Ala Ser Lys Trp Glu Phe Pro Arg Asp Arg Leu Lys Leu
            820                 825                 830
Gly Lys Pro Leu Gly Arg Gly Ala Phe Gly Gln Val Ile Glu Ala Asp
        835                 840                 845
Ala Phe Gly Ile Asp Lys Thr Ala Thr Cys Lys Thr Val Ala Val Lys
        850                 855                 860
Met Leu Lys Glu Gly Ala Thr His Ser Glu His Arg Ala Leu Met Ser
865                 870                 875                 880
Glu Leu Lys Ile Leu Ile His Ile Gly His His Leu Asn Val Val Asn
                885                 890                 895
Leu Leu Gly Ala Cys Thr Lys Pro Gly Gly Pro Leu Met Val Ile Val
            900                 905                 910
Glu Phe Cys Lys Phe Gly Asn Leu Ser Thr Tyr Leu Arg Gly Lys Arg
        915                 920                 925
Asn Glu Phe Val Pro Tyr Lys Ser Lys Gly Ala Arg Phe Arg Ser Gly
        930                 935                 940
```

-continued

```
Lys Asp Tyr Val Gly Glu Leu Ser Val Asp Leu Lys Arg Arg Leu Asp
945                 950                 955                 960

Ser Ile Thr Ser Ser Gln Ser Ser Ala Ser Ser Gly Phe Val Glu Glu
                965                 970                 975

Lys Ser Leu Ser Asp Val Glu Glu Glu Ala Ser Glu Glu Leu Tyr
            980                 985                 990

Lys Asp Phe Leu Thr Leu Glu His  Leu Ile Cys Tyr Ser  Phe Gln Val
        995                 1000                1005

Ala Lys  Gly Met Glu Phe Leu  Ala Ser Arg Lys Cys  Ile His Arg
    1010                1015                1020

Asp Leu  Ala Ala Arg Asn Ile  Leu Leu Ser Glu Lys  Asn Val Val
    1025                1030                1035

Lys Ile  Cys Asp Phe Gly Leu  Ala Arg Asp Ile Tyr  Lys Asp Pro
    1040                1045                1050

Asp Tyr  Val Arg Lys Gly Asp  Pro Arg Leu Pro Leu  Lys Trp Met
    1055                1060                1065

Ala Pro  Glu Thr Ile Phe Asp  Arg Ile Tyr Thr Ile  Gln Ser Gly
    1070                1075                1080

Val Trp  Ser Phe Gly Val Leu  Leu Trp Glu Ile Phe  Ser Leu Gly
    1085                1090                1095

Ala Ser  Pro Tyr Pro Gly Val  Lys Ile Asp Glu Lys  Phe Cys Arg
    1100                1105                1110

Arg Leu  Lys Glu Gly Thr Arg  Met Arg Ala Pro Asp  Tyr Thr Thr
    1115                1120                1125

Pro Glu  Met Tyr Gln Thr Met  Leu Asp Cys Trp His  Glu Asp Pro
    1130                1135                1140

Asn Gln  Arg Pro Ala Phe Ser  Glu Leu Val Glu His  Leu Gly Asn
    1145                1150                1155

Leu Leu  Gln Ala Asn Ala Gln  Gln Asp Gly Lys Asp  Tyr Ile Val
    1160                1165                1170

Leu Pro  Met Ser Glu Thr Leu  Ser Met Glu Glu Asp  Ser Gly Leu
    1175                1180                1185

Ser Leu  Pro Thr Ser Pro Val  Ser Cys Met Glu Glu  Glu Glu Val
    1190                1195                1200

Cys Asp  Pro Lys Phe His Tyr  Asp Asn Thr Ala Gly  Ile Ser His
    1205                1210                1215

Tyr Leu  Gln Asn Ser Lys Arg  Lys Ser Arg Pro Val  Ser Val Lys
    1220                1225                1230

Thr Phe  Glu Asp Ile Pro Leu  Glu Glu Pro Glu Val  Lys Val Ile
    1235                1240                1245

Pro Asp  Asp Ser Gln Thr Asp  Ser Gly Met Val Leu  Ala Ser Glu
    1250                1255                1260

Glu Leu  Lys Thr Leu Glu Asp  Arg Asn Lys Leu Ser  Pro Ser Phe
    1265                1270                1275

Gly Gly  Met Met Pro Ser Lys  Ser Arg Glu Ser Val  Ala Ser Glu
    1280                1285                1290

Gly Ser  Asn Gln Thr Ser Gly  Tyr Gln Ser Gly Tyr  His Ser Asp
    1295                1300                1305

Asp Thr  Asp Thr Thr Val Tyr  Ser Ser Asp Glu Ala  Gly Leu Leu
    1310                1315                1320

Lys Leu  Val Asp Val Ala Gly  His Val Asp Ser Gly  Thr Thr Leu
    1325                1330                1335
```

-continued

Arg Ser Ser Pro Val
        1340

<210> SEQ ID NO 65
<211> LENGTH: 1348
<212> TYPE: PRT
<213> ORGANISM: Callipepla sp.

<400> SEQUENCE: 65

Met Glu Leu Gly Pro Leu Arg Val Leu Thr Val Leu Leu Cys Leu Ala
1               5                   10                  15

Pro Val Phe Ala Gly Leu Phe Ile Ser Met Asp Gln Pro Thr Leu Ser
            20                  25                  30

Ile Gln Lys Ser Val Leu Thr Ile Thr Thr Asn Asp Thr Leu Asn Ile
        35                  40                  45

Thr Cys Ser Gly Gln Arg Ala Val Tyr Trp Ser Trp Pro Asn Asn Gln
    50                  55                  60

Ser Ser Val Glu Lys Arg Leu Ala Val Thr Gly Cys Ser Glu Gly Pro
65                  70                  75                  80

Phe Cys Lys Thr Leu Thr Leu Leu Arg Val Ile Gly Asn Asp Thr Gly
                85                  90                  95

Asp Tyr Arg Cys Leu Tyr Gly Asp Ser Gln Ala Ala Thr Thr Ile Tyr
            100                 105                 110

Val Tyr Val Gln Asp Tyr Arg Ser Pro Phe Val Thr Ser Val Gly Asp
        115                 120                 125

Gln Leu Gly Ile Val Tyr Ile Thr Lys Asn Lys Thr Val Val Val Pro
    130                 135                 140

Cys Leu Gly Thr Val Ser Asn Leu Asn Val Ser Leu His Ala Lys Tyr
145                 150                 155                 160

Pro Glu Lys Val Phe Val Pro Asp Gly Lys Ser Ile Ser Trp Asp Asn
                165                 170                 175

Lys Lys Gly Phe Thr Ile Pro Ser His Leu Ile Asn Tyr Ala Gly Met
            180                 185                 190

Val Phe Cys Glu Ala Lys Ile Asp Asn Glu Ser Tyr Gln Ser Val Ile
        195                 200                 205

Tyr Ile Val Ala Val Val Gly Tyr Arg Ile Tyr Asp Leu Thr Met Asn
    210                 215                 220

Pro His Tyr Gln Val Glu Leu Ala Val Gly Glu Lys Leu Val Leu Asn
225                 230                 235                 240

Cys Thr Val Arg Thr Glu Leu Asn Val Gly Ile Asp Phe Arg Trp Asp
                245                 250                 255

Tyr Pro Ser Ile Lys Glu Arg Ala Thr Ile Arg Asp Leu Lys Thr
            260                 265                 270

Thr Ala Gly Glu Ile Lys Thr Phe Val Ser Thr Leu Thr Ile Glu Ser
        275                 280                 285

Val Asn Leu Ser Asp Lys Gly Arg Tyr Thr Cys Ala Ala Ser Ser Gly
    290                 295                 300

Arg Met Asn Met Lys Asn Ser Ser Tyr Phe Ile Ile His Glu Ser Pro
305                 310                 315                 320

Phe Ile His Leu Glu Lys Met Glu Asn Val Val Glu Met Lys Leu Gly
                325                 330                 335

Asp Thr Val Ser Ile Pro Val Lys Phe Lys Gly Tyr Pro Pro Pro Glu
            340                 345                 350

Ala Lys Trp Tyr Lys Asn Gly Lys Val Ile Asn Ala Asn His Thr Val
        355                 360                 365

-continued

```
Lys Leu Gly Tyr Ala Leu Val Ile Thr Glu Ala Thr Glu Lys Asp Ala
    370                 375                 380

Gly Asn Tyr Thr Val Val Leu Thr Asn Pro Thr Asn Lys Met Gln Lys
385                 390                 395                 400

Arg His Thr Phe Thr Leu Leu Val Asn Val Pro Pro Gln Ile Gly Glu
                    405                 410                 415

Asn Ala Leu Met Ala Pro Val Asp Ser Tyr Lys Tyr Gly Ser Thr Gln
                420                 425                 430

Ala Leu Thr Cys Thr Ile Tyr Ala Val Pro Pro Ala Ala Val Leu
                435                 440                 445

Trp Tyr Trp Gln Leu Glu Glu Glu Cys Thr Phe Ser Pro Gln Lys Val
    450                 455                 460

Arg Leu Gly Ala Asn Pro Tyr Ala Cys Arg Lys Trp Lys Val Ile Ser
465                 470                 475                 480

Glu Arg Lys Gly Gly Asn Gln Val Glu Ile Lys Gln Arg Val Val Thr
                485                 490                 495

Ile Ala Gly Lys Thr Lys Thr Val Ser Thr Leu Val Ile Gln Ala Ala
                500                 505                 510

Asn Val Ser Ala Leu Tyr Arg Cys Met Ala Thr Asn Arg Ala Gly Ser
            515                 520                 525

Ser Glu Arg Val Ile Ser Phe His Val Thr Arg Gly Leu Glu Ile Asn
    530                 535                 540

Leu Gln Pro Arg Ser Gln Leu Thr Glu Lys Asp Asn Thr Ser Leu Gln
545                 550                 555                 560

Cys Thr Ala Asp Lys Phe Thr Phe Glu Lys Leu Ser Trp Tyr Lys Leu
                565                 570                 575

Ser Thr His Val Ser Gln Thr Pro Phe Gly Gly Leu Pro Met Pro Val
                580                 585                 590

Cys Lys Asn Leu Asp Ala Leu Gln Lys Leu Asn Ala Thr Val Ser Asn
            595                 600                 605

Val Asn Gly Glu Asn Val Thr Leu Glu Leu Ile Leu Arg Asn Ile Ser
    610                 615                 620

Leu Gln Asp Gly Gly Asp Tyr Val Cys Ile Ala Gln Asp Lys Lys Ala
625                 630                 635                 640

Lys Thr Gln His Cys Leu Val Lys His Leu Thr Val Gln Glu Pro Leu
                645                 650                 655

His Pro Arg Leu Val Gly Asn Leu Glu Asn Gln Thr Thr Asn Ile Gly
                660                 665                 670

Glu Thr Ile Glu Val Leu Cys Thr Val Asn Gly Val Pro Pro Pro Asn
            675                 680                 685

Ile Thr Trp Phe Lys Asn Ser Glu Thr Leu Phe Glu Asp Ser Gly Ile
    690                 695                 700

Val Leu Lys Asp Gly Asn Lys Thr Leu Thr Ile Arg Arg Val Arg Lys
705                 710                 715                 720

Glu Asp Gly Gly Leu Tyr Thr Cys Leu Ala Cys Asn Ile Leu Gly Cys
                725                 730                 735

Lys Lys Ala Glu Ala Phe Phe Ser Val Gln Gly Ala Glu Glu Lys Thr
                740                 745                 750

Asn Leu Glu Leu Ile Ile Leu Val Gly Thr Ala Val Ile Ala Met Phe
            755                 760                 765

Phe Trp Leu Leu Leu Val Ile Ile Leu Arg Thr Val Lys Arg Ala Asn
    770                 775                 780
```

-continued

```
Gly Gly Asp Met Lys Thr Gly Tyr Leu Ser Ile Ile Met Asp Pro Asp
785                 790                 795                 800

Glu Val Pro Ile Asp Glu His Cys Glu Arg Leu Pro Tyr Asp Ala Ser
            805                 810                 815

Lys Trp Glu Phe Pro Arg Asp Arg Leu Lys Leu Gly Lys Pro Leu Gly
        820                 825                 830

Arg Gly Ala Phe Gly Gln Val Ile Glu Ala Asp Ala Phe Gly Ile Asp
    835                 840                 845

Lys Thr Ala Thr Cys Arg Thr Val Ala Val Lys Met Leu Lys Glu Gly
850                 855                 860

Ala Thr His Ser Glu His Arg Ala Leu Met Ser Glu Leu Lys Ile Leu
865                 870                 875                 880

Ile His Ile Gly His His Leu Asn Val Val Asn Leu Leu Gly Ala Cys
                885                 890                 895

Thr Lys Pro Gly Gly Pro Leu Met Val Ile Val Glu Tyr Cys Lys Phe
            900                 905                 910

Gly Asn Leu Ser Ala Tyr Leu Arg Ser Lys Arg Ser Glu Phe Ile Pro
        915                 920                 925

Tyr Lys Met Lys Ser Ala Arg Phe Arg Gln Gly Lys Glu Asn Tyr Thr
    930                 935                 940

Gly Asp Ile Ser Thr Asp Leu Lys Gln Arg Leu Asp Ser Ile Thr Ser
945                 950                 955                 960

Ser Gln Ser Ser Thr Ser Ser Gly Phe Val Glu Glu Arg Ser Leu Ser
                965                 970                 975

Asp Val Glu Glu Glu Asp Ala Gly Ser Glu Asp Leu Cys Lys Asn Pro
            980                 985                 990

Leu Thr Met Glu Asp Leu Ile Cys Tyr Ser Phe Gln Val Ala Arg Gly
        995                 1000                1005

Met Glu Phe Leu Ala Ser Arg Lys Cys Ile His Arg Asp Leu Ala
    1010                1015                1020

Ala Arg Asn Ile Leu Leu Ser Asp Asn Asn Val Lys Ile Cys
    1025                1030                1035

Asp Phe Gly Leu Ala Arg Asp Ile Tyr Lys Asp Pro Asp Tyr Val
    1040                1045                1050

Arg Lys Gly Asp Ala Arg Leu Pro Leu Lys Trp Met Ala Pro Glu
    1055                1060                1065

Thr Ile Phe Asp Arg Val Tyr Thr Ile Gln Ser Asp Val Trp Ser
    1070                1075                1080

Phe Gly Val Leu Leu Trp Glu Ile Phe Ser Leu Gly Ala Ser Pro
    1085                1090                1095

Tyr Pro Gly Val Lys Ile Asp Glu Glu Phe Cys Arg Arg Leu Lys
    1100                1105                1110

Glu Gly Thr Arg Met Arg Ala Pro Asp Tyr Thr Thr Pro Glu Met
    1115                1120                1125

Tyr Gln Thr Met Leu Asp Cys Trp His Gly Asp Pro Lys Gln Arg
    1130                1135                1140

Pro Thr Phe Ser Glu Leu Val Glu His Leu Gly Asn Leu Leu Gln
    1145                1150                1155

Ala Asn Val Arg Gln Asp Gly Lys Asp Tyr Val Val Leu Pro Leu
    1160                1165                1170

Ser Val Ser Leu Asn Met Glu Glu Asp Ser Gly Leu Ser Leu Pro
    1175                1180                1185

Thr Ser Pro Ala Ser Cys Lys Glu Glu Glu Glu Val Cys Asp Pro
```

-continued

```
            1190                1195                1200
Lys Phe His Tyr Asp Asn Thr Ala Gly Ile Ser Gln Tyr Arg Gln
    1205                1210                1215
Gly Ser Lys Arg Lys Ser Arg Pro Val Ser Val Lys Thr Phe Glu
    1220                1225                1230
Asp Ile Pro Leu Val Thr Thr Val Lys Val Val Gln Glu Glu Asn
    1235                1240                1245
Gln Thr Asp Ser Gly Met Val Leu Ala Ser Glu Glu Leu Lys Thr
    1250                1255                1260
Leu Glu Glu Gln Asp Lys Gln Val Lys Ile Pro Phe Ser Thr Leu
    1265                1270                1275
Ala Pro Ser Lys Ser Asn Glu Ser Val Met Ser Glu Ala Ser Asn
    1280                1285                1290
Gln Thr Ser Gly Tyr Gln Ser Gly Tyr His Ser Asp Asp Met Asp
    1295                1300                1305
Asn Met Val Cys Ser Ser Glu Asp Thr Glu Leu Leu Cys Ala Gln
    1310                1315                1320
Glu Ala Ser Pro Thr Leu Pro Arg Cys Ala Trp Pro Gly Ile Tyr
    1325                1330                1335
Ser Pro Ala Pro Val Ala Ser Leu Pro Leu
    1340                1345
```